US010758524B2

(12) United States Patent
Zheng et al.

(10) Patent No.: US 10,758,524 B2
(45) Date of Patent: *Sep. 1, 2020

(54) COMPOSITIONS AND METHODS FOR SELECTIVELY DEPLETING SENESCENT CELLS

(71) Applicant: BioVentures, LLC, Little Rock, AR (US)

(72) Inventors: Guangrong Zheng, Little Rock, AR (US); Daohong Zhou, Little Rock, AR (US); Xingui Liu, Little Rock, AR (US); Yingying Wang, Little Rock, AR (US); Jianhui Chang, Little Rock, AR (US); Wei Feng, Little Rock, AR (US); Lijian Shao, Little Rock, AR (US); Yi Luo, Little Rock, AR (US)

(73) Assignee: BioVentures, LLC, Little Rock, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/057,021

(22) Filed: Aug. 7, 2018

(65) Prior Publication Data

US 2018/0369223 A1 Dec. 27, 2018

Related U.S. Application Data

(62) Division of application No. 15/328,368, filed as application No. PCT/US2015/041470 on Jul. 22, 2015, now Pat. No. 10,071,087.

(60) Provisional application No. 62/027,572, filed on Jul. 22, 2014, provisional application No. 62/087,499, filed on Dec. 4, 2014, provisional application No. 62/134,155, filed on Mar. 17, 2015.

(51) Int. Cl.
| | |
|---|---|
| *A61K 31/45* | (2006.01) |
| *A61K 31/55* | (2006.01) |
| *A61K 31/4015* | (2006.01) |
| *A61K 31/5377* | (2006.01) |
| *A61K 31/4412* | (2006.01) |
| *A61K 31/443* | (2006.01) |
| *A61K 31/4439* | (2006.01) |
| *A61K 31/444* | (2006.01) |
| *A61K 31/4545* | (2006.01) |
| *A61K 31/635* | (2006.01) |
| *C07D 223/10* | (2006.01) |
| *C07D 401/06* | (2006.01) |
| *C07D 405/06* | (2006.01) |
| *C07D 207/38* | (2006.01) |
| *C07D 211/88* | (2006.01) |
| *A23L 33/10* | (2016.01) |
| *C07D 211/76* | (2006.01) |
| *C07D 211/96* | (2006.01) |

(52) U.S. Cl.
CPC .............. *A61K 31/45* (2013.01); *A23L 33/10* (2016.08); *A61K 31/4015* (2013.01); *A61K 31/443* (2013.01); *A61K 31/444* (2013.01); *A61K 31/4412* (2013.01); *A61K 31/4439* (2013.01); *A61K 31/4545* (2013.01); *A61K 31/5377* (2013.01); *A61K 31/55* (2013.01); *A61K 31/635* (2013.01); *C07D 207/38* (2013.01); *C07D 211/76* (2013.01); *C07D 211/88* (2013.01); *C07D 211/96* (2013.01); *C07D 223/10* (2013.01); *C07D 401/06* (2013.01); *C07D 405/06* (2013.01); *A23V 2002/00* (2013.01)

(58) Field of Classification Search
CPC .... A61K 31/45; A61K 31/55; A61K 31/4015; A61K 31/5377
See application file for complete search history.

(56) References Cited

U.S. PATENT DOCUMENTS

| | | |
|---|---|---|
| 4,241,046 A | 12/1980 | Papahadjopoulos et al. |
| 4,394,448 A | 7/1983 | Szoka, Jr. et al. |
| 4,529,561 A | 7/1985 | Hunt et al. |
| 4,755,388 A | 7/1988 | Heath et al. |
| 4,828,837 A | 5/1989 | Uster et al. |
| 4,925,661 A | 5/1990 | Huang |
| 4,954,345 A | 9/1990 | Muller |
| 4,957,735 A | 9/1990 | Huang |
| 5,043,164 A | 8/1991 | Huang et al. |
| 5,064,655 A | 11/1991 | Uster et al. |
| 5,077,211 A | 12/1991 | Yarosh |
| 5,223,409 A | 6/1993 | Ladner et al. |
| 5,264,618 A | 11/1993 | Felgner et al. |
| 5,403,484 A | 4/1995 | Ladner et al. |
| 5,491,069 A | 2/1996 | Dirmi et al. |
| 5,571,698 A | 11/1996 | Ladner et al. |
| 5,888,764 A | 3/1999 | Mountz et al. |

(Continued)

FOREIGN PATENT DOCUMENTS

| | | |
|---|---|---|
| CN | 101774875 A | 7/2010 |
| CN | 101939008 A | 1/2011 |

(Continued)

OTHER PUBLICATIONS

Adams, D. et al., "Synthesis, cellular evaluation, and mechanism of action of piperlongumine analogs," PNAS, Sep. 18, 2012, pp. 15115-15120, vol. 109, No. 38.

(Continued)

*Primary Examiner* — Bruck Kifle
(74) *Attorney, Agent, or Firm* — Polsinelli PC

(57) ABSTRACT

The present disclosure provides compositions and methods for selectively killing senescent cells, wherein the composition comprises piperlongumine (PL) or derivative thereof. The selective killing of senescent cells may delay aging and/or treat age-related disorders.

11 Claims, 9 Drawing Sheets

(56) References Cited

U.S. PATENT DOCUMENTS

| | | |
|---|---|---|
| 6,492,389 B1 | 12/2002 | Huang et al. |
| 6,566,495 B1 | 5/2003 | Fodor et al. |
| 6,572,876 B2 | 6/2003 | Waggle et al. |
| 7,939,313 B2 | 5/2011 | Heyduk et al. |
| 8,232,273 B2 | 7/2012 | Baell et al. |
| 10,071,087 B2 | 9/2018 | Zheng et al. |
| 2005/0084876 A1 | 4/2005 | Tschopp et al. |
| 2005/0208151 A1 | 9/2005 | Hurez et al. |
| 2006/0140959 A1 | 6/2006 | Fisher et al. |
| 2007/0072860 A1 | 3/2007 | Bruncko et al. |
| 2008/0171051 A1 | 7/2008 | Johnston et al. |
| 2009/0312373 A1 | 12/2009 | Lee et al. |
| 2010/0086941 A1 | 4/2010 | Adami et al. |
| 2010/0093613 A1 | 4/2010 | Kunkel |
| 2010/0310504 A1 | 12/2010 | Lowe et al. |
| 2011/0028387 A1 | 2/2011 | Garcia et al. |
| 2011/0053938 A1 | 3/2011 | Foley et al. |
| 2011/0086860 A1 | 4/2011 | Kimura et al. |
| 2012/0059004 A1 | 3/2012 | Elliott et al. |
| 2012/0156134 A1 | 6/2012 | Squires |
| 2012/0157455 A1 | 6/2012 | Foley et al. |
| 2013/0195884 A1 | 8/2013 | Boutros et al. |
| 2013/0237539 A1 | 9/2013 | Foley et al. |
| 2014/0005190 A1 | 1/2014 | Baell et al. |
| 2014/0024639 A1 | 1/2014 | Adams et al. |
| 2014/0199234 A1 | 7/2014 | Wang et al. |
| 2014/0356322 A1 | 12/2014 | Crews et al. |
| 2015/0291562 A1 | 10/2015 | Crew et al. |
| 2016/0095850 A1 | 4/2016 | Cooper et al. |
| 2016/0176916 A1 | 6/2016 | Bradner et al. |
| 2016/0339019 A1 | 11/2016 | Laberge et al. |
| 2017/0056421 A1 | 3/2017 | Zhou et al. |
| 2017/0246155 A1 | 8/2017 | Zheng et al. |
| 2017/0348307 A1 | 12/2017 | Laberge et al. |
| 2018/0002431 A1 | 1/2018 | Zhou et al. |
| 2018/0021323 A1 | 1/2018 | Zhou et al. |
| 2019/0054097 A1 | 2/2019 | Zhou et al. |
| 2019/0135801 A1 | 5/2019 | Zheng et al. |

FOREIGN PATENT DOCUMENTS

| | | |
|---|---|---|
| CN | 102125552 A | 7/2011 |
| CN | 102146054 A | 8/2011 |
| CN | 103601670 A | 2/2014 |
| CN | 105085620 A | 11/2015 |
| EP | 0532767 A1 | 3/1993 |
| EP | 2985285 A1 | 2/2016 |
| JP | 11349568 A | 12/1999 |
| WO | 2002026940 A1 | 4/2002 |
| WO | 2002097053 A2 | 12/2002 |
| WO | 2004106328 A1 | 12/2004 |
| WO | 2006023778 A2 | 3/2006 |
| WO | 2008119741 A2 | 10/2008 |
| WO | 2009114126 A1 | 9/2009 |
| WO | 2009129317 A1 | 10/2009 |
| WO | 2009155386 A1 | 12/2009 |
| WO | 2010080503 A1 | 7/2010 |
| WO | 2010120943 A1 | 10/2010 |
| WO | 2010138588 A2 | 12/2010 |
| WO | 2011009861 A1 | 1/2011 |
| WO | 2011130395 A1 | 10/2011 |
| WO | 2012030408 A1 | 3/2012 |
| WO | 2013083098 A2 | 6/2013 |
| WO | 2013106643 A2 | 7/2013 |
| WO | 2013178821 A1 | 12/2013 |
| WO | 2014089124 A1 | 6/2014 |
| WO | 2014108452 A1 | 7/2014 |
| WO | 2014174511 A1 | 10/2014 |
| WO | 2015116740 A1 | 8/2015 |
| WO | 2015171591 A1 | 11/2015 |
| WO | 2016014625 A1 | 1/2016 |
| WO | 2016118855 A1 | 7/2016 |
| WO | 2016118859 A1 | 7/2016 |
| WO | 2017012774 A1 | 1/2017 |
| WO | 2017101851 A1 | 6/2017 |
| WO | 2017184995 A1 | 10/2017 |

OTHER PUBLICATIONS

Baker, D et al., "Clearance of p16Ink4a-positive senescent cells delays ageing-associated disorders," Nature, Nov. 10, 2011, pp. 232-236, vol. 479, No. 7372, Macmillian Publishers Limited.

Banerjee, T. et al., "The crystal and molecular structure of N-(3,4,5-trimethoxycinnamoyl)-A3-piperidine-2-one, an amide alkaloid (piperlongumine), C17H19NO5," Can. J. Chem., 1986, pp. 876-880, vol. 64.

Baritaki, S. et al., "Chemotherapeutic drugs sensitize cancer cells to Trail-mediated apoptosis: up-regulation of DR5 and inhibition of Yin Yang 1," Mol. Cancer Ther., Apr. 2007, pp. 1387-1399, vol. 6, No. 4.

Barton, K. et al., "Selective HDAC Inhibition for the Disruption of Latent HIV-1 Infection," PLOS ONE, Aug. 2014, pp. 1-11, vol. 9, No. 8, e102684.

Beerman, I. et al., "Stem cells and the aging hematopoietic system," Curr. Opin. Immunol., 2010, pp. 500-506, vol. 22.

Bensoussan, C. et al., "Iron-catalyzed cross-coupling between C-bromo mannopyranoside derivatives and a vinyl Grignard reagent: toward the synthesis of the C31-C52 fragment of amphidinol 3," Tetrahedron, 2013, pp. 7759-7770, vol. 69, No. 36, Elsevier Ltd.

Bezerra, D. et al., "Overview of the therapeutic potential of piplartine (piperlongumine)," Eur. J. Pharma. Sci., 2013, pp. 453-463, vol. 48, No. 3, Elsevier B.V., Amsterdam.

Bokesch, H. et al., "A New Hypoxia Inducible Factor-2 Inhibitory Pyrrolinone Alkaloid from Roots and Stems of Piper sarmentosum," Chem. Pharm. Bull., 2011, pp. 1178-1179, vol. 59, No. 9, Pharmaceutical Society of Japan.

Bucknall, M. et al., "Practical Quantitative Biomedical Applications of MALDI-TOF Mass Spectrometry," J. Am. Soc. Mass. Spectrom., 2002, pp. 1015-1027, vol. 13, Elsevier Science Inc.

Burd, C. et al., "Monitoring tumorigenesis and senescence in vivo with a p16(INK4a)-luciferase model," Cell, 2013, pp. 340-351, vol. 152.

Campisi, J., "Aging, cellular senescence, and cancer," Annu. Rev. Physiol., 2013, pp. 685-705, vol. 75.

Campisi, J. et al., "Senescent Cells, Tumor Suppression, and Organismal Aging: Good Citizens, Bad Neighbors," Cell, Feb. 25, 2005, pp. 513-522, vol. 120, Elsevier Inc.

Campisi, J., "Cellular senescence: putting the paradoxes in perspective," Curr. Opin. Genet. Dev., 2011, pp. 107-112, vol. 21, Elsevier.

Carell, T. et al., "A Solution-Phase Screening Procedure for the Isolation of Active Compounds from a Library of Molecules," Angew. Chem. Int. Ed. Engl., 1994, pp. 2059-2061, vol. 33, No. 20.

Caserta, T. et al., "Q-VD-OPh, a broad spectrum caspase inhibitor with potent antiapoptotic properties," Apoptosis, 2003, pp. 345-352, vol. 8.

Chatterjee, A. et al., "Alkaloids of Piper Longum Linn-I: Structure and Synthesis of Piperlongumine and Piperlonguminine," Tetrahedron, 1967, pp. 1769-1781, vol. 23, No. 4, Pergamon Press, Northern Ireland.

Chen, S. et al., "Celecoxib Promotes c-FLIP Degradation through Akt-Independent Inhibition of GSK3," Cancer Res., 2011, pp. 6270-6281, vol. 71, No. 19.

Chen, Q. et al., "Apo2L/TRAIL and Bcl-2-related proteins regulate type I interferon-induced apoptosis in multiple myeloma," Blood, Oct. 1, 2001, pp. 2183-2192, vol. 98, No. 7.

Childs, B. et al., "Senescence and apoptosis: dueling or complementary cell fates?," EMBO Rep., 2014, pp. 1139-1153, vol. 15.

Cho, C. et al., "An Unnatural Biopolymer," Sci., Sep. 3, 1993, pp. 1303-1305, vol. 261.

Citrin, D. et al., "Role of type II pneumocyte senescence in radiation-induced lung fibrosis," J. Natl. Can. Inst., 2013, pp. 1474-1484, vol. 105.

Coppe, J. et al., "The senescence-associated secretory phenotype: the dark side of tumor suppression," Annu. Rev. Pathol., 2010, pp. 99-118, vol. 5.

(56) References Cited

OTHER PUBLICATIONS

Cory, S. et al., "The Bcl2 family: regulators of the cellular life-or-death switch," Nat. Rev. Can., 2002, pp. 647-656, vol. 2.

Cull, M. et al., "Screening for receptor ligands using large libraries of peptides linked to the C terminus of the lac repressor," PNAS, Mar. 1992, pp. 1865-1869, vol. 89.

Cwirla, S. et al., "Peptides on phage: A vast library of peptides for identifying ligands," PNAS, Aug. 1990, pp. 6378-6382, vol. 87.

Czabotar, P. et al., "Control of apoptosis by the BCL-2 protein family: implications for physiology and therapy," Nat. Rev. Mol. Cell Biol., 2014, pp. 49-63, vol. 15.

Debacq-Chainiaux, F. et al., "Protocols to detect senescence-associated beta-galactosidase (SA-betagal) activity, a biomarker of senescent cells in culture and in vivo," Nat. Protoc., 2009, pp. 1798-1806, vol. 4.

Demaria, M. et al., "An Essential Role for Senescent Cells in Optimal Wound Healing through Secretion of PDGF-AA," Dev. Cell, 2014, pp. 722-733, vol. 31.

Devlin, J. et al., "Random Peptide Libraries: A Source of Specific Protein Binding Molecules," Sci., Jul. 27, 1990, pp. 404-406, vol. 249, No. 4967, American Association for Advancement of Science.

Dewitt, S. et al., "'Diversomers': An approach to nonpeptide, nonoligomeric chemical diversity," PNAS, Aug. 1993, pp. 6909-6913, vol. 90.

Di Pietro, R. et al., "Ionnizing radition sensitizes erythroleukemic cells but not normal erythroblasts to tumor necrosis factor-related apoptosis-inducing ligand (TRAIL)-mediated cytotoxicity by selective up-regulation of TRAIL-R1," Blood, May 1, 2001, pp. 2596-2603, vol. 97, No. 9.

Dodson, C. et al., "Cenocladamide, a dihydropyridone alkaloid from Piper cenocladum," Phytochemistry, 2000, pp. 51-54, vol. 53, Elsevier Science Ltd.

Duh, C. et al., "Cytotoxic Pyridone Alkaloids From the Leaves of Piper Aborescens," J. Nat. Prod., Nov.-Dec. 1990, pp. 1575-1577, vol. 53, No. 6.

Dykstra, B. et al., "Clonal analysis reveals multiple functional defects of aged murine hematopoietic stem cells," J. Exp. Med., 2011, pp. 2691-2703, vol. 208.

Erb, E. et al., "Recursive deconvolution of combinatorial chemical libraries," PNAS, Nov. 1994, pp. 11422-11426, vol. 91.

Extended European Search Report dated Oct. 5, 2017 from related European Patent Application No. 15789264.7; 7 pgs.

Extended European Search Report dated Jan. 2, 2018 from related European Patent Application No. 15824181.0; 9 pgs.

Felici, F., "Selection of Antibody Ligands from a Large Library of Oligopeptides Expressed on a Multivalent Exposition Vector," J. Mol. Biol., 1991, pp. 301-310, vol. 222.

Fleenor, C. et al., "Ionizing radiation and hematopoietic malignancies: altering the adaptive landscape," Cell Cycle, 2010, pp. 3005-3011, vol. 9.

Fodor, S. et al., "Multiplexed biochemical assays with biological chips," Nature, 1993, pp. 555-556, vol. 364, No. 6437.

Fontenele, J. et al., "Antiplatelet effects of piplartine, an alkamide isolated from Piper tuberculatum: possible involvement of cyclooxygenase blockade and antioxidant activity," J. Pharm. Pharmacol., 2009, pp. 511-515, vol. 61, No. 4.

Gallop, M. et al., "Applications of Combinatorial Technologies to Drug Discovery. 1. Background and Peptide Combinatorial Libraries," J. Med. Chem., Apr. 1994, pp. 1233-1251, vol. 37, No. 9.

Geiger, H. et al., "Regulation of hematopoietic stem cell aging in vivo by a distinct genetic element," PNAS, 2005, pp. 5102-5107, vol. 102.

Geiger, H. et al., "The ageing haematopoietic stem cell compartment," Nat. Rev. Immunol., 2013, pp. 376-389, vol. 13.

Gobom, J. et al., "Detection and Quantification of Neurotensin in Human Brain Tissue by Matrix-Asserted Laser Desorption/Ionization Time-of-Flight Mass Spectrometry," Anal. Chem., 2000, pp. 3320-3326, vol. 72.

Harfouche, G. et al., "Response of normal stem cells to ionizing radiation: a balance between homeostasis and genomic stability," Mutat. Res., 2010, pp. 167-174, vol. 704.

Houghten, R. et al., "The Use of Synthetic Peptide Combinatorial Libraries for the Identification of Bioactive Peptides," Biotechniques, 1991, pp. 412-421, vol. 13, No. 3.

International Search Report and Written Opinion dated Sep. 18, 2015 from related International Patent Application No. PCT/US2015/029208; 13 pgs.

International Search Report and Written Opinion dated Oct. 23, 2015 from related International Patent Application No. PCT/US2015/041470; 9 pgs.

International Search Report and Written Opinion dated Apr. 1, 2016 from related International Patent Application No. PCT/US2016/014518; 9 pgs.

International Search Report and Written Opinion dated Apr. 1, 2016 from related International Patent Application No. PCT/US2016/014510; 12 pgs.

International Search Report and Written Opinion dated Jul. 11, 2017 from related International Patent Application No. PCT/US2017/028875; 9 pgs.

International Search Report and Written Opinion dated Jun. 29, 2015 from related International Patent Application No. PCT/US2015/013387; 34 pgs.

Janzen, V. et al., "Stem-cell ageing modified by the cyclin-dependent kinase inhibitor p16INK4a," Nature, 2006, pp. 421-426, vol. 443.

Joshi, B. et al., "On the Structure of Piplartine and a Synthesis of Dihydropiplartine," Tetrahedron Lett., 1968, pp. 2395-2400, vol. 9, No. 20, Pergamon Press, Great Britain.

Jozefczuk, J. et al., "Preparation of Mouse Embryonic Fibroblast Cells Suitable for Culturing Human Embryonic and Induced Pluripotent Stem Cells," J. Vis. Exp., Jun. 2012, pp. 1-5, vol. 64, Issue e3854.

Kubo, M. et al., "Evaluation of Constituents of Piper retrofractum Fruits on Neurotrophic Activity," J. Nat. Prod., 2013, pp. 769-773, vol. 76, No. 4, The American Chemical Society and American Society of Pharmacognosy.

Kumar, J. et al., "Synthesis, anticancer, and antibacterial activities of piplartine derivatives on cell cycle regulation and growth inhibition," Journal of Asian Natural Products Research, Jun. 1, 2013, pp. 658-669, vol. 15, No. 6, Taylor & Francis Group.

Laberge, R. et al., "Mitochondrial DNA damage induces apoptosis in senescent cells," Cell Death Dis., 2013, p. e727, vol. 4.

Lam, K. "Mini-review. Application of combinatorial library methods in cancer research and drug discovery," Anti-Cancer Drug Des., 1997, pp. 145-167, vol. 12, No. 3.

Lam, K. et al., "A new type of synthetic peptide library for identifying ligand-binding activity," Nature, Nov. 7, 1991, pp. 82-84, vol. 354.

Le, O. et al., "Ionizing radiation-induced long-term expression of senescence markers in mice is independent of p53 and immune status," Aging Cell, 2010, pp. 398-409, vol. 9.

Le Couteur, D. et al., "Aging biology and novel targets for drug discovery," J. Gerontol. A Biol. Sci. Med. Sci., 2012, pp. 168-174, vol. 67.

Lee, S.-J. et al., "Berberine sensitizes TRAIL-induced apoptosis through proteasome-mediated downregulation of c-FLIP and Mcl-1 proteins," Int. J. Oncol., 2011, pp. 485-492, vol. 38.

Lessene, G. et al., "Structure-guided design of a selective BCL-X(L) inhibitor," Nat. Chem. Biol., 2013, pp. 390-397, vol. 9.

Loo, D. et al., "Measurement of Cell Death," Methods Cell Biol., 1998, pp. 251-264, vol. 57, Chapter 14, Academic Press.

Marcotte, R. et al., "Replicative senescence revisited," J. Gerontol. A Biol. Sci. Med. Sci., 2002, pp. B257-B269, vol. 57.

Mawji, I. et al., "A Chemical Screen Identifies Anisomycin as an Anoikis Sensitizer That Functions by Decreasing FLIP Protein Synthesis," Cancer Res., Sep. 1, 2007, pp. 8307-8315, vol. 67, No. 17.

Meng, A. et al,. "Sphingomyelin synthase as a potential target for D609-induced apoptosis in U937 human monocytic leukemia cells," Exp. Cell Res., 2004, pp. 385-392, vol. 292.

(56) References Cited

OTHER PUBLICATIONS

Mirgorodskaya, E. et al., "Characterization of Protein Glycosylation by MALDI-TOFMS," Meth. Mol. Biol., 2000, pp. 273-292, vol. 146, Humana Press Inc.
Munoz-Espin, D. et al., "Cellular senescence: from physiology to pathology," Nat. Rev. Mol. Cell Biol., 2014, pp. 482-496, vol. 15.
Nopora, A. et al., "Bcl-2 Controls Dendritic Cell Longevity In Vivo," J. Immunol., Sep. 2002, pp. 3006-3014, vol. 169, No. 6.
Notice of Allowance dated May 8, 2018 from related U.S. Appl. No. 15/328,368; 5 pgs.
Office Action dated Oct. 23, 2017 from related U.S. Appl. No. 15/328,368; 8 pgs.
Office Action dated Feb. 27, 2018 from related U.S. Appl. No. 15/328,368; 6 pgs.
Raj, L. et al., "Selective killing of cancer cells by a small molecule targeting the stress response to ROS," Nature, Jul. 14, 2011, pp. 231-234, vol. 475, Macmillan Publishers Limited.
Raja, S. et al., "The natural product honokiol preferentially inhibits cellular FLICE-inhibitory protein and augments death receptor-induced apoptosis," Mol. Cancer Ther., 2008, pp. 2212-2223, vol. 7, No. 7.
Rao, V. et al., "Synthesis and biological evaluation of new piplartine analogues as potent aldose reductase inhibitors (ARIs)," Eur. J. Med. Chem., 2012, pp. 344-361, vol. 57, Elsevier Masson SAS.
Ricci, M. et al., "Chemotherapeutic Approaches for Targeting Cell Death Pathways," The Oncologist, 2006, pp. 342-357, vol. 11.
Richardson, R., "Ionizing radiation and aging: rejuvenating an old idea," Aging, 2009, pp. 887-902, vol. 1.
Rockett, J. et al., "DNA arrays: technology, options and toxicological applications," Xenobiotica, 2000, pp. 155-177, vol. 30, No. 2.
Rodier, F. et al., "Four faces of cellular senescence," J. Cell Biol., Feb. 14, 2011, pp. 547-556, vol. 192, The Rockefeller University Press.
Rudin, C. et al., "Phase II Study of Single-Agent Navitoclax (ABT-263) and Biomarker Correlates in Patients with Relapsed Small Cell Lung Cancer," Clin. Cancer Res., Jun. 2012, pp. 3163-3169, vol. 18, No. 11.
Safa, A. et al., "Targeting the Anti-Apoptotic Protein c-FLIP for Cancer Therapy," Cancers, 2011, pp. 1639-1671, vol. 3.
Sanders, Y. et al., "Histone Modifications in Senescence-Associated Resistance to Apoptosis by Oxidative Stress," Redox Biol., 2013, pp. 8-16, vol. 1, Elsevier B.V.
Schimmer, A. et al., "Identification of Small Molecules that Sensitize Resistant Tumor Cells to Tumor Necrosis Factor-Family Death Receptors," Cancer Res., 2006, pp. 2367-2375, vol. 66, No. 4.
Scott, J. et al., "Searching for Peptide Ligands with an Epitope Library," Sci., Jul. 27, 1990, pp. 386-390, vol. 249, No. 4967.
Seo, Y. et al., "Synthesis and biological evaluation of piperlongumine derivatives as potent anti-inflammatory agents," Bioorg. Med. Chem. Lett., Dec. 15, 2014, pp. 5727-5730, vol. 24, No. 24, Elsevier Ltd.
Serrano, M. et al., "Oncogenic ras provokes premature cell senescence associated with accumulation of p53 and p16INK4a," Cell, 1997, pp. 593-602, vol. 88.
Serrano, M. et al., "Putting the stress on senescence," Curr. Opin. Cell Biol., 2001, pp. 748-753, vol. 13.
Shao, L. et al., "Total body irradiation causes long-term mouse BM injury via induction of HSC premature senescence in an Ink4a- and Arf-independent manner," Blood, 2014, pp. 3105-3115, vol. 123.
Shao, L. et al., "Hematopoietic stem cell injury induced by ionizing radiation," Antioxid. Redox Signal., 2014, pp. 1447-1462, vol. 20.
Shirley, S. et al., "Targeting c-FLIP in cancer," Cancer Lett., 2013, pp. 141-150, vol. 332, No. 2, Elsevier Ireland Ltd.
Siegelin, M. et al., "Genistein enhances proteasomal degradation of the short isoform of FLIP in malignant glioma cells and thereby augments TRAIL-mediated apoptosis," Neurosci. Lett., Apr. 3, 2009, pp. 92-97, vol. 453, No. 2, Elsevier Ireland Ltd.
Sorrentino, J. et al., "p16INK4a reporter mice reveal age-promoting effects of environmental toxicants," J. Clin. Invest., 2014, pp. 169-173, vol. 124.

Souers, A. et al., "ABT-199, a potent and selective BCL-2 inhibitor, achieves antitumor activity while sparing platelets," Nat. Med., 2013, pp. 202-208, vol. 19.
Tchkonia, T. et al., "Cellular senescence and the senescent secretory phenotype: therapeutic opportunities," J. Clin. Invest., 2013, pp. 966-972, vol. 123.
Tse, C. et al., "ABT-263: a potent and orally bioavailable Bcl-2 family inhibitor," Can. Res., 2008, pp. 3421-3428, vol. 68.
Van Deursen, J., "The role of senescent cells in ageing," Nature, 2014, pp. 439-446, vol. 509.
Wang, Y. et al., "Inhibition of phosphatidylinostol 3-kinase uncouples H2O2-induced senescent phenotype and cell cycle arrest in normal human diploid fibroblasts," Exp. Cell Res., 2004, pp. 188-196, vol. 298, Elsevier Inc.
Wang, Y. et al., "Total body irradiation selectively induces murine hematopoietic stem cell senescence," Blood, Jan. 1, 2006, pp. 358-366, vol. 107, No. 1.
Wang, Y. et al., "MICRORNA Regulation of Ionizing Radiation-Induced Premature Senescence," Int. J. Radiation Oncology Biol. Phys., 2011, pp. 839-848, vol. 81, No. 3, Elsevier Inc.
Wang, B. et al., "The Bcl-2/xL inhibitor ABT-263 increases the stability of Mcl-1 mRNA and protein in hepatocellular carcinoma cells," Molecular Cancer, 2014, pp. 1-11, vol. 13, No. 98.
Waring, P. et al., "Cell death induced by the Fas/Fas ligand pathway and its role in pathology," Immunology and Cell Biology, 1999, pp. 312-317, vol. 77.
Warner, H. et al., "What Does Cell Death Have to Do With Aging?," JAGS, 1997, pp. 1140-1146, vol. 45, No. 9.
Wood, T. et al., "Selective Inhibition of Histone Deacetylases Sensitizes Malignant Cells to Death Receptor Ligands," Mol. Cancer Ther., Jan. 2010, pp. 246-256, vol. 9, No. 1.
Wu, Y. et al., "Design, synthesis and biological activity of piperlongumine derivatives as selective anticancer agents," Eur. J. Med. Chem., 2014, pp. 545-551, vol. 82, Elsevier Masson SAS.
Zengerle, M. et al., "Selective Small Molecule Induced Degradation of the BET Bromodomain Protein BRD4," ACS Chem. Biol., 2015, pp. 1770-1777, vol. 10, American Chemical Society.
Zuckermann, R. et al., "Discovery of Nanomolar Ligands for 7-Transmembrane G-Protein-Coupled Receptors from a Diverse N-(Substituted)glycine Peptoid Library," J. Med. Chem., 1994, pp. 2678-2685, vol. 37.
Baar, M. et al., "Targeted Apoptosis of Senescent Cells Restores Tissue Homeostasis in Response to Chemotoxicity and Aging," HHS Public Access Author Manuscript, Mar. 23, 2018, pp. 1-37, published in final edited form as: Cell, Mar. 23, 2017, pp. 132-147, vol. 169, No. 1.
Baker, D. et al., "Naturally occurring p16Ink4a-positive cells shorten healthy lifespan," HHS Public Access Author Manuscript, Aug. 3, 2016, pp. 1-30, published in final edited form as: Nature, Feb. 11, 2016, pp. 184-189, vol. 530, No. 7589.
Blagosklonny, M., "Selective anti-cancer agents as anti-aging drugs," Cancer Biol. Ther., Dec. 2013, pp. 1092-1097, vol. 14, No. 12, Landes Bioscience.
Braun, H. et al., "Cellular Senescence Limits Regenerative Capacity and Allograft Survival," J. Am. Soc. Nephrol., Sep. 2012, pp. 1467-1473, vol. 23, No. 9.
Chen, J. et al., "The Bcl-2/Bcl-XL/Bcl-w Inhibitor, Navitoclax, Enchances the Activity of Chemotherapeutic Agents In Vitro and In Vivo," Mol. Cancer Ther., 2011, pp. 2340-2349, vol. 10, No. 12.
Childs, B. et al., "Senescent cells: an emerging target for diseases of ageing," HHS Public Access Author Manuscript, May 9, 2018, pp. 1-41, published in final edited form as: Nat. Rev. Drug Discov., Oct. 2017, pp. 718-735, vol. 16, No. 10.
International Search Report and Written Opinion dated Aug. 7, 2018 from related International Patent Application No. PCT/US2018/033479; 9 pgs.
Lin, C. et al., "Endostatin and transglutaminase 2 are involved in fibrosis of the aging kidney," HHS Public Access Author Manuscript, Jun. 1, 2017, pp. 1-20, published in final edited form as: Kidney Int., Jun. 2016, pp. 1281-1292, vol. 89, No. 6.
Liu, J. et al., "Droxinostat, a Histone Deacetylase Inhibitor, Induces Apoptosis in Hepatocellular Carcinoma Cell Lines via Activation of the Mitochondrial Pathway and Downregulation of FLIP," Trans-

(56) References Cited

OTHER PUBLICATIONS lational Oncology, Feb. 2016, pp. 70-78, vol. 9, No. 1, Elsevier Inc. on behalf of Neoplasia Press, Inc.

Matthews, C. et al., "Vascular Smooth Muscle Cells Undergo Telomere-Based Senescence in Human Atherosclerosis. Effects of Telomerase and Oxidative Stress," Cir. Res., Jul. 21, 2006, pp. 156-164, vol. 99.

Office Action dated Oct. 4, 2018 from related U.S. Appl. No. 15/545,480; 4 pgs.

Office Action dated Oct. 4, 2018 from related U.S. Appl. No. 15/308,552; 16 pgs.

Schafer, M. et al., "Targeting Senescent Cells in Fibrosis: Pathology, Paradox, and Practical Considerations," Curr. Rheumatol. Rep., Jan. 26, 2018, Article 3, vol. 20, Issue 1, SpringerLink, Abstract Only.

Son, D. et al., Piperlongumine inhibits atherosclerotic plaque formation and vascular smooth muscle cell proliferation by suppressing PDGF receptor signaling, Biochem. Biophys. Res. Commun., 2012, pp. 349-354, vol. 427.

Valentijn, F. et al., "Cellular senescence in the aging and diseased kidney," J. Cell Commun. Signal., 2018, pp. 69-82, vol. 12, Springer.

Van Willigenburg, H. et al., "Cellular senescence as a therapeutic target to improve renal transplantation outcome," Pharmacol. Res., Apr. 2018, pp. 322-330, vol. 130.

Wang, E., "Senescent Human Fibroblasts Resist Programmed Cell Death, and Failure to Suppress bcl2 is Involved," Cancer Res., Jun. 1, 1995, pp. 2284-2292, vol. 55.

Wang, Y. et al., "Total body irradiation causes residual bone marrow injury by induction of persistent oxidative stress in murine hematopoietic stem cells," Free Rad. Biol. Med., 2010, pp. 348-356, vol. 48, Elsevier Inc.

Yao, L. et al., "Piperlongumine alleviates lupus nephritis in MRL-Fas(lpr) mice by regulating the frequency of Th17 and regulatory T cells," Immunol. Lett., Sep. 2014, pp. 76-80, vol. 161, No. 1, Abstract Only.

Aguilar, A., et al., "A Potent and Highly Efficacious Bcl-2/Bcl-xL Inhibitor," J. Med. Chem., 2013, pp. 3048-3067, vol. 56.

Bai, L., et al., "BM-1197: A Novel and Specific Bcl-2/Bcl-xL Inhibitor Inducing Complete and Long-Lasting Tumor Regression In Vivo," PLOS One, Jun. 2014, pp. 1-13, vol. 9, No. 6, e99404.

Bajwa, N., et al., "Inhibitors of the anti-apoptotic Bcl-2 proteins: a patent review," NIH Public Access Author Manuscript, Jan. 17, 2013, pp. 1-25, published in final edited form as: Expert Opin. Ther. Pat., Jan. 2012, pp. 37-55, vol. 22, No. 1.

Brenkman, A. et al., "Mdm2 Induces Mono-Ubiquitination of FOXO4," PLOS One, Jul. 2008, pp. 1-7, vol. 3, No. 7, e2819.

Bruncko, M., et al., "Studies Leading to Potent, Dual Inhibitors of Bcl-2 and Bcl-xL," J. Med. Chem., 2007, pp. 641-662, vol. 50, No. 4.

Bruncko, M., et al., "Structure-Guided Design of a Series of MCL-1 Inhibitors with High Affinity and Selectivity," J. Med. Chem., 2015, pp. 2180-2194, vol. 58, No. 5.

Chang, J. et al., "Clearance of senescent cells by ABT263 rejuvenates aged hematopoietic stem cells in mice," Nat. Med., Jan. 2016, pp. 78-83, vol. 22, No. 1.

Chen, L. et al., "p53 alpha-Helix mimetics antagonize p53/MDM2 interaction and activate p53," Mol. Cancer Ther., Jun. 2005, pp. 1019-1025, vol. 4, No. 6.

Chen, J. et al., "Structure-Based Discovery of BM-957 as a Potent Small-Molecule Inhibitor of Bcl-2 and Bcl-xL Capable of Achieving Complete Tumor Regression," NIH Public Access Author Manuscript, Oct. 11, 2013, pp. 1-33, published in final edited form as: J. Med. Chem., Oct. 11, 2012, pp. 8502-8514, vol. 55, No. 19.

Delbridge, A et al., "Thirty years of BCL-2: translating cell death discoveries into novel cancer therapies," Nat. Rev. Cancer, Feb. 2016, pp. 99-109—vol. 16.

Galatin, P. et al., "A Nonpeptidic Sulfonamide Inhibits the p53-mdm2 Interaction and Activates p53-Dependent Transcription in mdm2-Overexpressing Cells," J. Med. Chem., 2004, pp. 4163-4165, vol. 47, No. 17.

Gustafson, J. et al., "Small-Molecule-Mediated Degradation of the Androgen Receptor through Hydrophobic Tagging," Angew. Chem. Int. Ed., Aug. 10, 2015, pp. 9659-9662, vol. 54, No. 33.

Lessene, G., et al., "BCL-2 family antagonists for cancer therapy," Nat. Rev. Drug Discov., Dec. 2008, pp. 989-1000, vol. 7.

Lu, Y. et al., "Discovery of a Nanomolar Inhibitor of the Human Murine Double Minute 2 (MDM2)-p53 Interaction through an Integrated, Virtual Database Screening Strategy," J. Med. Chem., 2006, pp. 3759-3762, vol. 49, No. 13.

Lu, J., et al., "Hijacking the E3 Ubiquitin Ligase Cereblon to Efficiently Target BRD4," Chem. Biol., Jun. 18, 2015, pp. 755-763, vol. 22.

Park, C-M. et al., "Discovery of an Orally Bioavailable Small Molecule Inhibitor of Prosurvival B-Cell Lymphoma 2 Proteins," J. Med. Chem., 2008, pp. 6902-6915, vol. 51, No. 21.

Pelz, N. et al., "Discovery of 2-Indole-acylsulfonamide Myeloid Cell Leukemia 1 (Mcl-1) Inhibitors Using Fragment-Based Methods," J. Med. Chem., 2016, pp. 2054-2066, vol. 59.

Sleebs, B. et al., "Quinazoline Sulfonamides as Dual Binders of the Proteins B-Cell Lymphoma 2 and B-Cell Lymphoma Extra Long with Potent Proapoptotic Cell-Based Activity," J. Med. Chem., 2011, pp. 1914-1926, vol. 54, No. 6.

Sleebs, B. et al., "Discovery of Potent and Selective Benzothiazole Hydrazone Inhibitors of Bcl-XL," J. Med. Chem., 2013, pp. 5514-5540, vol. 56, No. 13.

Stoll, R. et al., "Chalcone Derivatives Antagonize Interactions between the Human Oncoprotein MDM2 and p53," Biochem., 2001, pp. 336-344, vol. 40.

Tanaka, Y. et al., "Discovery of Potent Mcl-1/Bcl-xL Dual Inhibitors by Using a Hybridization Strategy Based on Structural Analysis of Target Proteins," J. Med. Chem., 2013, pp. 9635-9645, vol. 56, No. 23.

Tao, Z-F. et al., "Discovery of a Potent and Selective BCL-XL Inhibitor with in Vivo Activity," ACS Med. Chem. Lett., 2014, pp. 1088-1093, vol. 5.

Vogler, M. et al., "Bcl-2 inhibitors: small molecules with a big impact on cancer therapy," Cell Death Differ., 2009, pp. 360-367, vol. 16.

Vogler, M., Targeting BCL2-Proteins for the Treatment of Solid Tumours, Adv. Med., 2014, pp. 1-14, Article ID 943648, Hindawi Publishing Corporation.

Yin, H. et al., "Terphenyl-Based Helical Mimetics That Disrupt the p53/HDM2 Interaction," Angew. Chem. Int. Ed., Apr. 2005, pp. 2704-2707, vol. 44, No. 18, Wiley-VCH Verlag GmbH & Co. KGaA, Weinheim.

Zhou, H. et al., "Design of Bcl-2 and Bcl-xL Inhibitors with Subnanomolar Binding Affinities Based Upon a New Scaffold," NIH Public Access Author Manuscript, May 24, 2013, pp. 1-42, published in final edited form as: J. Med. Chem., May 24, 2012, pp. 4664-4682, vol. 55, No. 10.

Zhou, H. et al., "Structure-based Design of Potent Bcl-2/Bcl-xL Inhibitors with Strong in vivo Antitumor Activity," NIH Public Access Author Manuscript, Jul. 12, 2013, pp. 1-31, published in final edited form as: J. Med. Chem., Jul. 12, 2012, pp. 6149-6161, vol. 55, No. 13.

Zhu, Y. et al., "The Achilles' heel of senescent cells: from transcriptome to senolytic drugs," Aging Cell, Aug. 2015, pp. 644-658, vol. 14, No. 4.

Zhu, Y. et al., Identification of a novel senolytic agent, navitoclax, targeting the Bcl-2 family of anti-apoptotic factors, Aging Cell, Jun. 2016, pp. 428-435, vol. 15, No. 3.

Kirkland, J. et al., "Clinical strategies and animal models for developing senolytic agents," Exp. Gastroenterol., 2015, pp. 19-25, vol. 68, Elsevier Inc.

Office Action dated Apr. 17, 2019 from related U.S. Appl. No. 15/545,480; 15 pgs.

Tampe, D. et al., "Potential approaches to reverse or repair renal fibrosis," Nat. Rev. Nephrol., Apr. 2014, pp. 226-237, vol. 10.

International Search Report and Written Opinion dated Apr. 26, 2019 from related International Patent Application No. PCT/US2019/014545; 10 pgs.

Office Action dated May 29, 2019 from related U.S. Appl. No. 15/308,552 17 pgs.

(56) References Cited

OTHER PUBLICATIONS

Office Action dated Jun. 11, 2019 from related European Patent Application No. 15789264.7; 4 pgs.
Communication under Rule 71(e) EPC (Notice of Allowance) dated Jul. 15, 2019 from related European Patent Application No. 15789264.7; 7 pgs.
Gottlieb, Y. et al., "Physiologically aged red blood cells undergo erythrophagocytosis in vivo but not in vitro," Haematologica, 2012, pp. 994-1002, vol. 97, No. 7.
Office Action dated Oct. 16, 2019 from related U.S. Appl. No. 15/545,480; 15 pgs.
Yadav, V. et al., "Remediation of Hemorrhagic Shock-Induced Intestinal Barrier Dysfunction by Treatment with Diphenyldihaloketones EF24 and CLEFMA," J. Pharmacol. Exp. Ther., Nov. 2014, pp. 413-422, vol. 351.
Mason, K. et al., "Programmed Anuclear Cell Death Delimits Platelet Life Span," Cell, Mar. 2007, pp. 1173-1186, vol. 128.
Office Action dated Sep. 3, 2019 from related Chinese Patent Application No. 201580035221.5; 91 pgs.
Berg, C. et al., "Human mature red blood cells express caspase-3 and caspase-8, but are devoid of mitochondrial regulators of apoptosis," Cell Death and Differentiation, 2001, pp. 1197-1206, vol. 8.
Office Action dated Mar. 2, 2020 from related U.S. Appl. No. 15/545,480; 10 pgs.
Extended European Search Report dated Jul. 6, 2020 from related European Patent Application No. 19216987.8; 10 pgs.

COMPOSITIONS AND METHODS FOR SELECTIVELY DEPLETING SENESCENT CELLS

CROSS REFERENCE TO RELATED APPLICATIONS

This application is a divisional of U.S. application Ser. No. 15/328,368, filed Jan. 23, 2017, which is the national stage of International application number PCT/US2015/041470, filed Jul. 22, 2015, which claims the benefit of U.S. provisional application No. 62/027,572, filed Jul. 22, 2014, U.S. provisional application No. 62/087,499, filed Dec. 4, 2014 and U.S. provisional application No. 62/134,155, filed Mar. 17, 2015, each of the disclosures of which are hereby incorporated by reference in its entirety.

GOVERNMENTAL RIGHTS

This invention was made with government support under R01 CA122023 awarded by the National Institutes of Health. The government has certain rights in the invention.

FIELD OF THE INVENTION

The present invention relates to piperlongumine and piperlongumine derivatives and their method of use in the treatment and prevention of diseases and pathologies related to accumulation of senescent cells during aging, such as chronic obstructive pulmonary disease (COPD), osteoarthritis, atherosclerosis, neurodegenerative diseases, diabetes, and many others. The present invention also relates to pharmaceutical compositions containing these compounds as well as various uses thereof.

BACKGROUND OF THE INVENTION

Age is a leading risk factor for many human diseases, including most cancers, atherosclerosis, neurodegenerative diseases, diabetes, and many others. An increasing body of evidence demonstrates that aging is associated with an accumulation of senescent cells. When a cell becomes senescent, it loses its reproductive function, which may cause tissue degeneration. In addition, senescent cells produce increased levels of free radical and various inflammatory mediators that can induce tissue damage and cell transformation. Therefore, selective depletion of senescent cells may be a novel anti-aging strategy that may prevent various human diseases associated with aging and rejuvenate the body to live a healthier lifespan. This assumption is supported by a recent study showing that selective depletion of senescent cells in the BubR1 progeroid mouse model by a genetic approach resulted in the delay of various age-related pathologies and disorders. However, there is no drug that can selectively deplete senescent cells. Therefore, a method to selectively deplete senescent cells is needed.

BRIEF DESCRIPTION OF THE FIGURES

(FIG. 4A) Normal WI38 cells were incubated with vehicle (VEH), 1.25 µM ABT263, PL (10 uM), or both. (FIG. 4B) IR-induced senescent WI38 cells were incubated with vehicle (VEH), 1.25 µM ABT263, PL (5 or 10 uM), or both. (FIG. 4C) IR-induced senescent WI38 cells were incubated with vehicle (VEH), PL (10 uM), increasing concentrations of ABT263, or both. Cell viability was measured at 72 h and expressed as percent of control. Data are presented as mean±SE of three independent assays.

(FIG. 5A) Structure of XL-11155B. (FIG. 5B) Normal WI38 cells or (FIG. 5C) IR (10 Gy) induced senescent WI38 cells were incubated with increasing concentrations of XL-11155B. Cell viability was measured at 72 h after XL-11155B treatment and expressed as percent of control. Data are presented as mean±SE of three independent assays.

DETAILED DESCRIPTION OF THE INVENTION

Figure 1A:
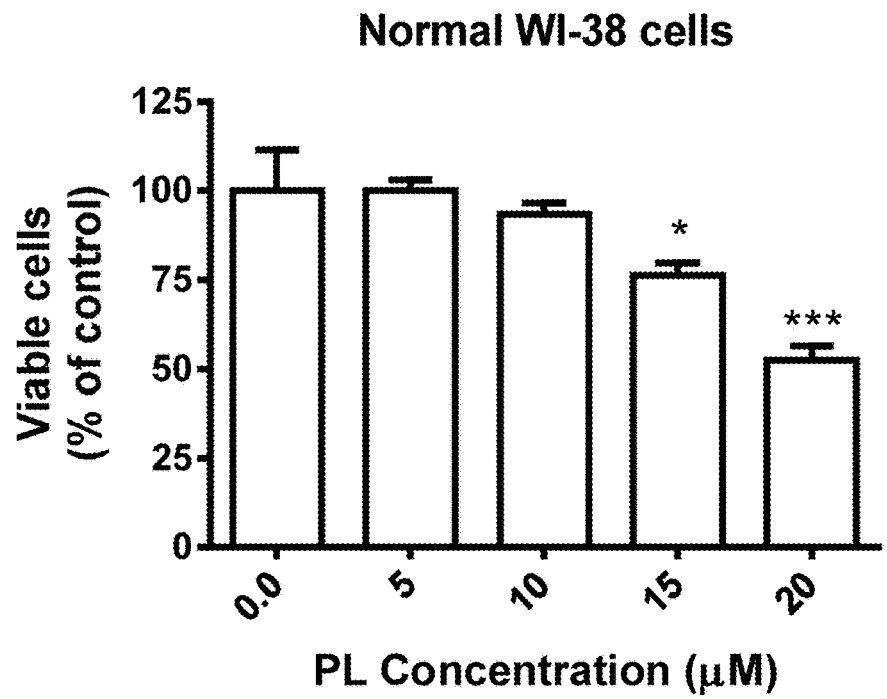
FIG. 1A-E depicts graphs showing piperlongumine (PL) selectively kills senescent WI38 cells but not normal WI38 cells in a dose- and time-dependent manner. Normal WI38 cells (FIG. 1A), ionizing radiation (IR, 10 Gy) induced senescent WI38 cells (FIG. 1B), or replicative senescent WI38 cells (FIG. 1C) were incubated with increasing concentration of PL. Cell viability was measured at 72 h after PL treatment and expressed as percent of control. Data are presented as mean±SE of three independent assays. IR-induced senescent WI38 cells were incubated with 10 uM PL and cells viability was measured 1, 3, 6, 12, 24, 48 or 72 h after the initiation of PL treatment (FIG. 1D), or the cells were incubated with 10 uM PL for various durations (1, 3, 6, 12, 24, 48 or 72 h) and cell viability was measured at 72 h (FIG. 1E). Data are presented as mean±SE of three independent assays.

Applicants have discovered that piperlongumine (PL), as well as derivatives thereof, selectively kill senescent cells. Accordingly the present disclosure provides compositions and methods for selectively depleting senescent cells. Additional aspects of the invention are described below.

I. Compositions

In an aspect, a composition of the invention comprises PL or a PL derivative. PL or PL derivatives may be modified to improve potency, bioavailability, solubility, stability, handling properties, or a combination thereof, as compared to an unmodified version. Thus, in another aspect, a composition of the invention comprises modified PL or PL derivative. In still another aspect, a composition of the invention comprises a prodrug of a PL or PL derivative.

A composition of the invention may optionally comprise one or more additional drug or therapeutically active agent in addition to the PL or PL derivative. A composition of the invention may further comprise a pharmaceutically acceptable excipient, carrier or diluent. Further, a composition of the invention may contain preserving agents, solubilizing agents, stabilizing agents, wetting agents, emulsifiers, sweeteners, colorants, odorants, salts (substances of the present invention may themselves be provided in the form of a pharmaceutically acceptable salt), buffers, coating agents or antioxidants.

Other aspects of the invention are described in further detail below.

(a) Piperlongumine (PL) and PL Derivatives

In general, the compounds detailed herein include compounds comprising a PL, or 5,6-dihydro-1-[(2E)-1-oxo-3-(3,4,5-trimethoxyphenyl)-2-propenyl]-2(1H)-pyridinone), structure as diagrammed below. PL may be isolated from a variety of *Piper* species (Piperaceae), including *Piper aborescens*, *Piper tuberculatum* and the roots of *Piper longum* L. In addition to extraction of PL from the roots of the *Piper* plant, PL can also be produced by organic synthesis (Chatterjee et al., 1967 Tetrahedron 23: 1769-1781). The crystal structure of PL and the adopted conformation of the molecule are described by Banerjee et al. (Can J. Chem 1986, 64: 867-879).

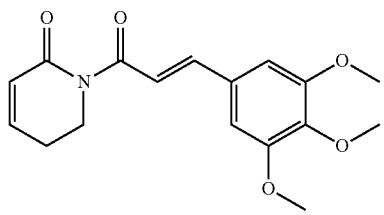 [SMILES: COc1cc(/C=C/C(=O)N2CCC=CC2=O)cc(OC)c1OC]

Provided herein are derivatives of PL. PL derivatives are modified versions of PL that are able to selectively deplete senescent cells. As used herein a "PL derivative" may be a PL derivative known in the art, a PL derivative of Formula (I) or a PL derivative of Formula (II). PL derivatives are known in the art. See for example, US 20090312373, WO 2009114126, CN 102125552, CN 102146054, CN 101774875, US 20110053938, WO 2012030408, US 20120059004, US 20120157455, US 20130237539, US 20140024639, CN 103601670, Nature 475 (2011):231-234, Eur J Med Chem 57 (2012):344-361, Tetrahedron 69 (2013): 7759-7767, PNAS 109 (2012):15115-15120, Eur J Med Chem 82 (2014):545-551, Bioorg Med Chem Lett 24 (2014):5727-5730, Journal of Asian Natural Products Research 15 (2013):658-669, each of which are incorporated herein in its entirety by reference. PL derivatives with the ability to elevate ROS in senescent cell are potentially used as senolytic drugs.

Provided herein are compounds comprising Formula (I):

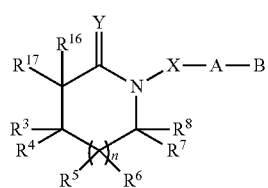

(I)

wherein:

X is selected from the group consisting of C(O), C(S), C(NH) and S(O)$_2$;

Y is selected from the group consisting of O, NH and S;

n is an integer from 0-4;

$R_3, R_4, R_5, R_6, R_7, R_8, R_{16}$ and $R_{17}$ are each independently selected from the group consisting of hydrogen, deuterium, halogen, CF$_3$, CN, OH, OCH$_3$, OR, SR, NRR, NRCOR, NRCONRR, NRCO$_2$R, COR, CO$_2$R, NOR, NO$_2$, CONRR, OC(O)NRR, SO$_2$R, SO$_2$NRR, NRSO$_2$R, NRSO$_2$NRR, C(O)C(O)R, and C(O)CH$_2$C(O)R, a substituted or unsubstituted C1 to C6 alkyl, a substituted or unsubstituted C1 to C6 alkenyl, a substituted or unsubstituted C1 to C6 alkynyl, a substituted or unsubstituted aryl, and a substituted or unsubstituted heteroaryl;

R is independently selected from the group consisting of hydrogen, substituted C1-C4 aliphatic moiety, aliphatic moiety containing nitrogen, oxygen, or sulfur, or alternately, two R moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur;

Optionally, $R_{16}$ and $R_{17}$, $R_{17}$ and $R_3$, $R_3$ and $R_4$, $R_4$ and $R_5$, $R_5$ and $R_6$, $R_6$ and $R_7$, or $R_7$ and $R_8$ are taken together to form a 4-8 membered saturated or unsaturated ring having 0-3 heteroatoms independently selected from the group consisting of nitrogen, oxygen, or sulfur;

Optionally, $R_{17}$ and $R_3$ are eliminated thereby forming a double bond between the carbons attached to $R_4$ and $R_{16}$;

A is selected from the group consisting of

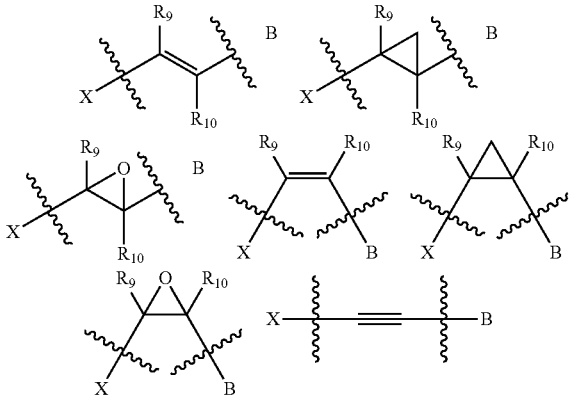

wherein:

$R_9$ and $R_{10}$ are independently selected from the group consisting of hydrogen, deuterium, halogen, CF$_3$, CN, OH, OCH$_3$, OR, SR, NRR, NRCOR, NRCONRR, NRCO$_2$R, COR, CO$_2$R, NOR, NO$_2$, CONRR, OC(O)NRR, SO$_2$R, SO$_2$NRR, NRSO$_2$R, NRSO$_2$NRR, C(O)C(O)R, and C(O)CH$_2$C(O)R, a substituted or unsubstituted C1 to C6 alkyl, a substituted or unsubstituted C1 to C6 alkenyl, a substituted or unsubstituted C1 to C6 alkynyl, a substituted or unsubstituted aryl, and a substituted or unsubstituted heteroaryl;

R is independently selected from the group consisting of hydrogen, substituted C1-C4 aliphatic moiety, aliphatic moiety containing nitrogen, oxygen, or sulfur, or alternately, two R moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur;

Optionally, $R_9$ and $R_{10}$ are taken together to form a 5-8 membered saturated or unsaturated ring having 0-3 heteroatoms independently selected from the group consisting of nitrogen, oxygen, or sulfur;

B is

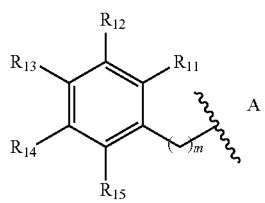

wherein:

$R_{11}$, $R_{12}$, $R_{13}$, $R_{14}$, and $R_{15}$ are each independently selected from the group consisting of hydrogen, deuterium, halogen, $CF_3$, CN, OH, $OCH_3$, OR, SR, NRR, NRCOR, NRCONRR, $NRCO_2R$, COR, $CO_2R$, NOR, $NO_2$, CONRR, OC(O)NRR, $SO_2R$, $SO_2NRR$, $NRSO_2R$, $NRSO_2NRR$, C(O)C(O)R, and $C(O)CH_2C(O)R$, a substituted or unsubstituted C1 to C6 alkyl, a substituted or unsubstituted C1 to C6 alkenyl, a substituted or unsubstituted C1 to C6 alkynyl, a substituted or unsubstituted aryl, and a substituted or unsubstituted heteroaryl;

R is independently selected from the group consisting of hydrogen, substituted C1-C4 aliphatic moiety, aliphatic moiety containing nitrogen, oxygen, or sulfur, or alternately, two R moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur;

Optionally, $R_{11}$ and $R_{12}$, $R_{12}$ and $R_{13}$, $R_{13}$ and $R_{14}$, and $R_{14}$ and $R_{15}$ are taken together to form a 4-8 membered saturated or unsaturated ring having 0-3 heteroatoms independently selected from the group consisting of nitrogen, oxygen, or sulfur;

m is an integer from 0-6;

Optionally, the phenyl ring in B can be replaced by the following one or more monocyclic aryl, one or more heteroaryl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from the group consisting of nitrogen, oxygen or sulfur, or an 8-10 membered bicyclic heteroaryl ring having 1-5 heteroatoms independently selected from the group consisting of nitrogen, oxygen, or sulfur.

In an embodiment, a compound of Formula (I) comprises any of the preceding compounds of Formula (I), wherein X is selected from the group consisting of C(O) and $S(O)_2$.

In another embodiment, a compound of Formula (I) comprises any of the preceding compounds of Formula (I), wherein Y is O.

In still another embodiment, a compound of Formula (I) comprises any of the preceding compounds of Formula (I), wherein n is an integer from 0-2.

In still yet another embodiment, a compound of Formula (I) comprises any of the preceding compounds of Formula (I), wherein $R_3$, $R_4$, $R_5$, $R_6$, $R_7$, $R_8$, $R_{16}$ and $R_{17}$ are each independently selected from the group consisting of hydrogen, SR, a substituted or unsubstituted C1 to C6 alkyl, a substituted or unsubstituted C1 to C6 alkenyl, a substituted or unsubstituted C1 to C6 alkynyl, a substituted or unsubstituted aryl, a substituted or unsubstituted heteroaryl, and $R_{17}$ and $R_3$ are eliminated thereby forming a double bond between the carbons attached to $R_4$ and $R_{16}$.

In a different embodiment, a compound of Formula (I) comprises any of the preceding compounds of Formula (I), wherein A is selected from the group consisting of

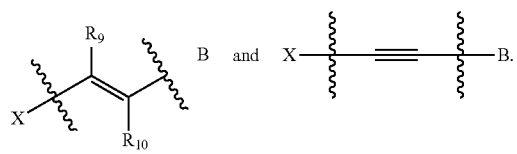

In other embodiments, a compound of Formula (I) comprises any of the preceding compounds of Formula (I), wherein $R_9$ and $R_{10}$ are independently selected from the group consisting of hydrogen, halogen, and CN.

In another embodiment, a compound of Formula (I) comprises any of the preceding compounds of Formula (I), wherein $R_{11}$, $R_{12}$, $R_{13}$, $R_{14}$, and $R_{15}$ are each independently selected from the group consisting of hydrogen, halogen, $CF_3$, OH, $OCH_3$, OR, NRR, NRCOR, $NO_2$, and a substituted or unsubstituted C1 to C6 alkyl; and R is independently selected from the group consisting of hydrogen, a substituted C1-C4 aliphatic moiety, and an aliphatic moiety containing nitrogen, oxygen, or sulfur; or the phenyl ring in B can be replaced by a 5-6 membered monocyclic heteroaryl ring having 1-4 heteroatoms independently selected from nitrogen, oxygen, or sulfur, a 7-10 membered bicyclic saturated or partially unsaturated heterocyclic ring having 1-5 heteroatoms independently selected from the group consisting of nitrogen, oxygen or sulfur, or an 8-10 membered bicyclic heteroaryl ring having 1-5 heteroatoms independently selected from the group consisting of nitrogen, oxygen, or sulfur.

In exemplary embodiments, a compound of the disclosure comprises Formula (II) as depicted in Table 2.

Also provided herein are compounds comprising Formula (II):

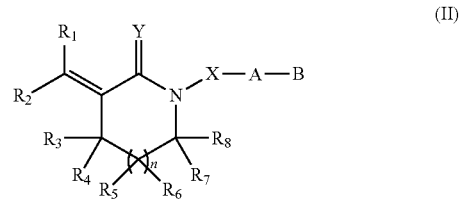

wherein:
X is selected from the group consisting of C(O), C(S), C(NH) and S(O)$_2$;
Y is selected from the group consisting of O, NH and S;
n is an integer from 0-4;
$R_1$, $R_2$, $R_3$, $R_4$, $R_5$, $R_6$, $R_7$, and $R_8$ are each independently selected from the group consisting of hydrogen, deuterium, halogen, CF$_3$, CN, OH, OCH$_3$, OR, SR, NRR, NRCOR, NRCONRR, NRCO$_2$R, COR, CO$_2$R, NOR, NO$_2$, CONRR, OC(O)NRR, SO$_2$R, SO$_2$NRR, NRSO$_2$R, NRSO$_2$NRR, C(O)C(O)R, and C(O)CH$_2$C(O)R, a substituted or unsubstituted C1 to C6 alkyl, a substituted or unsubstituted C1 to C6 alkenyl, a substituted or unsubstituted C1 to C6 alkynyl, a substituted or unsubstituted aryl, and a substituted or unsubstituted heteroaryl;
R is independently selected from the group consisting of hydrogen, substituted C1-C4 aliphatic moiety, aliphatic moiety containing nitrogen, oxygen, or sulfur, or alternately, two R moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur;
Optionally, $R_1$ and $R_2$, $R_2$ and $R_3$, $R_3$ and $R_4$, $R_4$ and $R_5$, $R_5$ and $R_6$, $R_6$ and $R_7$, or $R_7$ and $R_8$ are taken together to form a 4-8 membered saturated or unsaturated ring having 0-3 heteroatoms independently selected from the group consisting of nitrogen, oxygen, or sulfur;
A is selected from the group consisting of

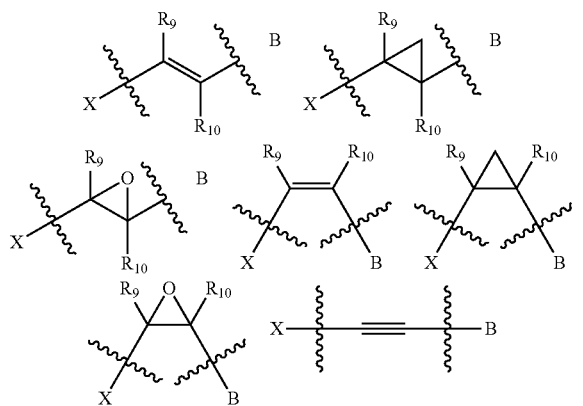

wherein:
$R_9$ and $R_{10}$ are independently selected from the group consisting of hydrogen, deuterium, halogen, CF$_3$, CN, OH, OCH$_3$, OR, SR, NRR, NRCOR, NRCONRR, NRCO$_2$R, COR, CO$_2$R, NOR, NO$_2$, CONRR, OC(O)NRR, SO$_2$R, SO$_2$NRR, NRSO$_2$R, NRSO$_2$NRR, C(O)C(O)R, and C(O)CH$_2$C(O)R, a substituted or unsubstituted C1 to C6 alkyl, a substituted or unsubstituted C1 to C6 alkenyl, a substituted or unsubstituted C1 to C6 alkynyl, a substituted or unsubstituted aryl, and a substituted or unsubstituted heteroaryl;
R is independently selected from the group consisting of hydrogen, substituted C1-C4 aliphatic moiety, aliphatic moiety containing nitrogen, oxygen, or sulfur, or alternately, two R moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur;
Optionally, $R_9$ and $R_{10}$ are taken together to form a 5-8 membered saturated or unsaturated ring having 0-3 heteroatoms independently selected from the group consisting of nitrogen, oxygen, or sulfur;
B is

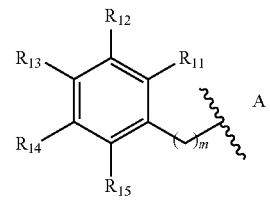

wherein:
$R_{11}$, $R_{12}$, $R_{13}$, $R_{14}$, and $R_{15}$ are each independently selected from the group consisting of hydrogen, deuterium, halogen, CF$_3$, CN, OH, OCH$_3$, OR, SR, NRR, NRCOR, NRCONRR, NRCO$_2$R, COR, CO$_2$R, NOR, NO$_2$, CONRR, OC(O)NRR, SO$_2$R, SO$_2$NRR, NRSO$_2$R, NRSO$_2$NRR, C(O)C(O)R, and C(O)CH$_2$C(O)R, a substituted or unsubstituted C1 to C6 alkyl, a substituted or unsubstituted C1 to C6 alkenyl, a substituted or unsubstituted C1 to C6 alkynyl, a substituted or unsubstituted aryl, and a substituted or unsubstituted heteroaryl;
R is independently selected from the group consisting of hydrogen, substituted C1-C4 aliphatic moiety, aliphatic moiety containing nitrogen, oxygen, or sulfur, or alternately, two R moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur;
Optionally, $R_{11}$ and $R_{12}$, $R_{12}$ and $R_{13}$, $R_{13}$ and $R_{14}$, and $R_{14}$ and $R_{15}$ are taken together to form a 4-8 membered saturated or unsaturated ring having 0-3 heteroatoms independently selected from the group consisting of nitrogen, oxygen, or sulfur;
m is an integer from 0-6;
Optionally, the phenyl ring in B can be replaced by the following one or more monocyclic aryl, one or more heteroaryl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from the group consisting of nitrogen, oxygen or sulfur, or an 8-10 membered bicyclic heteroaryl ring having 1-5 heteroatoms independently selected from the group consisting of nitrogen, oxygen, or sulfur.
In one embodiment, a compound of the disclosure comprises Formula (II), wherein: X, Y, n, $R_2$, $R_3$, $R_4$, $R_5$, $R_6$, $R_7$, $R_8$, A and B are as described above and $R_1$ is hydrogen.

In another embodiment, a compound of the disclosure comprises Formula (II), wherein: X, Y, n, $R_3$, $R_4$, $R_5$, $R_6$, $R_7$, $R_8$, A and B are as described above and $R_1$ and $R_2$ are hydrogen.

In still another embodiment, a compound of the disclosure comprises Formula (II), wherein: X, Y, n, $R_3$, $R_4$, $R_5$, $R_6$, $R_7$, $R_8$, A and B are as described above, $R_1$ is hydrogen, and $R_2$ is selected from the group consisting of a substituted or unsubstituted C1 to C6 alkyl, a substituted or unsubstituted aryl, and a substituted or unsubstituted heteroaryl.

In yet another embodiment, a compound of the disclosure comprises Formula (II), wherein: Y, n, $R_1$, $R_2$, $R_3$, $R_4$, $R_5$, $R_6$, $R_7$, $R_8$, A and B are as described above and X is selected from the group consisting of C(O) and $S(O)_2$.

In a different embodiment, a compound of the disclosure comprises Formula (II), wherein: Y, n, $R_2$, $R_3$, $R_4$, $R_5$, $R_6$, $R_7$, $R_8$, A and B are as described above, $R_1$ is hydrogen and X is selected from the group consisting of C(O) and $S(O)_2$.

In another embodiment, a compound of the disclosure comprises Formula (II), wherein: Y, n, $R_3$, $R_4$, $R_5$, $R_6$, $R_7$, $R_8$, A and B are as described above, $R_1$ and $R_2$ are hydrogen and X is selected from the group consisting of C(O) and $S(O)_2$.

In still another embodiment, a compound of the disclosure comprises Formula (II), wherein: Y, n, $R_3$, $R_4$, $R_5$, $R_6$, $R_7$, $R_8$, A and B are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl and X is selected from the group consisting of C(O) and $S(O)_2$.

In one embodiment, a compound of the disclosure comprises Formula (II), wherein: X, n, $R_1$, $R_2$, $R_3$, $R_4$, $R_5$, $R_6$, $R_7$, $R_8$, A and B are as described above and Y is O.

In one embodiment, a compound of the disclosure comprises Formula (II), wherein: X, n, $R_2$, $R_3$, $R_4$, $R_5$, $R_6$, $R_7$, $R_8$, A and B are as described above, $R_1$ is hydrogen and Y is O.

In another embodiment, a compound of the disclosure comprises Formula (II), wherein: X, n, $R_3$, $R_4$, $R_5$, $R_6$, $R_7$, $R_8$, A and B are as described above, $R_1$ and $R_2$ are hydrogen and Y is O.

In still another embodiment, a compound of the disclosure comprises Formula (II), wherein: X, n, $R_3$, $R_4$, $R_5$, $R_6$, $R_7$, $R_8$, A and B are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl and Y is O.

In one embodiment, a compound of the disclosure comprises Formula (II), wherein: n, $R_1$, $R_2$, $R_3$, $R_4$, $R_5$, $R_6$, $R_7$, $R_8$, A and B are as described above, X is selected from the group consisting of C(O) and $S(O)_2$ and Y is O.

In a different embodiment, a compound of the disclosure comprises Formula (II), wherein: n, $R_2$, $R_3$, $R_4$, $R_5$, $R_6$, $R_7$, $R_8$, A and B are as described above, $R_1$ is hydrogen, X is selected from the group consisting of C(O) and $S(O)_2$ and Y is O.

In another embodiment, a compound of the disclosure comprises Formula (II), wherein: n, $R_3$, $R_4$, $R_5$, $R_6$, $R_7$, $R_8$, A and B are as described above, $R_1$ and $R_2$ are hydrogen, X is selected from the group consisting of C(O) and $S(O)_2$ and Y is O.

In still another embodiment, a compound of the disclosure comprises Formula (II), wherein: n, $R_3$, $R_4$, $R_5$, $R_6$, $R_7$, $R_8$, A and B are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, X is selected from the group consisting of C(O) and $S(O)_2$ and Y is O.

In one embodiment, a compound of the disclosure comprises Formula (II), wherein: X, Y, $R_1$, $R_2$, $R_3$, $R_4$, $R_5$, $R_6$, $R_7$, $R_8$, A and B are as described above and n is an integer from 0-2.

In a different embodiment, a compound of the disclosure comprises Formula (II), wherein: X, Y, $R_2$, $R_3$, $R_4$, $R_5$, $R_6$, $R_7$, $R_8$, A and B are as described above, $R_1$ is hydrogen and n is an integer from 0-2.

In another embodiment, a compound of the disclosure comprises Formula (II), wherein: X, Y, $R_3$, $R_4$, $R_5$, $R_6$, $R_7$, $R_8$, A and B are as described above, $R_1$ and $R_2$ are hydrogen and n is an integer from 0-2.

In still another embodiment, a compound of the disclosure comprises Formula (II), wherein: X, Y, $R_3$, $R_4$, $R_5$, $R_6$, $R_7$, $R_8$, A and B are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl and n is an integer from 0-2.

In one embodiment, a compound of the disclosure comprises Formula (II), wherein: Y, $R_1$, $R_2$, $R_3$, $R_4$, $R_5$, $R_6$, $R_7$, $R_8$, A and B are as described above, X is selected from the group consisting of C(O) and $S(O)_2$ and n is an integer from 0-2.

In another embodiment, a compound of the disclosure comprises Formula (II), wherein: Y, $R_2$, $R_3$, $R_4$, $R_5$, $R_6$, $R_7$, $R_8$, A and B are as described above, $R_1$ is hydrogen, X is selected from the group consisting of C(O) and $S(O)_2$ and n is an integer from 0-2.

In still another embodiment, a compound of the disclosure comprises Formula (II), wherein: Y, $R_3$, $R_4$, $R_5$, $R_6$, $R_7$, $R_8$, A and B are as described above, $R_1$ and $R_2$ are hydrogen, X is selected from the group consisting of C(O) and $S(O)_2$ and n is an integer from 0-2.

In yet still another embodiment, a compound of the disclosure comprises Formula (II), wherein: Y, $R_3$, $R_4$, $R_5$, $R_6$, $R_7$, $R_8$, A and B are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, X is selected from the group consisting of C(O) and $S(O)_2$ and n is an integer from 0-2.

In one embodiment, a compound of the disclosure comprises Formula (II), wherein: X, $R_1$, $R_2$, $R_3$, $R_4$, $R_5$, $R_6$, $R_7$, $R_8$, A and B are as described above and Y is O and n is an integer from 0-2.

In a different embodiment, a compound of the disclosure comprises Formula (II), wherein: X, $R_2$, $R_3$, $R_4$, $R_5$, $R_6$, $R_7$, $R_8$, A and B are as described above, $R_1$ is hydrogen, Y is O and n is an integer from 0-2.

In another embodiment, a compound of the disclosure comprises Formula (II), wherein: X, $R_3$, $R_4$, $R_5$, $R_6$, $R_7$, $R_8$, A and B are as described above, $R_1$ and $R_2$ are hydrogen, Y is O and n is an integer from 0-2.

In still another embodiment, a compound of the disclosure comprises Formula (II), wherein: X, $R_3$, $R_4$, $R_5$, $R_6$, $R_7$, $R_8$, A and B are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, Y is O and n is an integer from 0-2.

In one embodiment, a compound of the disclosure comprises Formula (II), wherein: $R_1$, $R_2$, $R_3$, $R_4$, $R_5$, $R_6$, $R_7$, $R_8$, A and B are as described above, X is selected from the group consisting of C(O) and S(O)$_2$, Y is O and n is an integer from 0-2.

In a different embodiment, a compound of the disclosure comprises Formula (II), wherein: R$_2$, R$_3$, R$_4$, R$_5$, R$_6$, R$_7$, R$_8$, A and B are as described above, R$_1$ is hydrogen, X is selected from the group consisting of C(O) and S(O)$_2$, Y is O and n is an integer from 0-2.

In another embodiment, a compound of the disclosure comprises Formula (II), wherein: R$_3$, R$_4$, R$_5$, R$_6$, R$_7$, R$_8$, A and B are as described above, R$_1$ and R$_2$ are hydrogen, X is selected from the group consisting of C(O) and S(O)$_2$, Y is O and n is an integer from 0-2.

In still another embodiment, a compound of the disclosure comprises Formula (II), wherein: R$_3$, R$_4$, R$_5$, R$_6$, R$_7$, R$_8$, A and B are as described above, R$_1$ is hydrogen, R$_2$ is selected from the group consisting of a substituted or unsubstituted C1 to C6 alkyl, a substituted or unsubstituted aryl, and a substituted or unsubstituted heteroaryl, X is selected from the group consisting of C(O) and S(O)$_2$, Y is O and n is an integer from 0-2.

In one embodiment, a compound of the disclosure comprises Formula (II), wherein: X, Y, n, R$_1$, R$_2$, A and B are as described above and R$_3$, R$_4$, R$_5$, R$_6$, R$_7$, R$_8$ are hydrogen.

In a different embodiment, a compound of the disclosure comprises Formula (II), wherein: X, Y, n, R$_2$, A and B are as described above, R$_1$ is hydrogen and R$_3$, R$_4$, R$_5$, R$_6$, R$_7$, R$_8$ are hydrogen.

In another embodiment, a compound of the disclosure comprises Formula (II), wherein: X, Y, n, A and B are as described above, R$_1$ and R$_2$ are hydrogen and R$_3$, R$_4$, R$_5$, R$_6$, R$_7$, R$_8$ are hydrogen.

In still another embodiment, a compound of the disclosure comprises Formula (II), wherein: X, Y, n, A and B are as described above, R$_1$ is hydrogen, R$_2$ is selected from the group consisting of a substituted or unsubstituted C1 to C6 alkyl, a substituted or unsubstituted aryl, and a substituted or unsubstituted heteroaryl, and R$_3$, R$_4$, R$_5$, R$_6$, R$_7$, R$_8$ are hydrogen.

In one embodiment, a compound of the disclosure comprises Formula (II), wherein: Y, n, R$_1$, R$_2$, A and B are as described above, X is selected from the group consisting of C(O) and S(O)$_2$, and R$_3$, R$_4$, R$_5$, R$_6$, R$_7$, R$_8$ are hydrogen.

In a different embodiment, a compound of the disclosure comprises Formula (II), wherein: Y, n, R$_2$, A and B are as described above, R$_1$ is hydrogen, X is selected from the group consisting of C(O) and S(O)$_2$, and R$_3$, R$_4$, R$_5$, R$_6$, R$_7$, R$_8$ are hydrogen.

In another embodiment, a compound of the disclosure comprises Formula (II), wherein: Y, n, A and B are as described above, R$_1$ and R$_2$ are hydrogen X, is selected from the group consisting of C(O) and S(O)$_2$, and R$_3$, R$_4$, R$_5$, R$_6$, R$_7$, R$_8$ are hydrogen.

In still another embodiment, a compound of the disclosure comprises Formula (II), wherein: Y, n, A and B are as described above, R$_1$ is hydrogen, R$_2$ is selected from the group consisting of a substituted or unsubstituted C1 to C6 alkyl, a substituted or unsubstituted aryl, and a substituted or unsubstituted heteroaryl, X is selected from the group consisting of C(O) and S(O)$_2$, and R$_3$, R$_4$, R$_5$, R$_6$, R$_7$, R$_8$ are hydrogen.

In one embodiment, a compound of the disclosure comprises Formula (II), wherein: X, n, R$_1$, R$_2$, A and B are as described above, Y is O, and R$_3$, R$_4$, R$_5$, R$_6$, R$_7$, R$_8$ are hydrogen.

In a different embodiment, a compound of the disclosure comprises Formula (II), wherein: X, n, R$_2$, A and B are as described above, R$_1$ is hydrogen, Y is O, and R$_3$, R$_4$, R$_5$, R$_6$, R$_7$, R$_8$ are hydrogen.

In another embodiment, a compound of the disclosure comprises Formula (II), wherein: X, n, A and B are as described above, R$_1$ and R$_2$ are hydrogen, Y is O, and R$_3$, R$_4$, R$_5$, R$_6$, R$_7$, R$_8$ are hydrogen.

In still another embodiment, a compound of the disclosure comprises Formula (II), wherein: X, n, A and B are as described above, R$_1$ is hydrogen, R$_2$ is selected from the group consisting of a substituted or unsubstituted C1 to C6 alkyl, a substituted or unsubstituted aryl, and a substituted or unsubstituted heteroaryl, Y is O, and R$_3$, R$_4$, R$_5$, R$_6$, R$_7$, R$_8$ are hydrogen.

In one embodiment, a compound of the disclosure comprises Formula (II), wherein: n, R$_1$, R$_2$, A and B are as described above, X is selected from the group consisting of C(O) and S(O)$_2$, Y is O, and R$_3$, R$_4$, R$_5$, R$_6$, R$_7$, R$_8$ are hydrogen.

In a different embodiment, a compound of the disclosure comprises Formula (II), wherein: n, R$_2$, A and B are as described above, R$_1$ is hydrogen, X is selected from the group consisting of C(O) and S(O)$_2$, Y is O, and R$_3$, R$_4$, R$_5$, R$_6$, R$_7$, R$_8$ are hydrogen.

In another embodiment, a compound of the disclosure comprises Formula (II), wherein: n, R$_3$, R$_4$, R$_5$, R$_6$, R$_7$, R$_8$, A and B are as described above, R$_1$ and R$_2$ are hydrogen, X is selected from the group consisting of C(O) and S(O)$_2$, Y is O, and R$_3$, R$_4$, R$_5$, R$_6$, R$_7$, R$_8$ are hydrogen.

In still another embodiment, a compound of the disclosure comprises Formula (II), wherein: n, A and B are as described above, R$_1$ is hydrogen, R$_2$ is selected from the group consisting of a substituted or unsubstituted C1 to C6 alkyl, a substituted or unsubstituted aryl, and a substituted or unsubstituted heteroaryl, X is selected from the group consisting of C(O) and S(O)$_2$, Y is O, and R$_3$, R$_4$, R$_5$, R$_6$, R$_7$, R$_8$ are hydrogen.

In one embodiment, a compound of the disclosure comprises Formula (II), wherein: X, Y, R$_1$, R$_2$, A and B are as described above, n is an integer from 0-2, and R$_3$, R$_4$, R$_5$, R$_6$, R$_7$, R$_8$ are hydrogen.

In a different embodiment, a compound of the disclosure comprises Formula (II), wherein: X, Y, R$_2$, A and B are as described above, R$_1$ is hydrogen, n is an integer from 0-2, and R$_3$, R$_4$, R$_5$, R$_6$, R$_7$, R$_8$ are hydrogen.

In another embodiment, a compound of the disclosure comprises Formula (II), wherein: X, Y, A and B are as described above, R$_1$ and R$_2$ are hydrogen, n is an integer from 0-2, and R$_3$, R$_4$, R$_5$, R$_6$, R$_7$, R$_8$ are hydrogen.

In still another embodiment, a compound of the disclosure comprises Formula (II), wherein: X, Y, A and B are as described above, R$_1$ is hydrogen, R$_2$ is selected from the group consisting of a substituted or unsubstituted C1 to C6 alkyl, a substituted or unsubstituted aryl, and a substituted or unsubstituted heteroaryl, n is an integer from 0-2, and R$_3$, R$_4$, R$_5$, R$_6$, R$_7$, R$_8$ are hydrogen.

In one embodiment, a compound of the disclosure comprises Formula (II), wherein: Y, R$_1$, R$_2$, A and B are as described above, X is selected from the group consisting of C(O) and S(O)$_2$, n is an integer from 0-2, and R$_3$, R$_4$, R$_5$, R$_6$, R$_7$, R$_8$ are hydrogen.

In a different embodiment, a compound of the disclosure comprises Formula (II), wherein: Y, R$_2$, A and B are as described above, R$_1$ is hydrogen, X is selected from the group consisting of C(O) and S(O)$_2$, n is an integer from 0-2, and R$_3$, R$_4$, R$_5$, R$_6$, R$_7$, R$_8$ are hydrogen.

In another embodiment, a compound of the disclosure comprises Formula (II), wherein: Y, A and B are as described above, $R_1$ and $R_2$ are hydrogen, X is selected from the group consisting of C(O) and S(O)$_2$, n is an integer from 0-2, and $R_3$, $R_4$, $R_5$, $R_6$, $R_7$, $R_8$ are hydrogen.

In still another embodiment, a compound of the disclosure comprises Formula (II), wherein: Y, A and B are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, X is selected from the group consisting of C(O) and S(O)$_2$, n is an integer from 0-2, and $R_3$, $R_4$, $R_5$, $R_6$, $R_7$, $R_8$ are hydrogen.

In one embodiment, a compound of the disclosure comprises Formula (II), wherein: X, $R_1$, $R_2$, A and B are as described above and Y is O, n is an integer from 0-2, and $R_3$, $R_4$, $R_5$, $R_6$, $R_7$, $R_8$ are hydrogen.

In a different embodiment, a compound of the disclosure comprises Formula (II), wherein: X, $R_2$, A and B are as described above, $R_1$ is hydrogen, Y is O, n is an integer from 0-2, and $R_3$, $R_4$, $R_5$, $R_6$, $R_7$, $R_8$ are hydrogen.

In another embodiment, a compound of the disclosure comprises Formula (II), wherein: X, A and B are as described above, $R_1$ and $R_2$ are hydrogen, Y is O, n is an integer from 0-2, and $R_3$, $R_4$, $R_5$, $R_6$, $R_7$, $R_8$ are hydrogen.

In still another embodiment, a compound of the disclosure comprises Formula (II), wherein: X, A and B are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, Y is O, n is an integer from 0-2, and $R_3$, $R_4$, $R_5$, $R_6$, $R_7$, $R_8$ are hydrogen.

In one embodiment, a compound of the disclosure comprises Formula (II), wherein: $R_1$, $R_2$, A and B are as described above, X is selected from the group consisting of C(O) and S(O)$_2$, Y is O, n is an integer from 0-2, and $R_3$, $R_4$, $R_5$, $R_6$, $R_7$, $R_8$ are hydrogen.

In a different embodiment, a compound of the disclosure comprises Formula (II), wherein: $R_2$, A and B are as described above, $R_1$ is hydrogen, X is selected from the group consisting of C(O) and S(O)$_2$, Y is O, n is an integer from 0-2, and $R_3$, $R_4$, $R_5$, $R_6$, $R_7$, $R_8$ are hydrogen.

In another embodiment, a compound of the disclosure comprises Formula (II), wherein: A and B are as described above, $R_1$ and $R_2$ are hydrogen, X is selected from the group consisting of C(O) and S(O)$_2$, Y is O, n is an integer from 0-2, and $R_3$, $R_4$, $R_5$, $R_6$, $R_7$, $R_8$ are hydrogen.

In still another embodiment, a compound of the disclosure comprises Formula (II), wherein: A and B are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, X is selected from the group consisting of C(O) and S(O)$_2$, Y is O, n is an integer from 0-2, and $R_3$, $R_4$, $R_5$, $R_6$, $R_7$, $R_8$ are hydrogen.

In one embodiment, a compound of the disclosure comprises Formula (II), wherein: X, Y, n, $R_1$, $R_2$, $R_3$, $R_4$, $R_5$, $R_6$, $R_7$, $R_8$, and B are as described above and A is selected from the group consisting of

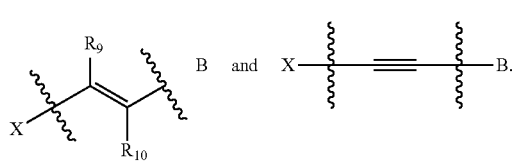

In a different embodiment, a compound of the disclosure comprises Formula (II), wherein: X, Y, n, $R_2$, $R_3$, $R_4$, $R_5$, $R_6$, $R_7$, $R_8$, and B are as described above, $R_1$ is hydrogen, and A is selected from the group consisting of

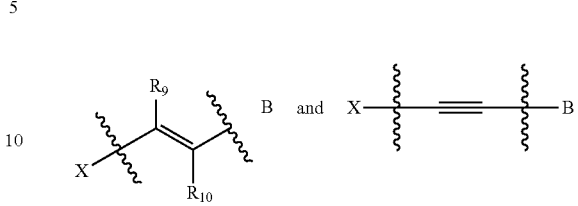

In another embodiment, a compound of the disclosure comprises Formula (II), wherein: X, Y, n, $R_3$, $R_4$, $R_5$, $R_6$, $R_7$, $R_8$, and B are as described above, $R_1$ and $R_2$ are hydrogen, and A is selected from the group consisting of

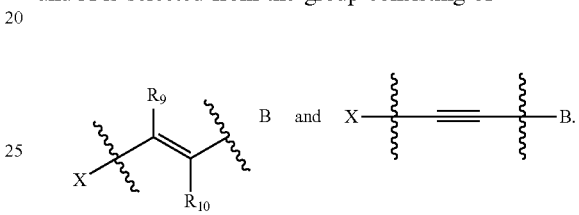

In still another embodiment, a compound of the disclosure comprises Formula (II), wherein: X, Y, n, $R_3$, $R_4$, $R_5$, $R_6$, $R_7$, $R_8$, and B are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, and A is selected from the group consisting of

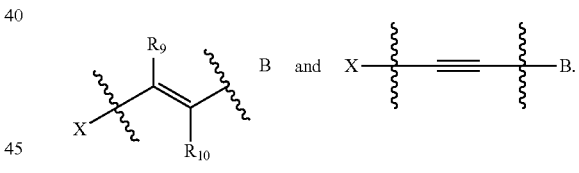

In one embodiment, a compound of the disclosure comprises Formula (II), wherein: Y, n, $R_1$, $R_2$, $R_3$, $R_4$, $R_5$, $R_6$, $R_7$, $R_8$, and B are as described above, X is selected from the group consisting of C(O) and S(O)$_2$, and A is selected from the group consisting of

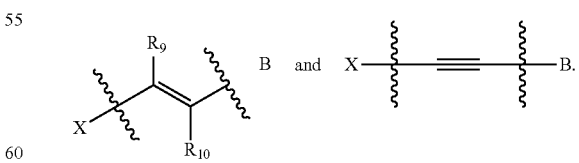

In a different embodiment, a compound of the disclosure comprises Formula (II), wherein: Y, n, $R_2$, $R_3$, $R_4$, $R_5$, $R_6$, $R_7$, $R_8$, and B are as described above, $R_1$ is hydrogen, X is selected from the group consisting of C(O) and S(O)$_2$, and A is selected from the group consisting of

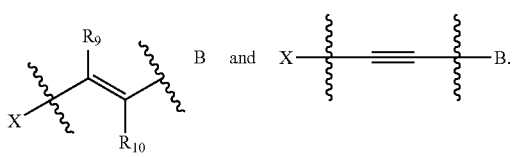 and.

In another embodiment, a compound of the disclosure comprises Formula (II), wherein: Y, n, $R_3$, $R_4$, $R_5$, $R_6$, $R_7$, $R_8$, and B are as described above, $R_1$ and $R_2$ are hydrogen, X is selected from the group consisting of C(O) and S(O)$_2$, and A is selected from the group consisting of

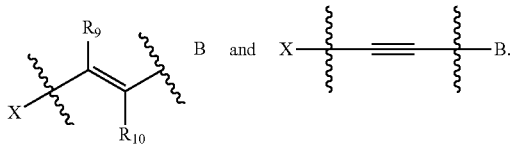 and.

In still another embodiment, a compound of the disclosure comprises Formula (II), wherein: Y, n, $R_3$, $R_4$, $R_5$, $R_6$, $R_7$, $R_8$, and B are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, X is selected from the group consisting of C(O) and S(O)$_2$, and A is selected from the group consisting of

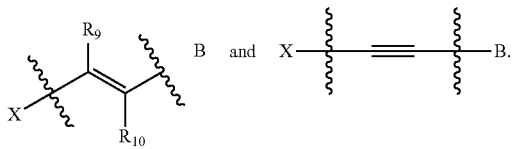 and.

In one embodiment, a compound of the disclosure comprises Formula (II), wherein: X, n, $R_1$, $R_2$, $R_3$, $R_4$, $R_5$, $R_6$, $R_7$, $R_8$, and B are as described above, Y is O, and A is selected from the group consisting of

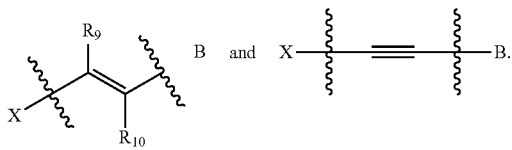 and.

In a different embodiment, a compound of the disclosure comprises Formula (II), wherein: X, n, $R_2$, $R_3$, $R_4$, $R_5$, $R_6$, $R_7$, $R_8$, and B are as described above, $R_1$ is hydrogen, Y is O, and A is selected from the group consisting of

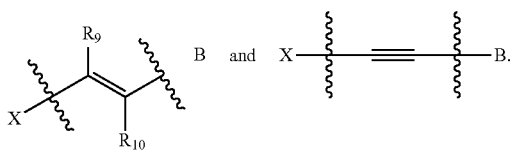 and.

In another embodiment, a compound of the disclosure comprises Formula (II), wherein: X, n, $R_3$, $R_4$, $R_5$, $R_6$, $R_7$, $R_8$, and B are as described above, $R_1$ and $R_2$ are hydrogen, Y is O, and A is selected from the group consisting of

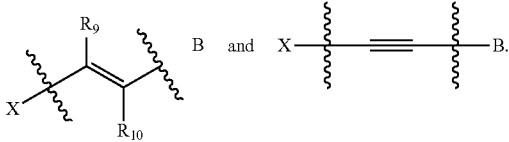 and.

In still another embodiment, a compound of the disclosure comprises Formula (II), wherein: X, n, $R_3$, $R_4$, $R_5$, $R_6$, $R_7$, $R_8$, and B are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, Y is O, and A is selected from the group consisting of

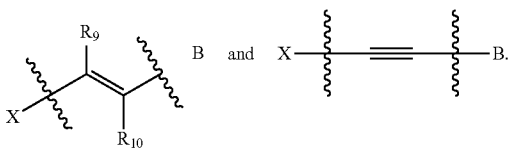 and.

In one embodiment, a compound of the disclosure comprises Formula (II), wherein: n, $R_1$, $R_2$, $R_3$, $R_4$, $R_5$, $R_6$, $R_7$, $R_8$, and B are as described above, X is selected from the group consisting of C(O) and S(O)$_2$, Y is O, and A is selected from the group consisting of

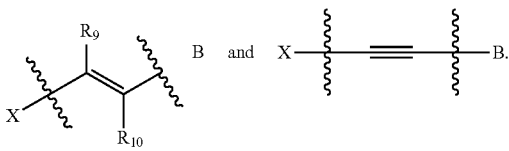 and.

In a different embodiment, a compound of the disclosure comprises Formula (II), wherein: n, $R_2$, $R_3$, $R_4$, $R_5$, $R_6$, $R_7$, $R_8$, and B are as described above, $R_1$ is hydrogen, X is selected from the group consisting of C(O) and S(O)$_2$, Y is O, and A is selected from the group consisting of

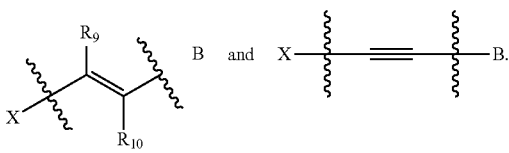 and.

In another embodiment, a compound of the disclosure comprises Formula (II), wherein: n, $R_3$, $R_4$, $R_5$, $R_6$, $R_7$, $R_8$, and B are as described above, $R_1$ and $R_2$ are hydrogen, X is selected from the group consisting of C(O) and S(O)$_2$, Y is O, and A is selected from the group consisting of

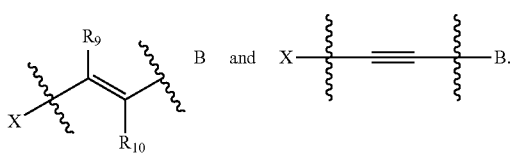

In still another embodiment, a compound of the disclosure comprises Formula (II), wherein: n, $R_3$, $R_4$, $R_5$, $R_6$, $R_7$, $R_8$, and B are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, X is selected from the group consisting of C(O) and S(O)$_2$, Y is O, and A is selected from the group consisting of

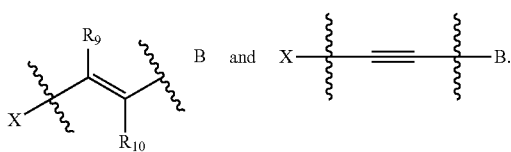

In one embodiment, a compound of the disclosure comprises Formula (II), wherein: X, Y, $R_1$, $R_2$, $R_3$, $R_4$, $R_5$, $R_6$, $R_7$, $R_8$, and B are as described above, n is an integer from 0-2, and A is selected from the group consisting of

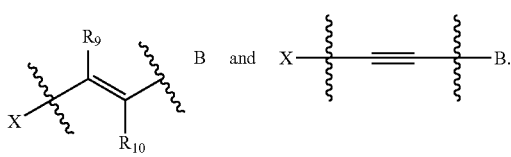

In a different embodiment, a compound of the disclosure comprises Formula (II), wherein: X, Y, $R_2$, $R_3$, $R_4$, $R_5$, $R_6$, $R_7$, $R_8$, and B are as described above, $R_1$ is hydrogen, n is an integer from 0-2, and A is selected from the group consisting of

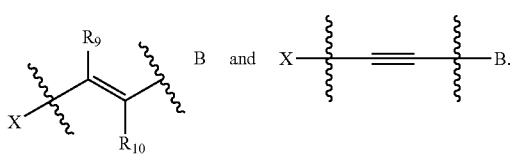

In another embodiment, a compound of the disclosure comprises Formula (II), wherein: X, Y, $R_3$, $R_4$, $R_5$, $R_6$, $R_7$, $R_8$, and B are as described above, $R_1$ and $R_2$ are hydrogen, n is an integer from 0-2, and A is selected from the group consisting of

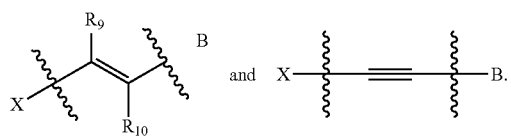

In still another embodiment, a compound of the disclosure comprises Formula (II), wherein: X, Y, $R_3$, $R_4$, $R_5$, $R_6$, $R_7$, $R_8$, and B are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, n is an integer from 0-2, and A is selected from the group consisting of

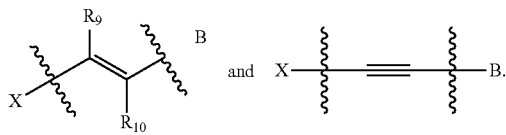

In one embodiment, a compound of the disclosure comprises Formula (II), wherein: Y, $R_1$, $R_2$, $R_3$, $R_4$, $R_5$, $R_6$, $R_7$, $R_8$, and B are as described above, X is selected from the group consisting of C(O) and S(O)$_2$, n is an integer from 0-2, and A is selected from the group consisting of

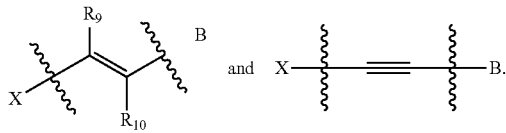

In a different embodiment, a compound of the disclosure comprises Formula (II), wherein: Y, $R_2$, $R_3$, $R_4$, $R_5$, $R_6$, $R_7$, $R_8$, and B are as described above, $R_1$ is hydrogen, X is selected from the group consisting of C(O) and S(O)$_2$, n is an integer from 0-2, and A is selected from the group consisting of

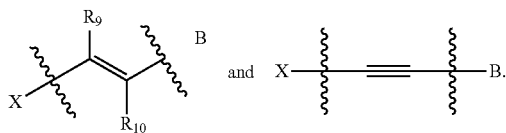

In another embodiment, a compound of the disclosure comprises Formula (II), wherein: Y, $R_3$, $R_4$, $R_5$, $R_6$, $R_7$, $R_8$, and B are as described above, $R_1$ and $R_2$ are hydrogen, X is selected from the group consisting of C(O) and S(O)$_2$, n is an integer from 0-2, and A is selected from the group consisting of

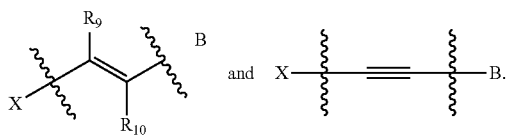

In still another embodiment, a compound of the disclosure comprises Formula (II), wherein: Y, $R_3$, $R_4$, $R_5$, $R_6$, $R_7$, $R_8$, and B are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, X is selected from the group consisting of C(O) and S(O)$_2$, n is an integer from 0-2, and A is selected from the group consisting of

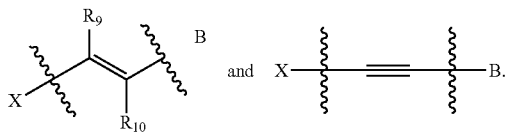

In one embodiment, a compound of the disclosure comprises Formula (II), wherein: X, $R_1$, $R_2$, $R_3$, $R_4$, $R_5$, $R_6$, $R_7$, $R_8$, and B are as described above and Y is O, n is an integer from 0-2, and A is selected from the group consisting of

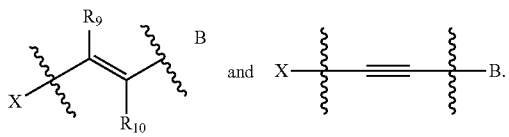

In a different embodiment, a compound of the disclosure comprises Formula (II), wherein: X, $R_2$, $R_3$, $R_4$, $R_5$, $R_6$, $R_7$, $R_8$, and B are as described above, $R_1$ is hydrogen, Y is O, n is an integer from 0-2, and A is selected from the group consisting of

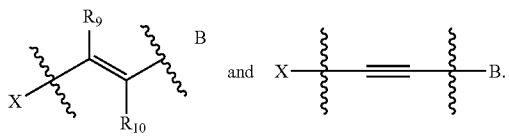

In another embodiment, a compound of the disclosure comprises Formula (II), wherein: X, $R_3$, $R_4$, $R_5$, $R_6$, $R_7$, $R_8$, and B are as described above, $R_1$ and $R_2$ are hydrogen, Y is O, n is an integer from 0-2, and A is selected from the group consisting of

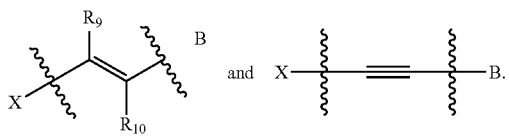

In still another embodiment, a compound of the disclosure comprises Formula (II), wherein: X, $R_3$, $R_4$, $R_5$, $R_6$, $R_7$, $R_8$, and B are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, Y is O, n is an integer from 0-2, and A is selected from the group consisting of

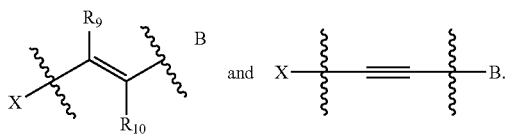

In one embodiment, a compound of the disclosure comprises Formula (II), wherein: $R_1$, $R_2$, $R_3$, $R_4$, $R_5$, $R_6$, $R_7$, $R_8$, and B are as described above, X is selected from the group consisting of C(O) and S(O)$_2$, Y is O, n is an integer from 0-2, and A is selected from the group consisting of

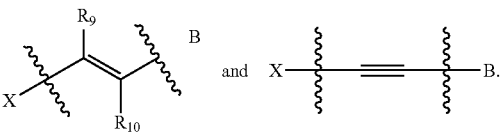

In a different embodiment, a compound of the disclosure comprises Formula (II), wherein: $R_2$, $R_3$, $R_4$, $R_5$, $R_6$, $R_7$, $R_8$, and B are as described above, $R_1$ is hydrogen, X is selected from the group consisting of C(O) and S(O)$_2$, Y is O, n is an integer from 0-2, and A is selected from the group consisting of

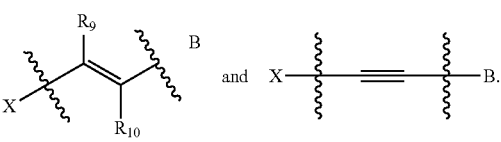

In another embodiment, a compound of the disclosure comprises Formula (II), wherein: $R_3$, $R_4$, $R_5$, $R_6$, $R_7$, $R_8$, and B are as described above, $R_1$ and $R_2$ are hydrogen, X is selected from the group consisting of C(O) and S(O)$_2$, Y is O, n is an integer from 0-2, and A is selected from the group consisting of

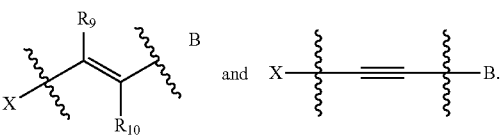

In still another embodiment, a compound of the disclosure comprises Formula (II), wherein: $R_3$, $R_4$, $R_5$, $R_6$, $R_7$, $R_8$, and B are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, X is selected from the group consisting of C(O) and S(O)$_2$, Y is O, n is an integer from 0-2, and A is selected from the group consisting of

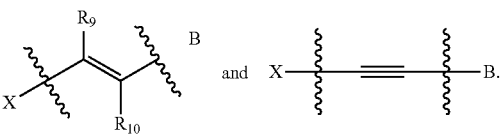

In one embodiment, a compound of the disclosure comprises Formula (II), wherein: X, Y, n, $R_1$, $R_2$, and B are as described above, $R_3$, $R_4$, $R_5$, $R_6$, $R_7$, $R_8$ are hydrogen, and A is selected from the group consisting of

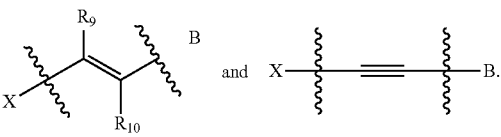

In a different embodiment, a compound of the disclosure comprises Formula (II), wherein: X, Y, n, $R_2$, and B are as described above, $R_1$ is hydrogen, $R_3$, $R_4$, $R_5$, $R_6$, $R_7$, $R_8$ are hydrogen, and A is selected from the group consisting of

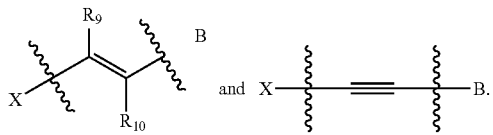

In another embodiment, a compound of the disclosure comprises Formula (II), wherein: X, Y, n, and B are as described above, $R_1$ and $R_2$ are hydrogen, $R_3$, $R_4$, $R_5$, $R_6$, $R_7$, $R_8$ are hydrogen, and A is selected from the group consisting of

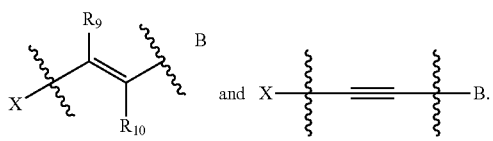

In still another embodiment, a compound of the disclosure comprises Formula (II), wherein: X, Y, n, and B are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, $R_3$, $R_4$, $R_5$, $R_6$, $R_7$, $R_8$ are hydrogen, and A is selected from the group consisting of

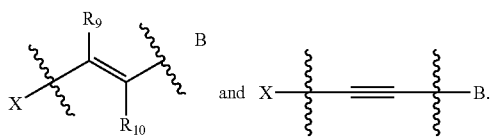

In one embodiment, a compound of the disclosure comprises Formula (II), wherein: Y, n, $R_1$, $R_2$, and B are as described above, X is selected from the group consisting of C(O) and S(O)$_2$, $R_3$, $R_4$, $R_5$, $R_6$, $R_7$, $R_8$ are hydrogen, and A is selected from the group consisting of

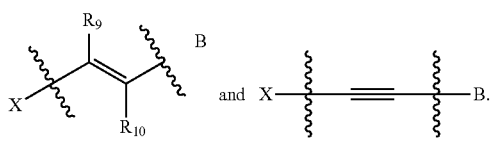

In a different embodiment, a compound of the disclosure comprises Formula (II), wherein: Y, n, $R_2$, and B are as described above, $R_1$ is hydrogen, X is selected from the group consisting of C(O) and S(O)$_2$, $R_3$, $R_4$, $R_5$, $R_6$, $R_7$, $R_8$ are hydrogen, and A is selected from the group consisting of

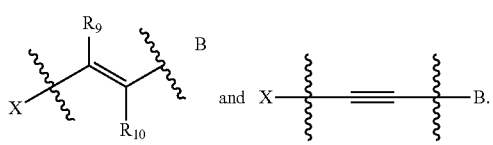

In another embodiment, a compound of the disclosure comprises Formula (II), wherein: Y, n, and B are as described above, $R_1$ and $R_2$ are hydrogen X, is selected from the group consisting of C(O) and S(O)$_2$, $R_3$, $R_4$, $R_5$, $R_6$, $R_7$, $R_8$ are hydrogen, and A is selected from the group consisting of

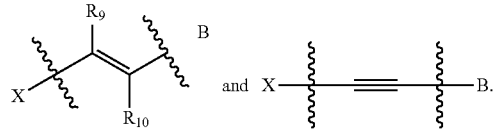

In still another embodiment, a compound of the disclosure comprises Formula (II), wherein: Y, n, and B are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, X is selected from the group consisting of C(O) and S(O)$_2$, $R_3$, $R_4$, $R_5$, $R_6$, $R_7$, $R_8$ are hydrogen, and A is selected from the group consisting of

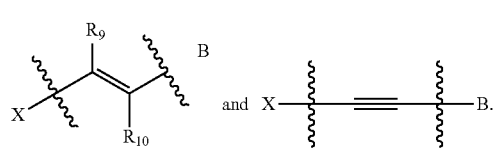

In one embodiment, a compound of the disclosure comprises Formula (II), wherein: X, n, $R_1$, $R_2$, and B are as described above, Y is O, $R_3$, $R_4$, $R_5$, $R_6$, $R_7$, $R_8$ are hydrogen, and A is selected from the group consisting of

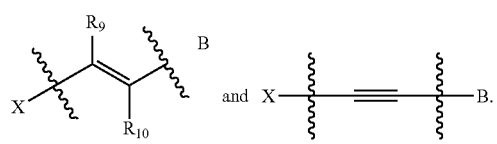

In a different embodiment, a compound of the disclosure comprises Formula (II), wherein: X, n, $R_2$, and B are as described above, $R_1$ is hydrogen, Y is O, $R_3$, $R_4$, $R_5$, $R_6$, $R_7$, $R_8$ are hydrogen, and A is selected from the group consisting of

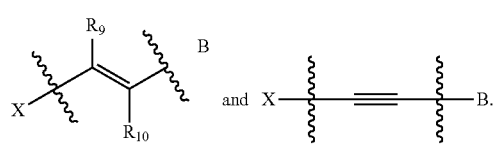

In another embodiment, a compound of the disclosure comprises Formula (II), wherein: X, n, and B are as described above, $R_1$ and $R_2$ are hydrogen, Y is O, $R_3$, $R_4$, $R_5$, $R_6$, $R_7$, $R_8$ are hydrogen, and A is selected from the group consisting of

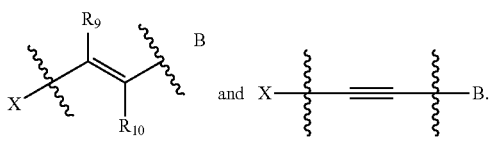

In still another embodiment, a compound of the disclosure comprises Formula (II), wherein: X, n, and B are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, Y is O, $R_3$, $R_4$, $R_5$, $R_6$, $R_7$, $R_8$ are hydrogen, and A is selected from the group consisting of

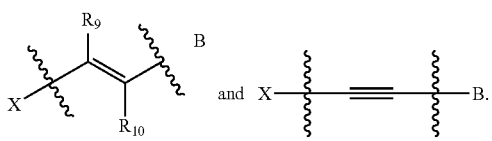

In one embodiment, a compound of the disclosure comprises Formula (II), wherein: n, $R_1$, $R_2$, and B are as described above, X is selected from the group consisting of C(O) and S(O)$_2$, Y is O, $R_3$, $R_4$, $R_5$, $R_6$, $R_7$, $R_8$ are hydrogen, and A is selected from the group consisting of

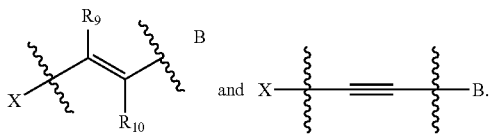

In a different embodiment, a compound of the disclosure comprises Formula (II), wherein: n, $R_2$, and B are as described above, $R_1$ is hydrogen, X is selected from the group consisting of C(O) and S(O)$_2$, Y is O, $R_3$, $R_4$, $R_5$, $R_6$, $R_7$, $R_8$ are hydrogen, and A is selected from the group consisting of

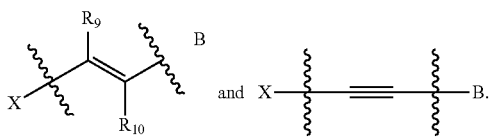

In another embodiment, a compound of the disclosure comprises Formula (II), wherein: n, $R_3$, $R_4$, $R_5$, $R_6$, $R_7$, $R_8$, and B are as described above, $R_1$ and $R_2$ are hydrogen, X is selected from the group consisting of C(O) and S(O)$_2$, Y is O, $R_3$, $R_4$, $R_5$, $R_6$, $R_7$, $R_8$ are hydrogen, and A is selected from the group consisting of

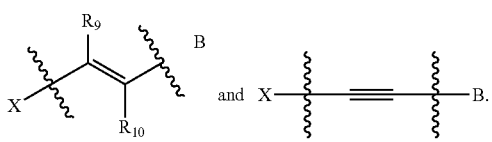

In still another embodiment, a compound of the disclosure comprises Formula (II), wherein: n, and B are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, X is selected from the group consisting of C(O) and S(O)$_2$, Y is O, $R_3$, $R_4$, $R_5$, $R_6$, $R_7$, $R_8$ are hydrogen, and A is selected from the group consisting of

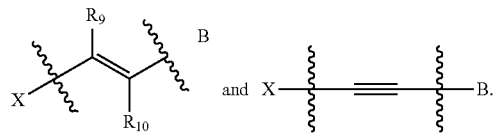

In one embodiment, a compound of the disclosure comprises Formula (II), wherein: X, Y, $R_1$, $R_2$, and B are as described above, n is an integer from 0-2, $R_3$, $R_4$, $R_5$, $R_6$, $R_7$, $R_8$ are hydrogen, and A is selected from the group consisting of

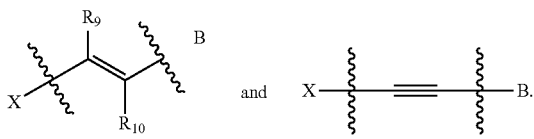

In a different embodiment, a compound of the disclosure comprises Formula (II), wherein: X, Y, $R_2$, and B are as described above, $R_1$ is hydrogen, n is an integer from 0-2, $R_3$, $R_4$, $R_5$, $R_6$, $R_7$, $R_8$ are hydrogen, and A is selected from the group consisting of

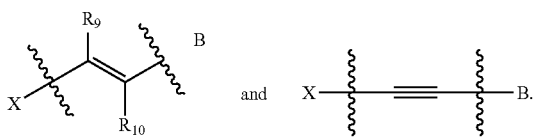

In another embodiment, a compound of the disclosure comprises Formula (II), wherein: X, Y, and B are as described above, $R_1$ and $R_2$ are hydrogen, n is an integer from 0-2, $R_3$, $R_4$, $R_5$, $R_6$, $R_7$, $R_8$ are hydrogen, and A is selected from the group consisting of

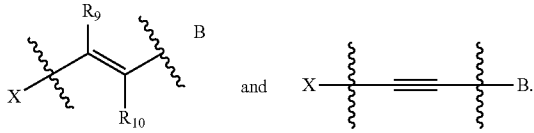

In still another embodiment, a compound of the disclosure comprises Formula (II), wherein: X, Y, and B are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, n is an integer from 0-2, $R_3$, $R_4$, $R_5$, $R_6$, $R_7$, $R_8$ are hydrogen, and A is selected from the group consisting of

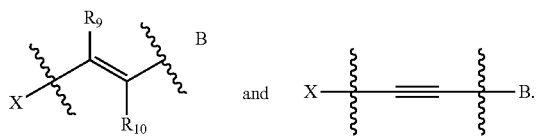 and

In one embodiment, a compound of the disclosure comprises Formula (II), wherein: Y, $R_1$, $R_2$, and B are as described above, X is selected from the group consisting of C(O) and S(O)$_2$, n is an integer from 0-2, $R_3$, $R_4$, $R_5$, $R_6$, $R_7$, $R_8$ are hydrogen, and A is selected from the group consisting of

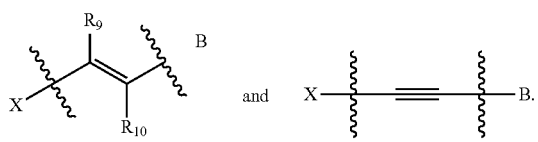 and

In a different embodiment, a compound of the disclosure comprises Formula (II), wherein: Y, $R_2$, and B are as described above, $R_1$ is hydrogen, X is selected from the group consisting of C(O) and S(O)$_2$, n is an integer from 0-2, $R_3$, $R_4$, $R_5$, $R_6$, $R_7$, $R_8$ are hydrogen, and A is selected from the group consisting of

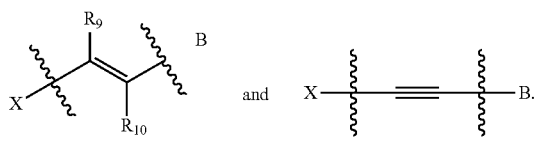 and

In another embodiment, a compound of the disclosure comprises Formula (II), wherein: Y, and B are as described above, $R_1$ and $R_2$ are hydrogen, X is selected from the group consisting of C(O) and S(O)$_2$, n is an integer from 0-2, $R_3$, $R_4$, $R_5$, $R_6$, $R_7$, $R_8$ are hydrogen, and A is selected from the group consisting of

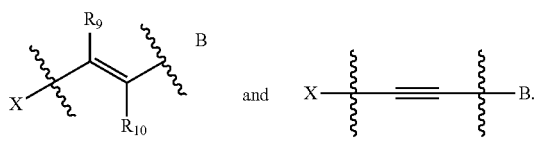 and

In still another embodiment, a compound of the disclosure comprises Formula (II), wherein: Y, and B are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, X is selected from the group consisting of C(O) and S(O)$_2$, n is an integer from 0-2, $R_3$, $R_4$, $R_5$, $R_6$, $R_7$, $R_8$ are hydrogen, and A is selected from the group consisting of

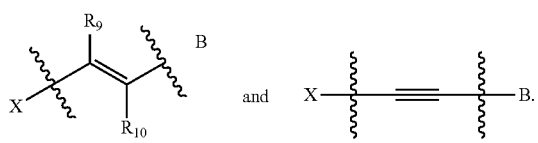 and

In one embodiment, a compound of the disclosure comprises Formula (II), wherein: X, $R_1$, $R_2$, and B are as described above and Y is O, n is an integer from 0-2, $R_3$, $R_4$, $R_5$, $R_6$, $R_7$, $R_8$ are hydrogen, and A is selected from the group consisting of

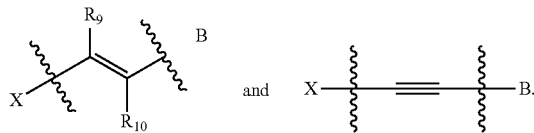 and

In a different embodiment, a compound of the disclosure comprises Formula (II), wherein: X, $R_2$, and B are as described above, $R_1$ is hydrogen, Y is O, n is an integer from 0-2, $R_3$, $R_4$, $R_5$, $R_6$, $R_7$, $R_8$ are hydrogen, and A is selected from the group consisting of

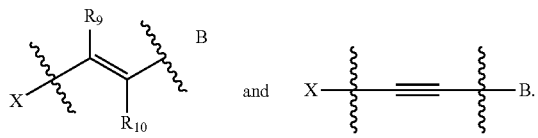 and

In another embodiment, a compound of the disclosure comprises Formula (II), wherein: X, and B are as described above, $R_1$ and $R_2$ are hydrogen, Y is O, n is an integer from 0-2, $R_3$, $R_4$, $R_5$, $R_6$, $R_7$, $R_8$ are hydrogen, and A is selected from the group consisting of

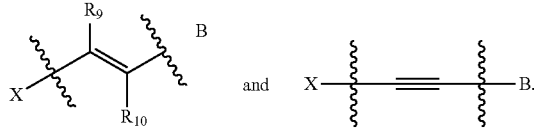 and

In still another embodiment, a compound of the disclosure comprises Formula (II), wherein: X, and B are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, Y is O, n is an integer from 0-2, $R_3$, $R_4$, $R_5$, $R_6$, $R_7$, $R_8$ are hydrogen, and A is selected from the group consisting of

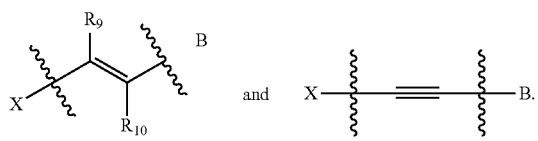 and

In one embodiment, a compound of the disclosure comprises Formula (II), wherein: $R_1$, $R_2$, and B are as described above, X is selected from the group consisting of C(O) and S(O)$_2$, Y is O, n is an integer from 0-2, $R_3$, $R_4$, $R_5$, $R_6$, $R_7$, $R_8$ are hydrogen, and A is selected from the group consisting of

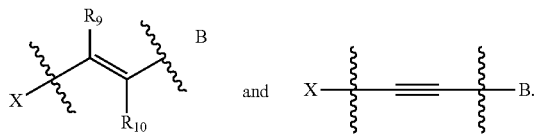

In a different embodiment, a compound of the disclosure comprises Formula (II), wherein: $R_2$, and B are as described above, $R_1$ is hydrogen, X is selected from the group consisting of C(O) and S(O)$_2$, Y is O, n is an integer from 0-2, $R_3$, $R_4$, $R_5$, $R_6$, $R_7$, $R_8$ are hydrogen, and A is selected from the group consisting of

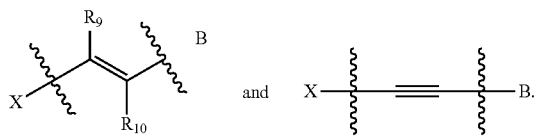

In another embodiment, a compound of the disclosure comprises Formula (II), wherein: B is as described above, $R_1$ and $R_2$ are hydrogen, X is selected from the group consisting of C(O) and S(O)$_2$, Y is O, n is an integer from 0-2, $R_3$, $R_4$, $R_5$, $R_6$, $R_7$, $R_8$ are hydrogen, and A is selected from the group consisting of

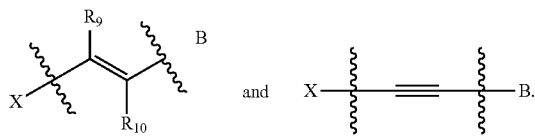

In still another embodiment, a compound of the disclosure comprises Formula (II), wherein: B is as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, X is selected from the group consisting of C(O) and S(O)$_2$, Y is O, n is an integer from 0-2, $R_3$, $R_4$, $R_5$, $R_6$, $R_7$, $R_8$ are hydrogen, and A is selected from the group consisting of

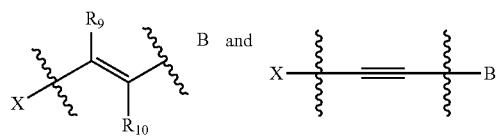

Any of the preceding compounds wherein $R_9$ and $R_{10}$ are hydrogen.

In one embodiment, a compound of the disclosure comprises Formula (II), wherein: X, Y, n, $R_1$, $R_2$, $R_3$, $R_4$, $R_5$, $R_6$, $R_7$, $R_8$, and A are as described above and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: X, Y, n, $R_2$, $R_3$, $R_4$, $R_5$, $R_6$, $R_7$, $R_8$, and A are as described above, $R_1$ is hydrogen, and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: X, Y, n, $R_3$, $R_4$, $R_5$, $R_6$, $R_7$, $R_8$, and A are as described above, $R_1$ and $R_2$ are hydrogen, and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: X, Y, n, $R_3$, $R_4$, $R_5$, $R_6$, $R_7$, $R_8$, and A are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: Y, n, $R_1$, $R_2$, $R_3$, $R_4$, $R_5$, $R_6$, $R_7$, $R_8$, and A are as described above, X is selected from the group consisting of C(O) and S(O)$_2$, and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: Y, n, $R_2$, $R_3$, $R_4$, $R_5$, $R_6$, $R_7$, $R_8$, and A are as described above, $R_1$ is hydrogen, X is selected from the group consisting of C(O) and S(O)$_2$, and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: Y, n, $R_3$, $R_4$, $R_5$, $R_6$, $R_7$, $R_8$, and A are as described above, $R_1$ and $R_2$ are hydrogen, X is selected from the group consisting of C(O) and S(O)$_2$, and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: Y, n, $R_3$, $R_4$, $R_5$, $R_6$, $R_7$, $R_8$, and A are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, X is selected from the group consisting of C(O) and S(O)$_2$, and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: X, n, $R_1$, $R_2$, $R_3$, $R_4$, $R_5$, $R_6$, $R_7$, $R_8$, and A are as described above, Y is O, and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: X, n, $R_2$, $R_3$, $R_4$, $R_5$, $R_6$, $R_7$, $R_8$, and A are as described above, $R_1$ is hydrogen, Y is O, and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: X, n, $R_3$, $R_4$, $R_5$, $R_6$, $R_7$, $R_8$, and A are as described above, $R_1$ and $R_2$ are hydrogen, Y is O, and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: X, n, $R_3$, $R_4$, $R_5$, $R_6$, $R_7$, $R_8$, and A are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, Y is O, and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: n, $R_1$, $R_2$, $R_3$, $R_4$, $R_5$, $R_6$, $R_7$, $R_8$, and A are as described above, X is selected from the group consisting of C(O) and S(O)$_2$, Y is O, and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: n, $R_2$, $R_3$, $R_4$, $R_5$, $R_6$, $R_7$, $R_8$, and A are as described above, $R_1$ is hydrogen, X is selected from the group consisting of C(O) and S(O)$_2$, Y is O, and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: n, $R_3$, $R_4$, $R_5$, $R_6$, $R_7$, $R_8$, and A are as described above, $R_1$ and $R_2$ are hydrogen, X is selected from the group consisting of C(O) and S(O)$_2$, Y is O, and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: n, $R_3$, $R_4$, $R_5$, $R_6$, $R_7$, $R_8$, and A are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, X is selected from the group consisting of C(O) and S(O)$_2$, Y is O, and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: X, Y, $R_1$, $R_2$, $R_3$, $R_4$, $R_5$, $R_6$, $R_7$, $R_8$, and A are as described above, n is an integer from 0-2, and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: X, Y, $R_2$, $R_3$, $R_4$, $R_5$, $R_6$, $R_7$, $R_8$, and A are as described above, $R_1$ is hydrogen, n is an integer from 0-2, and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: X, Y, $R_3$, $R_4$, $R_5$, $R_6$, $R_7$, $R_8$, and A are as described above, $R_1$ and $R_2$ are hydrogen, n is an integer from 0-2, B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: X, Y, $R_3$, $R_4$, $R_5$, $R_6$, $R_7$, $R_8$, and A are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, n is an integer from 0-2, and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: Y, $R_1$, $R_2$, $R_3$, $R_4$, $R_5$, $R_6$, $R_7$, $R_8$, and A are as described above, X is selected from the group consisting of C(O) and S(O)$_2$, n is an integer from 0-2, and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: Y, $R_2$, $R_3$, $R_4$, $R_5$, $R_6$, $R_7$, $R_8$, and A are as described above, $R_1$ is hydrogen, X is selected from the group consisting of C(O) and S(O)$_2$, n is an integer from 0-2, and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: Y, $R_3$, $R_4$, $R_5$, $R_6$, $R_7$, $R_8$, and A are as described above, $R_1$ and $R_2$ are hydrogen, X is selected from the group consisting of C(O) and S(O)$_2$, n is an integer from 0-2, and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: Y, $R_3$, $R_4$, $R_5$, $R_6$, $R_7$, $R_8$, and A are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, X is selected from the group consisting of C(O) and S(O)$_2$, n is an integer from 0-2, and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: X, $R_1$, $R_2$, $R_3$, $R_4$, $R_5$, $R_6$, $R_7$, $R_8$, and A are as described above and Y is O, n is an integer from 0-2, and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: X, $R_2$, $R_3$, $R_4$, $R_5$, $R_6$, $R_7$, $R_8$, and A are as described above, $R_1$ is hydrogen, Y is O, n is an integer from 0-2, and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: X, $R_3$, $R_4$, $R_5$, $R_6$, $R_7$, $R_8$, and A are as described above, $R_1$ and $R_2$ are hydrogen, Y is O, n is an integer from 0-2, and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: X, $R_3$, $R_4$, $R_5$, $R_6$, $R_7$, $R_8$, and A are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, Y is O, n is an integer from 0-2, and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: $R_1$, $R_2$, $R_3$, $R_4$, $R_5$, $R_6$, $R_7$, $R_8$, and A are as described above, X is selected from the group consisting of C(O) and S(O)$_2$, Y is O, n is an integer from 0-2, and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: $R_2$, $R_3$, $R_4$, $R_5$, $R_6$, $R_7$, $R_8$, and A are as described above, $R_1$ is hydrogen, X is selected from the group consisting of C(O) and S(O)$_2$, Y is O, n is an integer from 0-2, and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: $R_3$, $R_4$, $R_5$, $R_6$, $R_7$, $R_8$, and A are as described above, $R_1$ and $R_2$ are hydrogen, X is selected from the group consisting of C(O) and S(O)$_2$, Y is O, n is an integer from 0-2, and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: $R_3$, $R_4$, $R_5$, $R_6$, $R_7$, $R_8$, and A are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, X is selected from the group consisting of C(O) and S(O)$_2$, Y is O, n is an integer from 0-2, and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: X, Y, n, $R_1$, $R_2$, and A are as described above, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: X, Y, n, $R_2$, and A are as described above, $R_1$ is hydrogen, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: X, Y, n, and A are as described above, $R_1$ and $R_2$ are hydrogen, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: X, Y, n, and A are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: Y, n, $R_1$, $R_2$, and A are as described above, X is selected from the group consisting of C(O) and S(O)$_2$, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: Y, n, $R_2$, and A are as described above, $R_1$ is hydrogen, X is selected from the group consisting of C(O) and S(O)$_2$, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: Y, n, and A are as described above, $R_1$ and $R_2$ are hydrogen X, is selected from the group consisting of C(O) and S(O)$_2$, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: Y, n, and A are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, X is selected from the group consisting of C(O) and S(O)$_2$, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: X, n, $R_1$, $R_2$, and A are as described above, Y is O, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: X, n, $R_2$, and A are as described above, $R_1$ is hydrogen, Y is O, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: X, n, and A are as described above, $R_1$ and $R_2$ are hydrogen, Y is O, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: X, n, and A are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, Y is O, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: n, $R_1$, $R_2$, and A are as described above, X is selected from the group consisting of C(O) and S(O)$_2$, Y is O, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: n, $R_2$, and A are as described above, $R_1$ is hydrogen, X is selected from the group consisting of C(O) and S(O)$_2$, Y is O, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: n, $R_3$, $R_4$, $R_5$, $R_6$, $R_7$, $R_8$, and A are as described above, $R_1$ and $R_2$ are hydrogen, X is selected from the group consisting of C(O) and S(O)$_2$, Y is O, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: n, and A are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, X is selected from the group consisting of C(O) and S(O)$_2$, Y is O, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: X, Y, $R_1$, $R_2$, and A are as described above, n is an integer from 0-2, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: X, Y, $R_2$, and A are as described above, $R_1$ is hydrogen, n is an integer from 0-2, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: X, Y, and A are as described above, $R_1$ and $R_2$ are hydrogen, n is an integer from 0-2, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: X, Y, and A are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, n is an integer from 0-2, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: Y, $R_1$, $R_2$, and A are as described above, X is selected from the group consisting of C(O) and S(O)$_2$, n is an integer from 0-2, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: Y, $R_2$, and A are as described above, $R_1$ is hydrogen, X is selected from the group consisting of C(O) and S(O)$_2$, n is an integer from 0-2, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: Y, and A are as described above, $R_1$ and $R_2$ are hydrogen, X is selected from the group consisting of C(O) and S(O)$_2$, n is an integer from 0-2, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: Y, and A are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, X is selected from the group consisting of C(O) and S(O)$_2$, n is an integer from 0-2, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: X, $R_1$, $R_2$, and A are as described above and Y is O, n is an integer from 0-2, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: X, $R_2$, and A are as described above, $R_1$ is hydrogen, Y is O, n is an integer from 0-2, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: X, and A are as described above, $R_1$ and $R_2$ are hydrogen, Y is O, n is an integer from 0-2, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: X, and A are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, Y is O, n is an integer from 0-2, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: $R_1$, $R_2$, and A are as described above, X is selected from the group consisting of C(O) and S(O)$_2$, Y is O, n is an integer from 0-2, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: $R_2$, and A are as described above, $R_1$ is hydrogen, X is selected from the group consisting of C(O) and S(O)$_2$, Y is O, n is an integer from 0-2, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: A is as described above, $R_1$ and $R_2$ are hydrogen, X is selected from the group consisting of C(O) and S(O)$_2$, Y is O, n is an integer from 0-2, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: A is as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, X is selected from the group consisting of C(O) and S(O)$_2$, Y is O, n is an integer from 0-2, $R_3$, $R_4$, $R_5$, $R_6$, $R_7$, $R_8$ are hydrogen, and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: X, Y, n, $R_1$, $R_2$, $R_3$, $R_4$, $R_5$, $R_6$, $R_7$, and $R_8$ are as described above, A is selected from the group consisting of and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: X, Y, n, $R_2$, $R_3$, $R_4$, $R_5$, $R_6$, $R_7$, and $R_8$ are as described above, $R_1$ is hydrogen, A is selected from the group consisting of

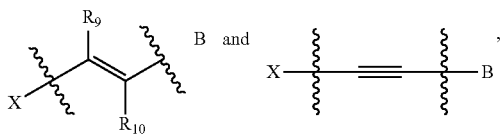

and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: X, Y, n, $R_3$, $R_4$, $R_5$, $R_6$, $R_7$, and $R_8$ are as described above, $R_1$ and $R_2$ are hydrogen, A is selected from the group consisting of

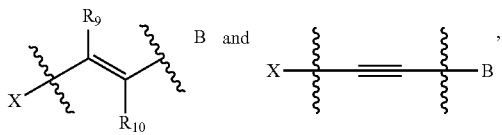

and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: X, Y, n, $R_3$, $R_4$, $R_5$, $R_6$, $R_7$, and $R_8$ are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, A is selected from the group consisting of

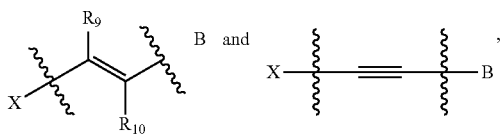

and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: Y, n, $R_1$, $R_2$, $R_3$, $R_4$, $R_5$, $R_6$, $R_7$, and $R_8$ are as described above, X is selected from the group consisting of C(O) and S(O)$_2$, A is selected from the group consisting of

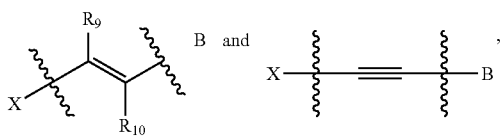

and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: Y, n, $R_2$, $R_3$, $R_4$, $R_5$, $R_6$, $R_7$, and $R_8$ are as described above, $R_1$ is hydrogen, X is selected from the group consisting of C(O) and S(O)$_2$, A is selected from the group consisting of

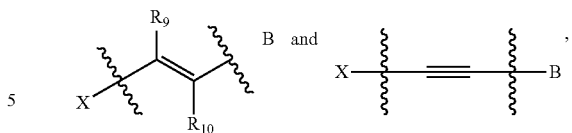

and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: Y, n, $R_3$, $R_4$, $R_5$, $R_6$, $R_7$, and $R_8$ are as described above, $R_1$ and $R_2$ are hydrogen, X is selected from the group consisting of C(O) and S(O)$_2$, A is selected from the group consisting of

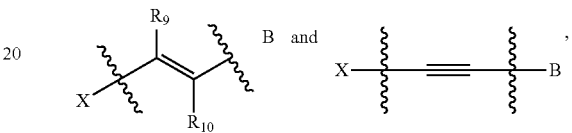

and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: Y, n, $R_3$, $R_4$, $R_5$, $R_6$, $R_7$, and $R_8$ are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, X is selected from the group consisting of C(O) and S(O)$_2$, A is selected from the group consisting of

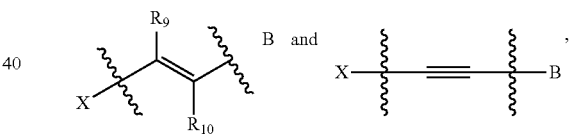

and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: X, n, $R_1$, $R_2$, $R_3$, $R_4$, $R_5$, $R_6$, $R_7$, and $R_8$ are as described above, Y is O, A is selected from the group consisting of

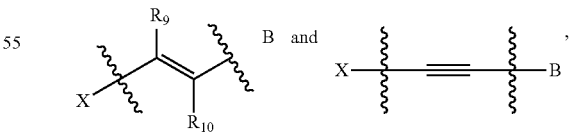

and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: X, n, $R_2$, $R_3$, $R_4$, $R_5$, $R_6$, $R_7$, and $R_8$ are as described above, $R_1$ is hydrogen, Y is O, A is selected from the group consisting of

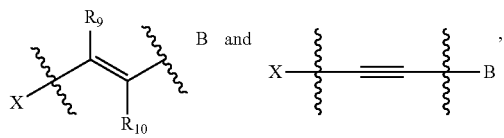

and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: X, n, $R_3$, $R_4$, $R_5$, $R_6$, $R_7$, and $R_8$ are as described above, $R_1$ and $R_2$ are hydrogen, Y is O, A is selected from the group consisting of

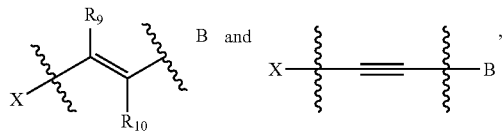

and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: X, n, $R_3$, $R_4$, $R_5$, $R_6$, $R_7$, and $R_8$ are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, Y is O, A is selected from the group consisting of

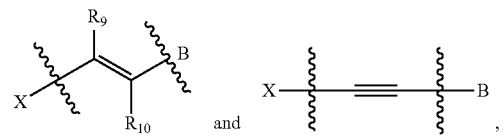

and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: n, $R_1$, $R_2$, $R_3$, $R_4$, $R_5$, $R_6$, $R_7$, and $R_8$ are as described above, X is selected from the group consisting of C(O) and $S(O)_2$, Y is O, A is selected from the group consisting of

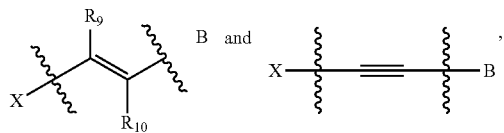

and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: n, $R_2$, $R_3$, $R_4$, $R_5$, $R_6$, $R_7$, and $R_8$ are as described above, $R_1$ is hydrogen, X is selected from the group consisting of C(O) and $S(O)_2$, Y is O, A is selected from the group consisting of

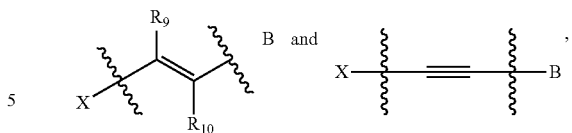

and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: n, $R_3$, $R_4$, $R_5$, $R_6$, $R_7$, and $R_8$ are as described above, $R_1$ and $R_2$ are hydrogen, X is selected from the group consisting of C(O) and $S(O)_2$, Y is O, A is selected from the group consisting of

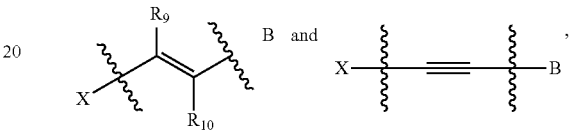

and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: n, $R_3$, $R_4$, $R_5$, $R_6$, $R_7$, and $R_8$ are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, X is selected from the group consisting of C(O) and $S(O)_2$, Y is O, A is selected from the group consisting of

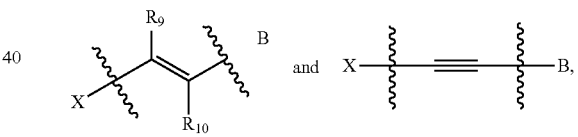

and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: X, Y, $R_1$, $R_2$, $R_3$, $R_4$, $R_5$, $R_6$, $R_7$, and $R_8$ are as described above, n is an integer from 0-2, A is selected from the group consisting of

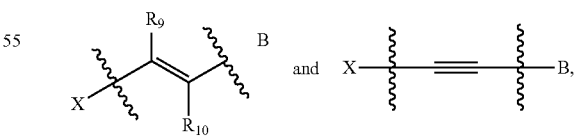

and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: X, Y, $R_2$, $R_3$, $R_4$, $R_5$, $R_6$, $R_7$, and $R_8$ are as described above, $R_1$ is hydrogen, n is an integer from 0-2, A is selected from the group consisting of

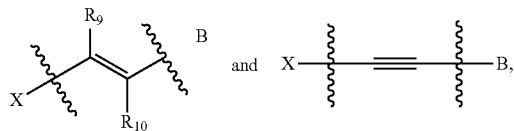 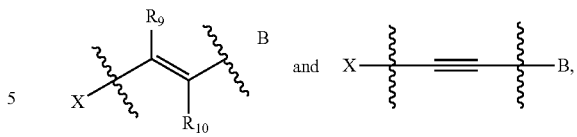

and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: X, Y, $R_3$, $R_4$, $R_5$, $R_6$, $R_7$, and $R_8$ are as described above, $R_1$ and $R_2$ are hydrogen, n is an integer from 0-2, A is selected from the group consisting of

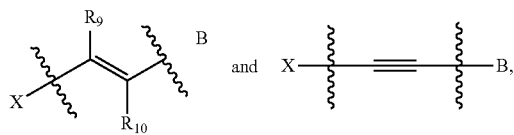

and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: X, Y, $R_3$, $R_4$, $R_5$, $R_6$, $R_7$, and $R_8$ are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, n is an integer from 0-2, A is selected from the group consisting of

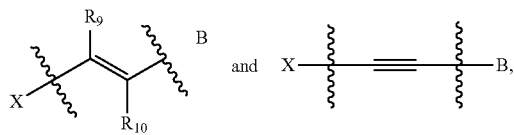

and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: Y, $R_1$, $R_2$, $R_3$, $R_4$, $R_5$, $R_6$, $R_7$, and $R_8$ are as described above, X is selected from the group consisting of C(O) and S(O)$_2$, n is an integer from 0-2, A is selected from the group consisting of

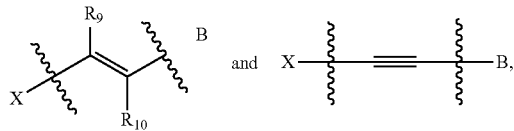

and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: Y, $R_2$, $R_3$, $R_4$, $R_5$, $R_6$, $R_7$, and $R_8$ are as described above, $R_1$ is hydrogen, X is selected from the group consisting of C(O) and S(O)$_2$, n is an integer from 0-2, A is selected from the group consisting of and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: Y, $R_3$, $R_4$, $R_5$, $R_6$, $R_7$, and $R_8$ are as described above, $R_1$ and $R_2$ are hydrogen, X is selected from the group consisting of C(O) and S(O)$_2$, n is an integer from 0-2, A is selected from the group consisting of

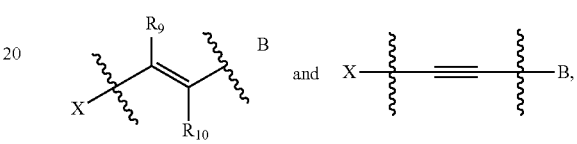

and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: Y, $R_3$, $R_4$, $R_5$, $R_6$, $R_7$, and $R_8$ are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, X is selected from the group consisting of C(O) and S(O)$_2$, n is an integer from 0-2, A is selected from the group consisting of

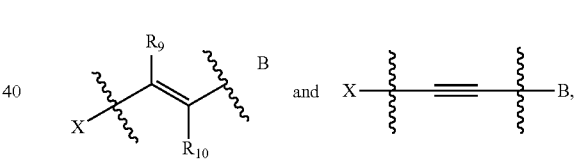

and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: X, $R_1$, $R_2$, $R_3$, $R_4$, $R_5$, $R_6$, $R_7$, and $R_8$ are as described above and Y is O, n is an integer from 0-2, A is selected from the group consisting of

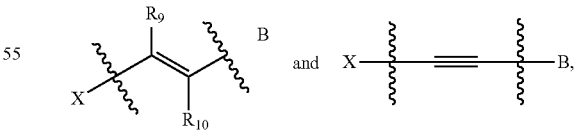

and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: X, $R_2$, $R_3$, $R_4$, $R_5$, $R_6$, $R_7$, and $R_8$ are as described above, $R_1$ is hydrogen, Y is O, n is an integer from 0-2, A is selected from the group consisting of

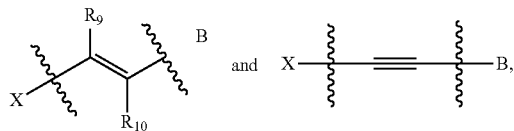

and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: X, $R_3$, $R_4$, $R_5$, $R_6$, $R_7$, and $R_8$ are as described above, $R_1$ and $R_2$ are hydrogen, Y is O, n is an integer from 0-2, A is selected from the group consisting of

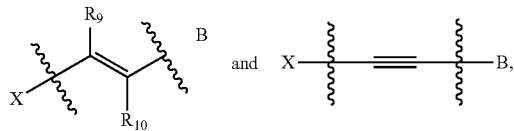

and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: X, $R_3$, $R_4$, $R_5$, $R_6$, $R_7$, and $R_8$ are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, Y is O, n is an integer from 0-2, A is selected from the group consisting of

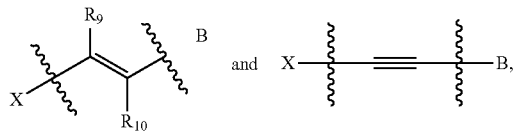

and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: $R_1$, $R_2$, $R_3$, $R_4$, $R_5$, $R_6$, $R_7$, and $R_8$ are as described above, X is selected from the group consisting of C(O) and S(O)$_2$, Y is O, n is an integer from 0-2, A is selected from the group consisting of

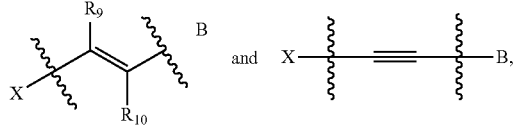

and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: $R_2$, $R_3$, $R_4$, $R_5$, $R_6$, $R_7$, and $R_8$ are as described above, $R_1$ is hydrogen, X is selected from the group consisting of C(O) and S(O)$_2$, Y is O, n is an integer from 0-2, A is selected from the group consisting of

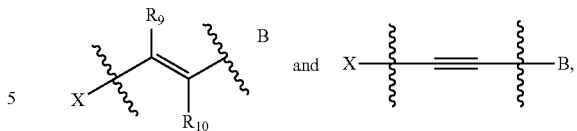

and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: $R_3$, $R_4$, $R_5$, $R_6$, $R_7$, and $R_8$ are as described above, $R_1$ and $R_2$ are hydrogen, X is selected from the group consisting of C(O) and S(O)$_2$, Y is O, n is an integer from 0-2, A is selected from the group consisting of

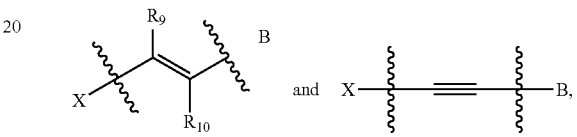

and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: $R_3$, $R_4$, $R_5$, $R_6$, $R_7$, and $R_8$ are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, X is selected from the group consisting of C(O) and S(O)$_2$, Y is O, n is an integer from 0-2, A is selected from the group consisting of

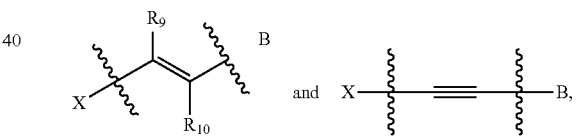

and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: X, Y, n, $R_1$, and $R_2$ are as described above, $R_3$, $R_4$, $R_5$, $R_6$, $R_7$, $R_8$ are hydrogen, A is selected from the group consisting of

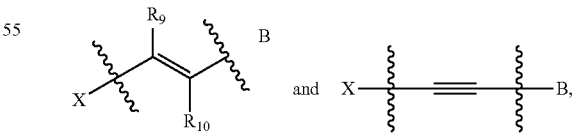

and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: X, Y, n, and $R_2$ are as described above, $R_1$ is hydrogen, $R_3$, $R_4$, $R_5$, $R_6$, $R_7$, $R_8$ hydrogen, A is selected from the group consisting of

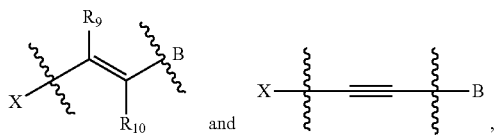

and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: X, Y, and n are as described above, $R_1$ and $R_2$ are hydrogen, $R_3$, $R_4$, $R_5$, $R_6$, $R_7$, $R_8$ are hydrogen, A is selected from the group consisting of

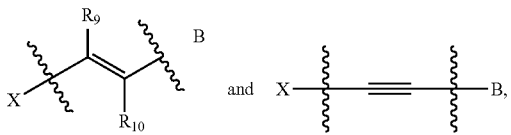

and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: X, Y, and n are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, $R_3$, $R_4$, $R_5$, $R_6$, $R_7$, $R_8$ are hydrogen, A is selected from the group consisting of

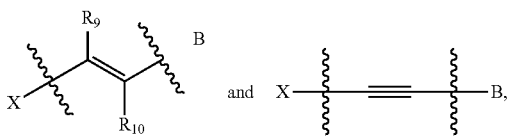

and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: Y, n, $R_1$, and $R_2$ are as described above, X is selected from the group consisting of C(O) and S(O)$_2$, $R_3$, $R_4$, $R_5$, $R_6$, $R_7$, $R_8$ are hydrogen, A is selected from the group consisting of

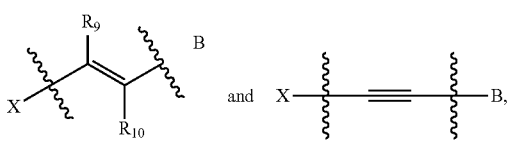

and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: Y, n, and $R_2$ are as described above, $R_1$ is hydrogen, X is selected from the group consisting of C(O) and S(O)$_2$, $R_3$, $R_4$, $R_5$, $R_6$, $R_7$, $R_8$ are hydrogen, A is selected from the group consisting of

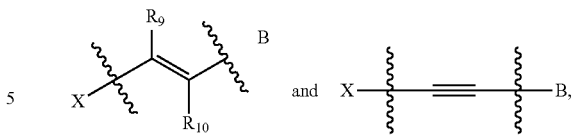

and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: Y, and n are as described above, $R_1$ and $R_2$ are hydrogen X, is selected from the group consisting of C(O) and S(O)$_2$, $R_3$, $R_4$, $R_5$, $R_6$, $R_7$, $R_8$ are hydrogen, A is selected from the group consisting of

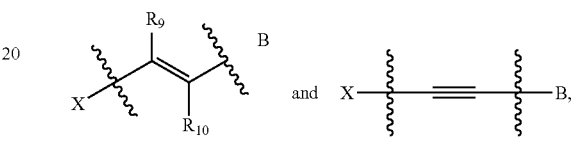

and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: Y, and n are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, X is selected from the group consisting of C(O) and S(O)$_2$, $R_3$, $R_4$, $R_5$, $R_6$, $R_7$, $R_8$ are hydrogen, A is selected from the group consisting of

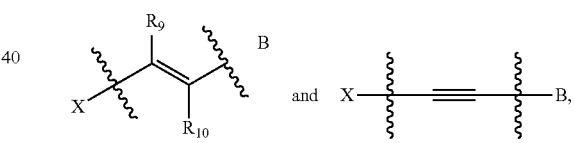

and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: X, n, $R_1$, and $R_2$ are as described above, Y is O, $R_3$, $R_4$, $R_5$, $R_6$, $R_7$, $R_8$ are hydrogen, A is selected from the group consisting of

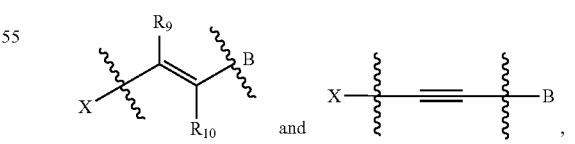

and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: X, n, and $R_2$ are as described above, $R_1$ is hydrogen, Y is O, $R_3$, $R_4$, $R_5$, $R_6$, $R_7$, $R_8$ are hydrogen, A is selected from the group consisting of

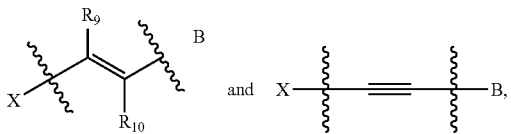

and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: X, and n are as described above, $R_1$ and $R_2$ are hydrogen, Y is O, $R_3$, $R_4$, $R_5$, $R_6$, $R_7$, $R_8$ are hydrogen, A is selected from the group consisting of

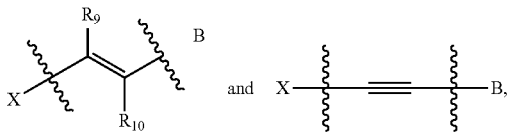

and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: X, and n are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, Y is O, $R_3$, $R_4$, $R_5$, $R_6$, $R_7$, $R_8$ are hydrogen, A is selected from the group consisting of

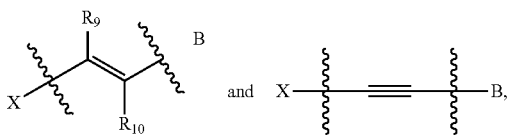

and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: n, $R_1$, and $R_2$ are as described above, X is selected from the group consisting of C(O) and S(O)$_2$, Y is O, $R_3$, $R_4$, $R_5$, $R_6$, $R_7$, $R_8$ are hydrogen, A is selected from the group consisting of

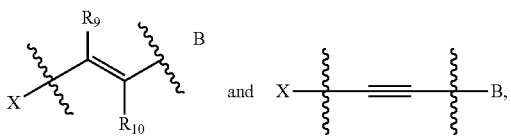

and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: n, and $R_2$ are as described above, $R_1$ is hydrogen, X is selected from the group consisting of C(O) and S(O)$_2$, Y is O, $R_3$, $R_4$, $R_5$, $R_6$, $R_7$, $R_8$ are hydrogen, A is selected from the group consisting of

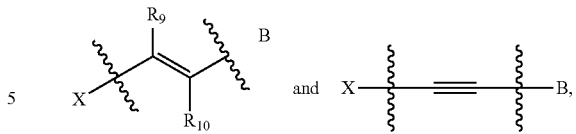

and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: n, $R_3$, $R_4$, $R_5$, $R_6$, $R_7$, and $R_8$ are as described above, $R_1$ and $R_2$ are hydrogen, X is selected from the group consisting of C(O) and S(O)$_2$, Y is O, $R_3$, $R_4$, $R_5$, $R_6$, $R_7$, $R_8$ are hydrogen, A is selected from the group consisting of

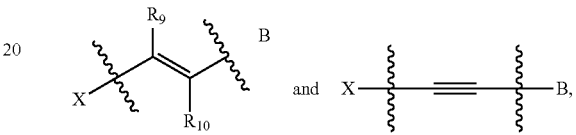

and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: n is as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, X is selected from the group consisting of C(O) and S(O)$_2$, Y is O, $R_3$, $R_4$, $R_5$, $R_6$, $R_7$, $R_8$ are hydrogen, A is selected from the group consisting of

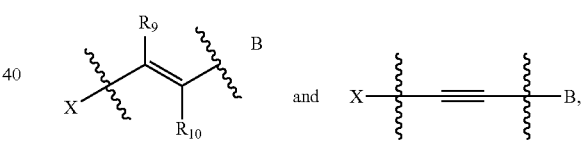

and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: X, Y, $R_1$, and $R_2$ are as described above, n is an integer from 0-2, $R_3$, $R_4$, $R_5$, $R_6$, $R_7$, $R_8$ are hydrogen, A is selected from the group consisting of

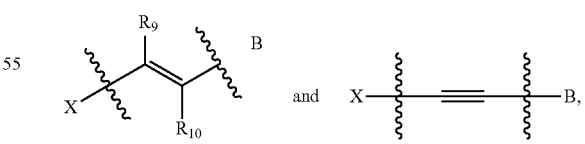

and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: X, Y, and $R_2$ are as described above, $R_1$ is hydrogen, n is an integer from 0-2, $R_3$, $R_4$, $R_5$, $R_6$, $R_7$, $R_8$ are hydrogen, A is selected from the group consisting of

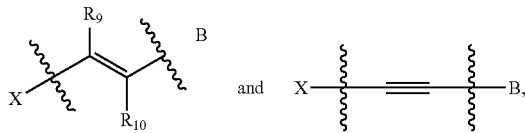

and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: X, and Y are as described above, $R_1$ and $R_2$ are hydrogen, n is an integer from 0-2, $R_3$, $R_4$, $R_5$, $R_6$, $R_7$, $R_8$ are hydrogen, A is selected from the group consisting of

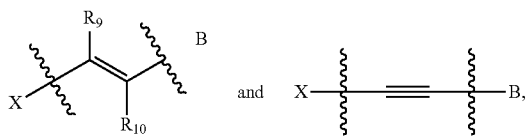

and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: X, and Y are as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, n is an integer from 0-2, $R_3$, $R_4$, $R_5$, $R_6$, $R_7$, $R_8$ are hydrogen, A is selected from the group consisting of

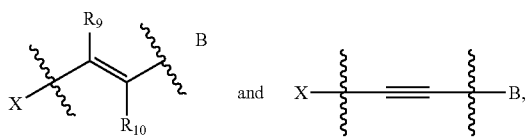

and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: Y, $R_1$, and $R_2$ are as described above, X is selected from the group consisting of C(O) and S(O)$_2$, n is an integer from 0-2, $R_3$, $R_4$, $R_5$, $R_6$, $R_7$, $R_8$ are hydrogen, A is selected from the group consisting of

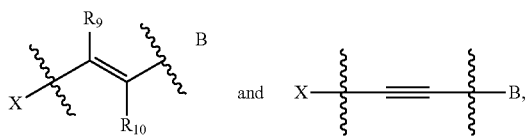

and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: Y, and $R_2$ are as described above, $R_1$ is hydrogen, X is selected from the group consisting of C(O) and S(O)$_2$, n is an integer from 0-2, $R_3$, $R_4$, $R_5$, $R_6$, $R_7$, $R_8$ are hydrogen, A is selected from the group consisting of

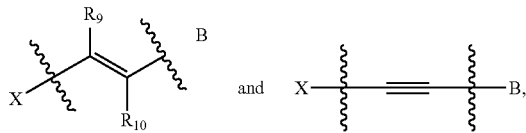

and B is as described above wherein: $R_{11}$ and $R_{16}$ are hydrogen; $R_{12}$, $R_{13}$ and $R_{14}$ are OR; and R is as described above.

In another embodiment, a compound of the disclosure comprises Formula (II), wherein: Y is as described above, $R_1$ and $R_2$ are hydrogen, X is selected from the group consisting of C(O) and S(O)$_2$, n is an integer from 0-2, $R_3$, $R_4$, $R_5$, $R_6$, $R_7$, $R_8$ are hydrogen, A is selected from the group consisting of

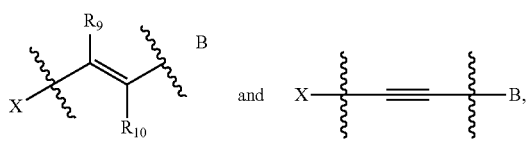

and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: Y is as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, X is selected from the group consisting of C(O) and S(O)$_2$, n is an integer from 0-2, $R_3$, $R_4$, $R_5$, $R_6$, $R_7$, $R_8$ are hydrogen, A is selected from the group consisting of

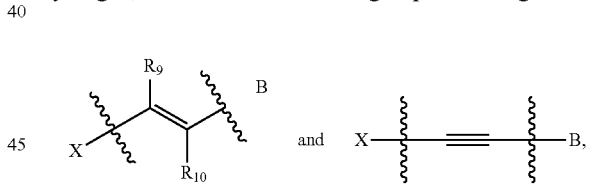

and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: X, $R_1$, and $R_2$ are as described above and Y is O, n is an integer from 0-2, $R_3$, $R_4$, $R_5$, $R_6$, $R_7$, $R_8$ are hydrogen, A is selected from the group consisting of

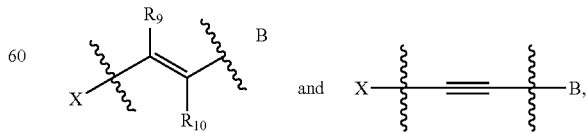

and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: X, and $R_2$ are as described above, $R_1$ is hydrogen, Y is O, n is an integer from 0-2, $R_3$, $R_4$, $R_5$, $R_6$, $R_7$, $R_8$ are hydrogen, A is selected from the group consisting of

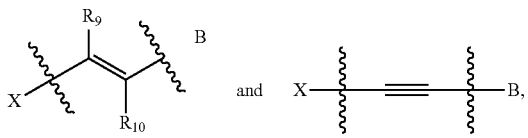

and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: X is as described above, $R_1$ and $R_2$ are hydrogen, Y is O, n is an integer from 0-2, $R_3$, $R_4$, $R_5$, $R_6$, $R_7$, $R_8$ are hydrogen, A is selected from the group consisting of

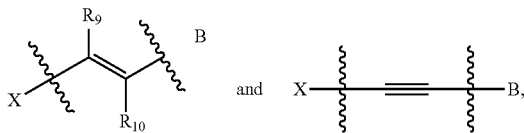

and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: X is as described above, $R_1$ is hydrogen, $R_2$ is selected from the group consisting of a substituted or unsubstituted C1 to C6 alkyl, a substituted or unsubstituted aryl, and a substituted or unsubstituted heteroaryl, Y is O, n is an integer from 0-2, $R_3$, $R_4$, $R_5$, $R_6$, $R_7$, $R_8$ are hydrogen, A is selected from the group consisting of

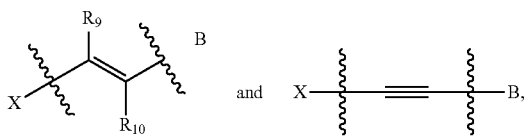

and B is as described above wherein: $R_{11}$ and $R_{15}$ are hydrogen; $R_{12}$, $R_{13}$ and $R_{14}$ are OR; and R is as described above.

In one embodiment, a compound of the disclosure comprises Formula (II), wherein: $R_1$, and $R_2$ are as described above, X is selected from the group consisting of C(O) and $S(O)_2$, Y is O, n is an integer from 0-2, $R_3$, $R_4$, $R_5$, $R_6$, $R_7$, $R_8$ are hydrogen, A is selected from the group consisting of

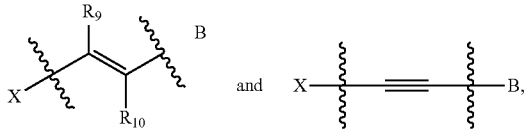

and B is as described above wherein: $R_{11}$ and $R_{15}$ are hydrogen; $R_{12}$, $R_{13}$ and $R_{14}$ are OR; and R is as described above.

In a different embodiment, a compound of the disclosure comprises Formula (II), wherein: $R_2$ is as described above, $R_1$ is hydrogen, X is selected from the group consisting of C(O) and $S(O)_2$, Y is O, n is an integer from 0-2, $R_3$, $R_4$, $R_5$, $R_6$, $R_7$, $R_8$ are hydrogen, A is selected from the group consisting of

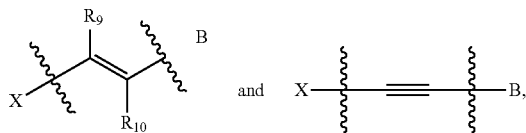

and B is as described above wherein: $R_{11}$ and $R_{15}$ are hydrogen; $R_{12}$, $R_{13}$ and $R_{14}$ are OR; and R is as described above.

In another embodiment, a compound of the disclosure comprises Formula (II), wherein: $R_1$ and $R_2$ are hydrogen, X is selected from the group consisting of C(O) and $S(O)_2$, Y is O, n is an integer from 0-2, $R_3$, $R_4$, $R_5$, $R_6$, $R_7$, $R_8$ are hydrogen, A is selected from the group consisting of

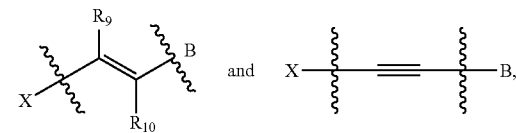

and B is as described above wherein: $R_{11}$ and $R_{15}$ are hydrogen; $R_{12}$, $R_{13}$ and $R_{14}$ are OR; and R is as described above.

In still another embodiment, a compound of the disclosure comprises Formula (II), wherein: $R_1$ is hydrogen, $R_2$ is selected from the group consisting of a substituted or unsubstituted C1 to C6 alkyl, a substituted or unsubstituted aryl, and a substituted or unsubstituted heteroaryl, X is selected from the group consisting of C(O) and $S(O)_2$, Y is O, n is an integer from 0-2, $R_3$, $R_4$, $R_5$, $R_6$, $R_7$, $R_8$ are hydrogen, A is selected from the group consisting of

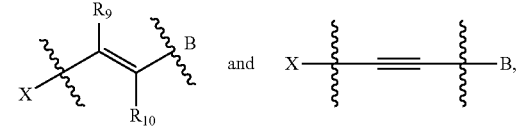

and B is as described above wherein: $R_{11}$ and $R_{15}$ are hydrogen; $R_{12}$, $R_{13}$ and $R_{14}$ are OR; and R is as described above.

Any of the preceding compounds wherein $R_9$ and $R_{10}$ are hydrogen.

Any of the preceding compounds wherein $R_{12}$, $R_{13}$ and $R_{14}$ are $OCH_3$.

In exemplary embodiments, a compound of the disclosure comprises Formula (II) as shown in Table 2.

Dosages of a PL, a PL derivative, a compound of Formula (I) or a compound of Formula (II) can vary between wide limits, depending upon the disease or disorder to be treated, the age and condition of the subject to be treated. In an embodiment where a composition comprising a PL, a PL derivative, a compound of Formula (I) or a compound of Formula (II) is contacted with a sample, the concentration of the PL, a PL derivative, a compound of Formula (I) or a compound of Formula (II) may be from about 1 µM to about 40 µM. Alternatively, the concentration of the PL, a PL derivative, a compound of Formula (I) or a compound of Formula (II) may be from about 5 µM to about 25 µM. For example, the concentration of the PL, a PL derivative, a compound of Formula (I) or a compound of Formula (II) may be about 1, about 2.5 about 5, about 6, about 7, about 8, about 9, about 10, about 11, about 12, about 12, about 14, about 15, about 16, about 17, about 18, about 19, about 20, about 21, about 22, about 23, about 24, about 25, about 30, about 35, or about 40 µM. Additionally, the concentration of the PL, a PL derivative, a compound of Formula (I) or a compound of Formula (II) may be greater than 40 µM. For example, the concentration of the PL, a PL derivative, a compound of Formula (I) or a compound of Formula (II) may be about 40, about 45, about 50, about 55, about 60, about 65, about 70, about 75, about 80, about 85, about 90, about 95 or about 100 µM.

In an embodiment where the composition comprising a PL, a PL derivative, a compound of Formula (I) or a compound of Formula (II) is administered to a subject, the dose of the PL, a PL derivative, a compound of Formula (I) or a compound of Formula (II) may be from about 0.1 mg/kg to about 500 mg/kg. For example, the dose of a PL, a PL derivative, a compound of Formula (I) or a compound of Formula (II) may be about 0.1 mg/kg, about 0.5 mg/kg, about 1 mg/kg, about 5 mg/kg, about 10 mg/kg, about 15 mg/kg, about 20 mg/kg, or about 25 mg/kg. Alternatively, the dose of the PL, a PL derivative, a compound of Formula (I) or a compound of Formula (II) may be about 25 mg/kg, about 50 mg/kg, about 75 mg/kg, about 100 mg/kg, about 125 mg/kg, about 150 mg/kg, about 175 mg/kg, about 200 mg/kg, about 225 mg/kg, or about 250 mg/kg. Additionally, the dose of the PL, a PL derivative, a compound of Formula (I) or a compound of Formula (II) may be about 300 mg/kg, about 325 mg/kg, about 350 mg/kg, about 375 mg/kg, about 400 mg/kg, about 425 mg/kg, about 450 mg/kg, about 475 mg/kg or about 500 mg/kg.

(b) Components of the Composition

The present disclosure also provides pharmaceutical compositions. The pharmaceutical composition comprises PL, a PL derivative, a compound of Formula (I) or a compound of Formula (II), as an active ingredient, and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

In a further embodiment, the excipient may be a lubricant. Non-limiting examples of suitable lubricants include minerals such as talc or silica; and fats such as vegetable stearin, magnesium stearate or stearic acid.

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The composition can be formulated into various dosage forms and administered by a number of different means that will deliver a therapeutically effective amount of the active ingredient. Such compositions can be administered orally, parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Gennaro, A. R., Remington's Pharmaceutical Sciences, Mack Publishing Co., Easton, Pa. (18$^{th}$ ed, 1995), and Liberman, H. A. and Lachman, L., Eds., Pharmaceutical Dosage Forms, Marcel Dekker Inc., New York, N.Y. (1980). In a specific embodiment, a composition may be a food supplement or a composition may be a cosmetic.

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising PL, a PL derivative, a compound of Formula (I) or a compound of Formula (II) is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of the PL, a PL derivative, a compound of Formula (I) or a compound of Formula (II) in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the PL or compound comprising Formula (I) may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9,12,15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying the PL, PL derivative, compound of Formula (I) or compound of Formula (II) (i.e., having at least one methionine compound) may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospolipids detailed above for liposomes are suitable for embodiments directed to microemulsions. The PL or compound comprising Formula (I) may be encapsulated in a microemulsion by any method generally known in the art.

In yet another embodiment, a PL, a PL derivative, a compound of Formula (I) or a compound of Formula (II) may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

(c) Bcl-2 Family Inhibitor

In an aspect, the composition further comprises at least one inhibitor of one or more anti-apoptotic proteins in the Bcl-2 family. As used herein, a "Bcl-2 inhibitor" includes at least one inhibitor of one or more anti-apoptotic proteins in the Bcl-2 family. Specifically, a Bcl-2 inhibitor of the invention selectively kills senescent cells. Methods to determine if a compound inhibits one or more anti-apoptotic proteins in the Bcl-2 family are known in the art. For example, nucleic acid expression, protein expression, or activity of Bcl-2 family proteins may be measured as described in detail below. Methods to determine if a compound selectively kills senescent cells are known in the art. For example, see Section III(b) and Section III(c).

Members of the B-cell lymphoma 2 (Bcl-2) family control the integrity of the outer mitochondrial membrane (OMM) and thus are critical in determining the susceptibility of cells to apoptosis induced by the intrinsic pathway. Bcl-2 family members can be divided into three subfamilies based on structural and functional features: an anti-apoptotic family, a multidomain pro-apoptotic family, and a BH3-only pro-apoptotic family. The anti-apoptotic subfamily suppresses apoptosis and promotes cell survival but not cell proliferation. As such, the anti-apoptotic proteins in the Bcl-2 family may also be referred to as pro-survival proteins. Non-limiting examples of anti-apoptotic Bcl-2 family proteins may include Bcl-2, Bcl-xl, Bcl-w, Mcl-1, Bfl1/A-1, and Bcl-B. The anti-apoptotic Bcl-2 family proteins are characterized by the presence of up to four relatively short sequence motifs, which are less than 20 amino acids in length, known as Bcl-2 homology 1 (BH1), BH2, BH3 and BH4 domains. They also have a C-terminal membrane-anchoring sequence and a similar three-dimensional structure. Inhibitors of one or more anti-apoptotic proteins in the Bcl-2 family may promote cell death by antagonizing the pro-survival function of the Bcl-2 protein family thereby inducing apoptosis. An inhibitor of the invention may inhibit one or more anti-apoptotic proteins in the Bcl-2 family. Accordingly, an inhibitor of the invention may inhibit one or more anti-apoptotic proteins selected from the group consisting of Bcl-2, Bcl-xl, Bcl-w, Mcl-1, Bfl1/A-1, and Bcl-B. In certain embodiments, an inhibitor of the invention is a Bcl-2, Bcl-xl and Bcl-w inhibitor. In a specific embodiment, an inhibitor of the invention is a Bcl-2 and Bcl-xl inhibitor. It is understood that an inhibitor of the invention may primarily inhibit Bcl-2 and/or Bcl-xl, but also have inhibitory effects on other members of the anti-apoptotic proteins in the Bcl-2 family.

An inhibitor of one or more anti-apoptotic proteins in the Bcl-2 family may be an inhibitor that inhibits nucleic acid expression, protein expression, or protein function of a Bcl-2 family protein. An inhibitor may selectively inhibit one, two, three, four, five, six or more members of the Bcl-2 family proteins. In an embodiment, an inhibitor may affect nucleic acid or protein expression of a Bcl-2 family protein. Non-limiting examples of inhibitors that decrease nucleic acid and protein expression may include histone deacetylase inhibitors such as sodium butyrate and depsipeptide, synthetic cytotoxic retinoid such as fenretinide, and cyclin-dependent kinase inhibitors such as flavopiridol. Alternatively, an inhibitor may be an antisense molecule. For example, oblimersen sodium (G3139) is a Bcl-2 antisense that targets BCL-2 mRNA. In another embodiment, an inhibitor may be a natural inhibitor of Bcl-2 family interactions. For example, progidiosin molecules (bypyrrole-containing natural products), such as GX15-070 (obatoclax) may inhibit Bcl-2 family proteins such as Bcl-2, Bcl-xl, Bcl-w and Mcl-1. Additionally, the natural inhibitor gossypol (AT-101) and its derivatives, apogossypolone, TW37 and TM-1206, may inhibit Bcl-2 family proteins such as Bcl-2, Bcl-xl, and Mcl-1. In still another embodiment, an inhibitor may be designed to bind the hydrophobic grove of anti-apoptotic Bcl-2 family proteins in place of BH3-only proteins (i.e., BH3-mimetics). As such, an inhibitor may be a small molecule inhibitor of one or more anti-apoptotic proteins in the Bcl-2 family. For example, isoxazolidine-based small molecules that interact with Bcl-2 and Bcl-xl, ABT-737 and ABT-263 (navitoclax) that bind Bcl-2, Bcl-xl, and Bcl-w. Non-limiting examples of other Bcl-2 family inhibitors may include SAHB$_A$, terphenyl, benzoylureas, A-385358, A-874009, A-1155463, A-1331852, apogossypolone, BM-1074, BM-1197, BXI-72, HA-14, antimycin A, ABT199, WEHI539, MIM-1, and BH$_3$Is. In a specific embodiment, an inhibitor is a molecule similar to ABT-263. In an exemplary embodiment, an inhibitor of one or more anti-apoptotic proteins in the Bcl-2 family is ABT-263 (navitoclax).

In an aspect, a composition of the invention further comprises ABT-263 or an ABT-263 derivative. ABT-263 or ABT-263 derivatives may be modified to improve bioavailability, solubility, stability, handling properties, or a combination thereof, as compared to an unmodified version. Thus, in another aspect, a composition of the invention may further comprise modified ABT-263 or ABT-263 derivative. In still another aspect, a composition of the invention further comprises a prodrug of ABT-263 or an ABT-263 derivative.

In an embodiment, the composition further comprises at least one inhibitor of one or more anti-apoptotic proteins in the Bcl-2 family. For example, the composition may further comprise 1, 2, 3, 4 or 5 or more inhibitors of one or more anti-apoptotic proteins in the Bcl-2 family. Each Bcl-2 inhibitor of the composition may target the same or different anti-apoptotic protein in the Bcl-2 family. In an embodiment, the composition may further comprise two inhibitors of one or more anti-apoptotic proteins in the Bcl-2 family. In another embodiment, the composition may further comprise one inhibitor of one or more anti-apoptotic proteins in the Bcl-2 family.

Dosages of the Bcl-2 family inhibitor can vary between wide limits, depending upon the disease or disorder to be treated, the age and condition of the subject to be treated. In an embodiment where the composition further comprising at least one inhibitor of one or more anti-apoptotic proteins in the Bcl-2 family is contacted with a sample, the concentration of the at least one inhibitor of one or more anti-apoptotic proteins in the Bcl-2 family may be from about 0.01 µM to about 10 µM. Alternatively, the concentration of the at least one inhibitor of one or more anti-apoptotic proteins in the Bcl-2 family may be from about 0.01 µM to about 5 µM. For example, the concentration of the at least one inhibitor of one or more anti-apoptotic proteins in the Bcl-2 family may be about 0.01, about 0.05, about 0.1, about 0.2, about 0.3, about 0.4, about 0.5, about 0.6, about 0.7, about 0.8, about 0.9, about 1, about 2, about 3, about 4, about 5, about 6, about 7, about 8, about 9 or about 10 µM. Additionally, the concentration of the at least one inhibitor of one or more anti-apoptotic proteins in the Bcl-2 family may be greater than 10 µM. For example, the concentration of the at least one inhibitor of one or more anti-apoptotic proteins in the Bcl-2 family may be about 10, about 15, about 20, about 25, about 30, about 35, about 40, about 45, about 50, about 55, about 60, about 65, about 70, about 75, about 80, about 85, about 90, about 95 or about 100 µM.

In an embodiment where the composition further comprising at least one inhibitor of one or more anti-apoptotic proteins in the Bcl-2 family is administered to a subject, the dose of inhibitor may be from about 0.1 mg/kg to about 500 mg/kg. For example, the dose of the least one inhibitor of one or more anti-apoptotic proteins in the Bcl-2 family may be about 0.1 mg/kg, about 0.5 mg/kg, about 1 mg/kg, about 5 mg/kg, about 10 mg/kg, about 15 mg/kg, about 20 mg/kg, or about 25 mg/kg. Alternatively, the dose of the least one inhibitor of one or more anti-apoptotic proteins in the Bcl-2 family may be about 25 mg/kg, about 50 mg/kg, about 75 mg/kg, about 100 mg/kg, about 125 mg/kg, about 150 mg/kg, about 175 mg/kg, about 200 mg/kg, about 225 mg/kg, or about 250 mg/kg. Additionally, the dose of the least one inhibitor of one or more anti-apoptotic proteins in the Bcl-2 family may be about 300 mg/kg, about 325 mg/kg, about 350 mg/kg, about 375 mg/kg, about 400 mg/kg, about 425 mg/kg, about 450 mg/kg, about 475 mg/kg or about 500 mg/kg.

II. Process of Making a Compound Comprising Formula (I) or Formula (II)

In an embodiment, a compound comprising Formula (I) may be synthesized via the reaction scheme depicted in Scheme 1.

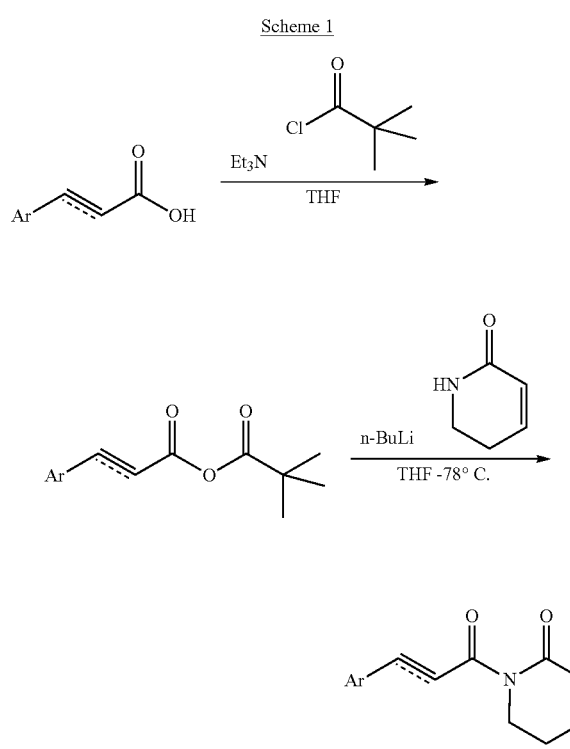

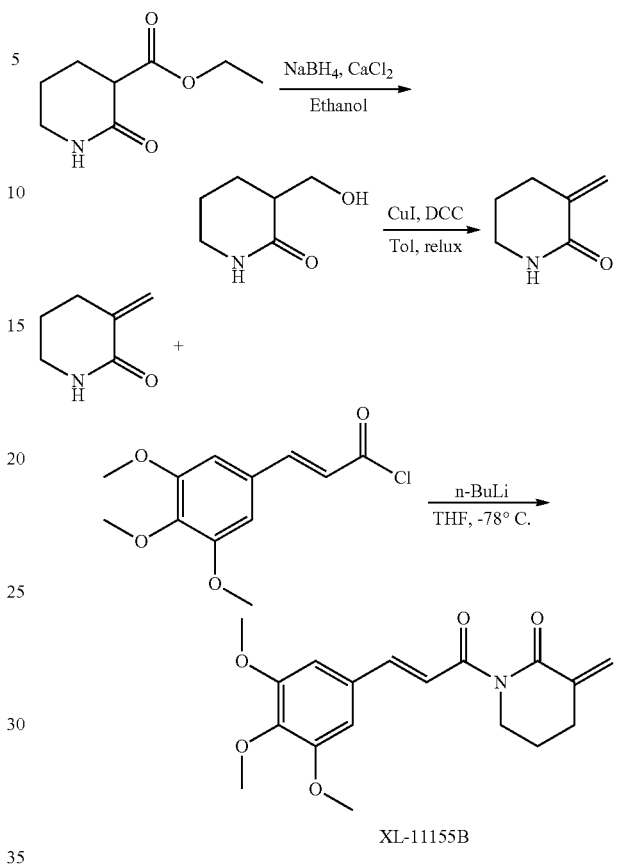

By way of non-limiting example, $Et_3N$ (about 1.15 eq) and pivaloyl chloride (about 1.1 eq) may be added to a solution of acid (about 1 eq) in dry THF. The reaction mixture may be stirred for about 45-60 min for completion (monitored by TLC). The mixture may be filtered and the filtrate may be used directly for the next step. About 0.88 eq of n-BuLi may be added to a stirred solution of 5,6-dihydropyridin-2(1H)-one (0.8 eq) in dry THF under inert atmosphere at about −78° C. After stirring for about 0.5 h, the mixed anhydride solution prepared from above may be added and the resulting reaction mixture may be stirred for about 1 h before quenched with saturated $NH_4Cl$ (about 0.5 mL). The mixture may be extracted with ethylacetate (10 mL×3). The organic phases may be combined, washed with sat. NaCl, dried over anhydrous $Na_2SO_4$, and evaporated to dryness under vacuum. The product may be purified purified by silica gel column chromatography. A skilled artisan would be able to determine various changes to the reactions described above that would result in various compounds comprising Formula (I).

In another embodiment, a compound comprising Formula (II) may be synthesized via the reaction scheme depicted in Scheme 2.

By way of non-limiting example, a mixture of ethyl 2-oxopiperidine-3-carboxylate and calcium chloride in ethanol may be cooled to about 0° C. and treated with sodium borohydride. The resulting mixture may be allowed to warm to about room temperature and stirred for about 6 hrs. The reaction may then quenched with acetone and the pH of the mixture may be adjusted to about pH to 3-4 with about 1.0 M HCl. The resulting mixture may be extracted with methylene chloride, organic phases may be combined, dried over $Na_2SO_4$, filtered, and evaporated to dryness under vacuum. The product may be purified by silica gel column chromatography. Then, cuprous iodine may be added to a stirred solution of 3-(Hydroxymethyl)piperidin-2-one and dicyclohexylcarbodiimide (DCC) in toluene. The resulting mixture may be stirred under reflux for about 1.5 hrs and cooled to room temperature. Water may be added and the mixture stirred overnight. Ethylacetate may be added and the mixture may be filtered. The aqueous phase may be extracted with ethyl acetate and the combined organic phases may be washed with brine, dried over $Na_2SO_4$, filtered, and evaporated to dryness under vacuum. The product may be purified by silica gel column chromatography. Next, a solution of 3-Methylene-2-piperidinone in THF may be cooled to about −78° C., n-BuLi may be added slowly. The resulting mixture may be allowed to stir at about −78° C. for about 1 hr. A solution of (E)-3-(3,4,5-trimethoxyphenyl)acryloyl chloride in THF may then be added dropwise. After addition, the mixture may be stirred under about −78° C. for about 1 hr. The reaction may then quenched with aqueous ammonium chloride solution and may be extracted with ethylacetate. The combined organic phases may be washed with brine, dried over Na$_2$SO$_4$, filtered, and evaporated to dryness under vacuum. The product may be purified by silica gel column chromatography. A skilled artisan would be able to determine various changes to the reactions described above that would result in various compounds comprising Formula (II).

In still another embodiment, a compound comprising Formula (II) may be synthesized via the reaction scheme depicted in Scheme 3.

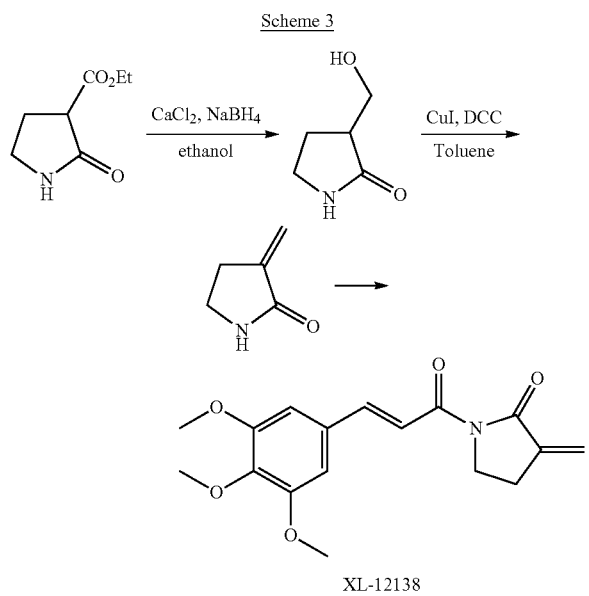

By way of non-limiting example, ethyl 2-oxopyrrolidine-3-carboxylate may be added to a suspension of NaBH$_4$ and CaCl$_2$ in ethanol under about 0° C. and the resulting mixture may stirred overnight at about room temperature. The reaction may be quenched with about 1M HCl solution, then extracted with CH$_2$Cl$_2$/MeOH(10/1) about 10 to 20 times, the combined organic phases may be dried over Na$_2$SO$_4$, filtered, and evaporated to dryness under vacuum. The product may be purified by silica gel column chromatography. Next, 3-(Hydroxymethyl)pyrrolidin-2-one may be treated with CuI and DCC in toluene under reflux for about 3 h. The reaction mixture may be cooled to about room temperature and quenched with several drops of water, followed by filtration, the filtrate may be concentrated and purified through column. Then, 3-Methylenepyrrolidin-2-one may be dissolved in THF and cooled to about −78° C., and n-BuLi may be added dropwise under N$_2$ protection, the resulting mixture may be stirred under about −78° C. for about 1 h. (E)-t-butyl 3-(3,4,5-trimethoxyphenyl)acrylate (about 1.5 eq) may be added. After stirring at about −78° C. for about 1 h, the reaction may be quenched with NH$_4$Cl solution, extracted with EtOAc about 3 times, the combined organic phases may be washed with brine and dried over Na$_2$SO$_4$, filtered, and evaporated to dryness under vacuum. The residue may be purified by flash column chromatography. A skilled artisan would be able to determine various changes to the reactions described above that would result in various compounds comprising Formula (II).

In still yet another embodiment, a compound comprising Formula (II) may be synthesized via the reaction scheme depicted in Scheme 4.

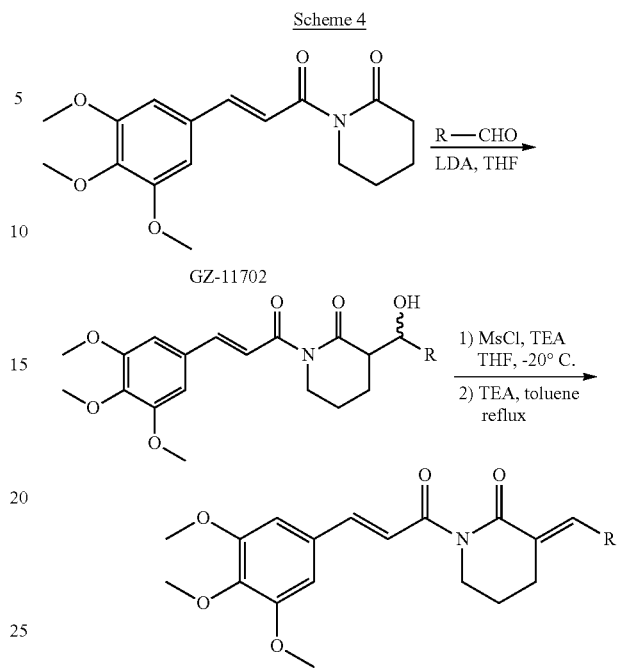

By way of non-limiting example, LHMDS may be added to a solution of (E)-1-(3-(3,4,5-trimethoxyphenyl)acryloyl)piperidin-2-one in THF at about −78° C. The resulting solution may be stirred at this temperature for about 1 h. Aromatic aldehyde (about 1 eq; dissolved in small amount of THF) may be added dropwise. After stirring at about −78° C. for about an additional hour, ammonium chloride solution may be added to quench the reaction, the mixture may be extracted with EtOAc about 3 times. The combined organic phases may be washed with water and brine, dried over Na$_2$SO$_4$, filtered, and evaporated to dryness under vacuum. The residue may be purified by flash column chromatography to afford the corresponding hydroxyl intermediate. Next, methanesulfonyl chloride (about 1.2 eq) may be added to a solution of the above intermediate and TEA (about 1.5 eq) in toluene under ice bath. After stirring at about room temperature for about 1 h, additional about 2.5 eq TEA may be added. The resulting mixture may be heated to reflux for about 5.5 h. Upon cooled to about room temperature, the reaction may be quenched with water and extracted with ethylacetate. The combined organic fractions may be washed with brine, dried over Na$_2$SO$_4$, filtered, and evaporated to dryness under vacuum. The residue may be purified by flash column chromatography to afford the desired product. A skilled artisan would be able to determine various changes to the reactions described above that would result in various compounds comprising Formula (II).

In a different embodiment, a compound comprising Formula (II) may be synthesized via the reaction scheme depicted in Scheme 5.

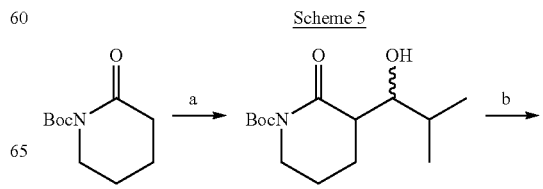

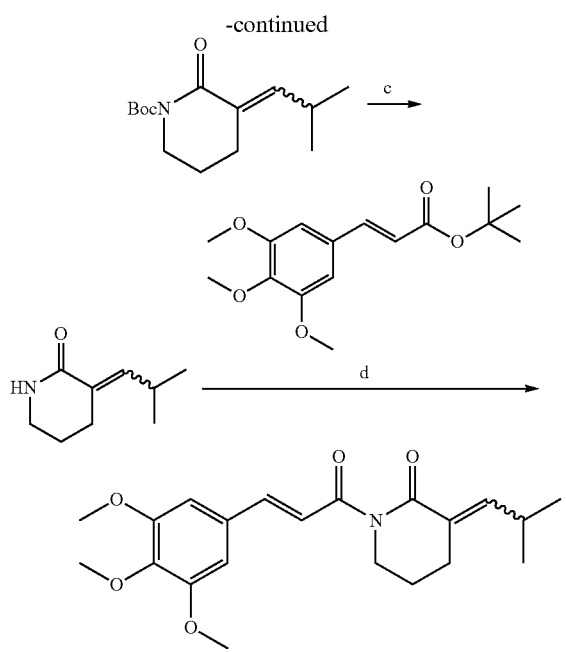

Reagents and conditions: a. LHDMS, isobutyraldehyde, THF,-78°C.; b. 1). MsCl, TEA, THF, -20° C.; 2). TEA, Tol., reflux. c. TFA, CH$_2$Cl$_2$, 0° C.; d. n-BuLi, THF, -78° C.

By way of non-limiting example, LHDMS may be added to a solution of tert-butyl 2-oxopiperidine-1-carboxylate in THF at about −78° C. under N$_2$ protection. After stirring at this temperature for about 1 h, isobutyraldehyde may be added dropwise. The resulting mixture may be allowed to stir for about an additional hour before quenched by slowly adding saturated NH$_4$Cl solution, then diluted with EtOAc and the organic fraction may be washed with brine, dried over Na$_2$SO$_4$, filtered, and evaporated to dryness under vacuum. The residue may be purified by flash column chromatography to afford the desired product. Next, methanesulfonyl chloride may be added to a solution of t-butyl 3-(1-hydroxy-2-methylpropyl)-2-oxopiperidine-1-carboxylate and TEA in toluene at about 0° C. After stirring at about room temperature for about 1 h, additional TEA may then be added, the resulting mixture may be heated to reflux and stirred under reflux for about 6 h. After cooling down to about room temperature, the reaction may be quenched with water and extracted with EtOAc. The combined organic fractions may be washed with brine, dried over Na$_2$SO$_4$, filtered, and evaporated to dryness under vacuum. The residue may be purified by flash column chromatography to afford both a E isomer and Z isomer product. Next, TFA may be added to a solution of t-butyl 3-(2-methylpropylidene)-2-oxopiperidine-1-carboxylate (Z or E isomer) in CH$_2$Cl$_2$ at about 0° C. The resulting mixture may be allowed to stir at about 0° C. for about 2 h. The reaction may then be quenched with saturated sodium bicarbonate under ice bath and extracted with CH$_2$Cl$_2$. The combined organic fractions may be washed with brine, dried over Na$_2$SO$_4$, filtered, and evaporated to dryness under vacuum. The residue may be purified by flash column chromatography to afford the corresponding Z or E isomer. Next, n-BuLi may be added to a solution of 3-(2-methylpropylidene) piperidin-2-one (Z or E isomer) in THF at about −78° C. under N$_2$ protection. After stirring at about −78° C. for about 1 h, (E)-tert-butyl 3-(3,4,5-trimethoxyphenyl)acrylate may be added. The resulting mixture may be stirred at about −78° C. for about 45 min and then quenched with saturated NH$_4$Cl water solution. The whole mixture may be extracted with EA several times. The combined organic phase may be washed with brine, dried over Na$_2$SO$_4$, filtered, and evaporated to dryness under vacuum. The residue may be purified by flash column chromatography to afford the corresponding Z or E isomer. A skilled artisan would be able to determine various changes to the reactions described above that would result in various compounds comprising Formula (II).

In another embodiment, a compound comprising Formula (II) may be synthesized via the reaction scheme depicted in Scheme 6.

Scheme 6

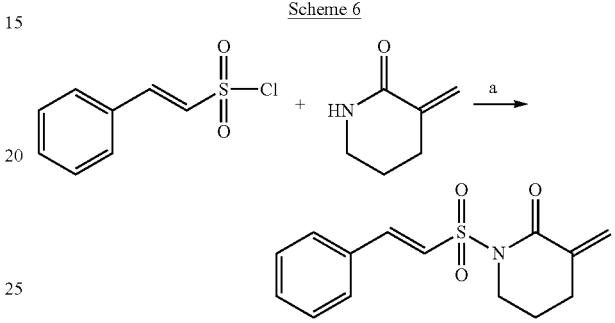

By way of non-limiting example, n-BuLi may be added to a solution of 3-methylenepiperidin-2-one in THF at about −78° C. After stirring at this temperature for about 1 h, (E)-2-phenylethenesulfonyl chloride (dissolved in small amount of THF) may be added. The resulting mixture may be stirred for about another 1 h and then quenched with saturated NH$_4$Cl water solution. The whole mixture may be extracted with EA several times. The combined organic phase may be washed with brine, dried over Na$_2$SO$_4$, filtered, and evaporated to dryness under vacuum. The residue may purified by flash column chromatography to afford the desired product. A skilled artisan would be able to determine various changes to the reactions described above that would result in various compounds comprising Formula (II).

In another embodiment, a compound comprising Formula (II) may be synthesized via the reaction scheme depicted in Scheme 7.

Scheme 7

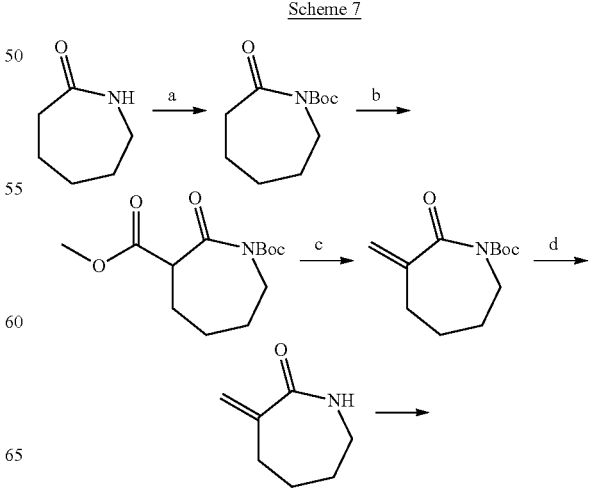

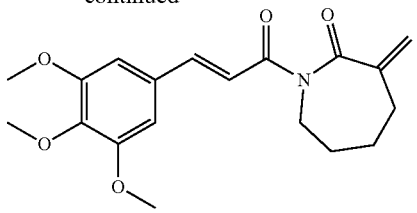

Conditions: a. DMAP, Et₃N, Boc₂O, CH₂Cl₂, r.t.; b. LHMDS, THF, -78° C.;
c. (HCHO)n, 18-crown-6, K₂CO₃, Tol, reflux; d. TFA, CH₂Cl₂, 0° C.

By way of non-limiting example, Boc₂O may be added to a solution of ε-Caprolactam, DMAP and Et₃N in CH₂Cl₂ at about 0° C. The resulting mixture may be stirred at about room temperature overnight. Solvent may be evaporated giving a residue which may be purified. Next, LHMDS may be added to a solution of tert-butyl 2-oxoazepane-1-carboxylate in THF at about −78° C. The resulting mixture may be stirred at this temperature for about 45 min and methyl carbonochloridate may then be added. The whole mixture may be stirred for about an additional 1 h and quenched with saturated NH₄Cl water solution, followed by extraction with EA several times. The combined organic phase may be washed with brine and dried over anhydrous sodium sulfate. Solvent may be evaporated giving a residue which may be purified. Next, paraformaldehyde may be added to a suspension of 1-tert-butyl 3-methyl 2-oxoazepane-1,3-dicarboxylate, 18-crown-6, K₂CO₃ in toluene. The resulting mixture may be stirred under reflux for about 4-5 hours and then cooled to about room temperature and water may be added. The whole mixture may be extracted with EA about 3 times. The combined organic phase may be washed with brine and dried over anhydrous sodium sulfate. Solvent may be evaporated giving a residue which may be purified. Next, TFA may be added to a solution of tert-butyl 3-methylene-2-oxoazepane-1-carboxylate in CH₂Cl₂ at 0° C. The resulting solution may be stirred at this temperature for about 2 h. Saturated sodium bicarbonate solution may be added until pH larger than about 7. The mixture may then be extracted with CH₂Cl₂ about 5-10 times and the combined organic phase may be washed with brine and dried over anhydrous sodium sulfate. Solvent may be evaporated giving a residue which may be purified. Next, n-BuLi may be added to a solution of 3-methyleneazepan-2-one in THF at about −78° C. After stirring at this temperature for about 1 h, (E)-tert-butyl 3-(3,4,5-trimethoxyphenyl)acrylate may then be added. The resulting mixture may be stirred at about −78° C. for about an additional 1 h and then quenched with saturated NH₄Cl solution. The whole mixture may then be extracted with EA several times and the combined organic phase may be washed with brine and dried over anhydrous sodium sulfate. Solvent may be evaporated giving a residue which may be purified chromatographically to get pure product. A skilled artisan would be able to determine various changes to the reactions described above that would result in various compounds comprising Formula (II).

In still another embodiment, a compound comprising Formula (II) may be synthesized via the reaction scheme depicted in Scheme 8.

Scheme 8

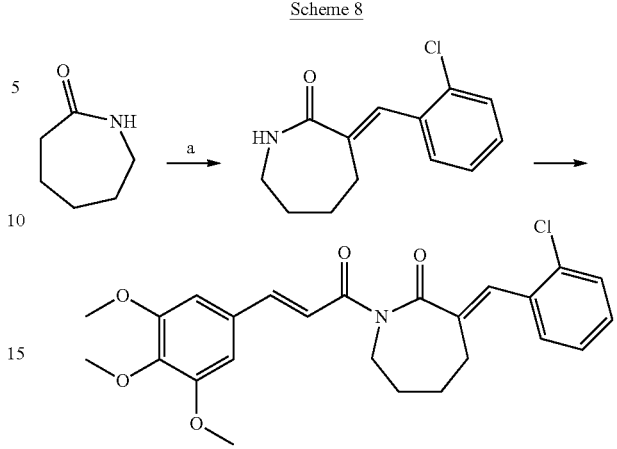

Conditions and reagents: a. (1) TFAA, Tol; (2) 2-chlorobenzaldehyde, t-BuOK, THF.

By way of non-limiting example, TFAA may be added to a solution of azepan-2-onein toluene at about 0° C. After stirring under ice bath for about 1 h, the solvent may be removed to give a residue. The residue may be mixed with 2-chlorobenzaldehyde and charged to a suspension of t-BuOK in THF at about 0° C. The resulting mixture may then be heated to about 50-60° C. and stirred at this temperature for about 1.5 h. The reaction mixture may be concentrated under vacuum and water may then be added. The resulting mixture may be extracted with EA about 3 times. The combined organic phase may be washed with brine and dried over anhydrous sodium sulfate. Solvent may be evaporated giving a residue which may be purified. Next, n-BuLi may be added to a solution of (E)-3-(2-chlorobenzylidene)azepan-2-one in THF at about −78° C. After stirring at about −78° C. for about 1 h, (E)-tert-butyl 3-(3,4,5-trimethoxyphenyl)acrylate may be added and the resulting mixture may be stirred at about −78° C. for about an additional 1 h. The reaction may be quenched with saturated NH₄Cl solution and then extracted with EA about 3 times. The combined organic phase may be washed with brine and dried over anhydrous sodium sulfate. Solvent may be evaporated giving a residue which may be purified to get pure product. A skilled artisan would be able to determine various changes to the reactions described above that would result in various compounds comprising Formula (II).

III. Methods

The present disclosure encompasses a method of selectively killing one or more senescent cells in a sample, the method comprising contacting a composition comprising an effective amount of PL, a PL derivative, a compound of Formula (I) or a compound of Formula (II) with the sample. In another aspect, the present disclosure encompasses a method of selectively killing one or more senescent cells in a subject in need thereof, the method comprising administering to the subject a composition comprising a therapeutically effective amount PL, a PL derivative, a compound of Formula (I) or a compound of Formula (II).

By selectively killing one or more senescent cells is meant a composition of the invention does not appreciably kill non-senescent cells at the same concentration. Accordingly, the median lethal dose or LD50 of the inhibitor in non-senescent cells may be about 5 to about 50 times higher than the LD50 of the inhibitor in senescent cells. As used herein, the LD50 is the concentration of inhibitor required to kill half the cells in the cell sample. For example, the LD50 of the inhibitor in non-senescent cells may be greater than about 5, about 6, about 7, about 8, about 9 or about 10 times higher than the LD50 of the inhibitor in senescent cells. Alternatively, the LD50 of the inhibitor in non-senescent cells may be greater than about 10, about 15, about 20, about 25, about 30, about 35, about 40, about 45, or about 50 times higher than the LD50 of the inhibitor in senescent cells. Additionally, the LD50 of the inhibitor in non-senescent cells may be greater than 50 times higher than the LD50 of the inhibitor in senescent cells. In a specific embodiment, the LD50 of the inhibitor in non-senescent cells is greater than 10 times higher than the LD50 of the inhibitor in senescent cells. In another specific embodiment, the LD50 of the inhibitor in non-senescent cells is greater than 20 times higher than the LD50 of the inhibitor in senescent cells.

The progression from an actively dividing cell to a metabolically active, non-dividing cell is termed "senescence" or "cellular senescence." As used herein, the terms "senescence" and "cellular senescence" may be used interchangeably. The term "senescence" also refers to the state into which cells enter after multiple rounds of division and, as a result of cellular pathways, future cell division is prevented from occurring even though the cell remains metabolically active. Senescent cells may differ from their pre-senescent counterparts in one or more of the following ways: 1) they arrest growth and cannot be stimulated to reenter the cell cycle by physiological mitogens; 2) they become resistant to apoptotic cell death; and/or 3) they acquire altered differentiated functions.

In contrast to cancer cells which grow and divide uncontrollably, the ability of most differentiated eukaryotic cells to proliferate is finite. Stated another way, normal cells have an intrinsically determined limit to the number of cell divisions through which they can proceed. This phenomenon has been termed "replicative cellular senescence" and is an intrinsic anticancer mechanism that limits a cell's proliferative ability, thereby preventing neoplastic transformation. Another form of senescence is "premature cellular senescence." Premature cellular senescence, like replicative cellular senescence, is a terminal fate of mitotic cells, characterized by permanent cell cycle arrest. Unlike replicative cellular senescence, however, premature cellular senescence does not require telomere deterioration and can be induced by a variety of stressors including, but not limited to, ultraviolet light, reactive oxygen species, chemotherapeutics, environmental toxin, cigarette smoking, ionizing radiation, distortion of chromatin structure, excessive mitogenic signaling, and oncogenic mutations. Still another form of senescence is therapy-induced senescence (TIS) which refers to the phenomenon of a subset of tumor cells being forced into a senescent state by therapeutic agents. TIS is known to develop because of certain treatments, including radiotherapy and chemotherapy.

The number of senescent cells in various organs and tissues of a subject increases with age. The accumulation of senescent cells may drive the deterioration that underlies aging and age-related diseases. For example, the accumulation of senescent cells in aged tissue may contribute to age-associated tissue dysfunction, reduced regenerative capacity, and disease. In this context, senescence is considered deleterious because it contributes to decrements in tissue renewal and function. As a non-limiting example, an aged tissue may lack the ability to respond to stress when proliferation is required thereby resulting in the reduced fitness seen with aging. A key component of this model is that substantial numbers of senescent cells should be present in tissues with aging, without, or prior to, pathology.

(a) Senescent Cells

A senescent cell may be a cell that ceases to divide but remains metabolically active. The non-dividing cells may remain viable for many weeks, but fail to grow/replicate DNA despite the presence of ample space, nutrients and growth factors in the medium. Thus, the senescence growth arrest is essentially permanent because senescent cells cannot be stimulated to proliferate by known physiological stimuli. Further, a senescent cell of the invention may be resistant to certain apoptotic signals and may acquire widespread changes in gene expression. The resistance to apoptosis may explain the increase in senescent cells with age. Manipulation of pro- and anti-apoptotic proteins may cause cells that are destined to die by apoptosis to senesce and, conversely, cause cells that are destined to senesce to undergo apoptosis.

A senescent cell of the invention may be senescent due to replicative cellular senescence, premature cellular senescence or therapy-induced senescence. Senescent cells that are senescent due to replication may have undergone greater than 60 population doublings. Alternatively, senescent cells that are senescent due to replication may have undergone greater than 40, greater than 50, greater than 60, greater than 70 or greater than 80 population doublings. A senescent cell that is prematurely cellular senescent may be induced by, but not limited to, ultraviolet light, reactive oxygen species, chemotherapeutics, environmental toxin, cigarette smoking, ionizing radiation, distortion of chromatin structure, excessive mitogenic signaling, and oncogenic mutations. In a specific embodiment, premature cellular senescence may be induced by ionizing radiation (IR). In another specific embodiment, premature cellular senescence may also be induced by ectopic transfection with Ras oncogene. A senescent cell that is therapy-induced senescent may have been exposed to DNA-damaging therapy.

A senescent cell of the invention may generally be a eurkaryotic cell. Non-limiting examples of senescent cells may include, but are not limited to, mammary epithelial cells, keratinocytes, cardiac myocytes, chondrocytes, endothelial cells (large vessels), endothelial cells (microvascular), epithelial cells, fibroblasts, follicle dermal papilla cells, hepatocytes, melanocytes, osteoblasts, preadipocytes, primary cells of the immune system, skeletal muscle cells, smooth muscle cells, adipocytes, neurons, glial cells, contractile cells, exocrine secretory epithelial cells, extracellular matrix cells, hormone secreting cells, keratinizing epithelial cells, islet cells, lens cells, mesenchymal stem cells, pancreatic acinar cells, paneth cells of the small intestine, primary cells of hemopoietic linage, primary cells of the nervous system, sense organ and peripheral neuron supporting cells, wet stratified barrier epithelial cells and stem cells. In a specific embodiment, the stem cells are adult stem cells. Adult stem cells are stem cells which maintain and repair the tissue in which they are found and are generally referred to by their tissue of origin. Non-limiting examples of adult stem cells include muscle stem cells, hematopoietic stem cells, heart stem cells, neural stem cells, mesenchymal stem cells, intestinal stem cells, skin stem cells, adipose-derived stem cells, endothelial stem cells, and dental pulp stem cells. In a specific embodiment, a senescent cell of the invention is a fibroblast. In another specific embodiment, a senescent cell may be a hematopoietic stem cell.

Further, a senescent cell of the invention may be found in renewable tissues, including the vasculature, hematopoietic system, epithelial organs and the stroma. A senescent cell of the invention may also be found at sites of aging or chronic age-related pathology, such as osteoarthritis and atherosclerosis. Further, a senescent cell of the invention may be associated with benign dysplastic or preneoplastic lesions and benign prostatic hyperplasia. In an embodiment, a senescent cell of the invention may be found in normal and tumor tissues following DNA-damaging therapy. In a specific embodiment, a senescent cell may be found at a site of aging or age-related pathology.

An age-related pathology may include any disease or condition which is fully or partially mediated by the induction or maintenance of a non-proliferating or senescent state in a cell or a population of cells in a subject. Non-limiting examples include age-related tissue or organ decline which may lack visible indication of pathology, or overt pathology such as a degenerative disease or a function-decreasing disorder. For example, Alzheimer's disease, Parkinson's disease, cataracts, macular degeneration, glaucoma, atherosclerosis, acute coronary syndrome, myocardial infarction, stroke, hypertension, idiopathic pulmonary fibrosis (IPF), chronic obstructive pulmonary disease (COPD), osteoarthritis, type 2 diabetes, obesity, fat dysfunction, coronary artery disease, cerebrovascular disease, periodontal disease, and cancer treatment-related disability such as atrophy and fibrosis in various tissues, brain and heart injury, and therapy-related myelodysplastic syndromes. Additionally, an age-related pathology may include an accelerated aging disease such as progeroid syndromes (i.e. Hutchinson-Gilford progeria syndrome, Werner syndrome, Bloom syndrome, Rothmund-Thomson Syndrome, Cockayne syndrome, xeroderma pigmentosum, trichothiodystrophy, combined xeroderma pigmentosum-Cockayne syndrome, restrictive dermopathy), ataxia telangiectasia, Fanconi anemia, Friedreich's ataxia, dyskeratosis congenital, aplastic anemia, IPF, and others. A method of identifying an age-related disease or condition as described herein may include detecting the presence of senescent cells.

(b) Detecting Senescent Cells

In an aspect, a method of the invention may comprise detecting senescent cells. Senescent cells may be detected in vivo or in vitro. Suitable markers for detecting senescent cells in vitro and in vivo are known in the art. For example, methods to detect senescent cells may include, but are not limited to, detecting lack of DNA replication by incorporation of a DNA-staining reagent (e.g. 5-bromodeoxyuridine (BrdU), $^3$H-thymidine), immunostaining for proteins such as proliferating cell nuclear antigen (PCNA) and Ki-67, histochemical staining for senescence-associated β-galactosidase (SA-β-gal), detecting expression of p16, p19, Pai1, Igfbp2, IL-6, Mmp13, Nrg1, differentiated embryo-chondrocyte expressed-1 (DEC1), p15 (a CDK1) and decoy death receptor-2 (DCR2), detecting cytological markers such as senescence-associated heterochromatin foci (SAHFs) and senescence-associated DNA-damage foci (SDFs). SAHFs may be detected by the preferential binding of DNA dyes, such as 4',6-diamidino-2-phenylindole (DAPI), and the presence of certain heterochromatin-associated histone modifications (for example, H3 Lys9 methylation) and proteins (for example, heterochromatin protein-1 (HP1)). Additionally, senescent cells may be detected as described in U.S. Pat. No. 5,491,069 and US Patent Application No. 2010/0086941. In certain embodiments, senescent cells are detected by histochemical staining for SA-β-gal.

In certain embodiments, one or more senescent cells are detected in a sample. A sample may be a cell sample, a tissue sample, or a biopsy from a subject. Generally speaking, a sample may be dependent on the age-related pathology. For instance, a sample may be tissue biopsy material. As such, a tissue sample may be from esophagus, stomach, liver, gallbladder, pancreas, adrenal glands, bladder, gallbladder, large intestine, small intestine, kidneys, liver, pancreas, colon, stomach, thymus, spleen, brain, spinal cord, nerves, adipose tissue, heart, lungs, eyes, corneal, skin or islet tissue or organs. In a specific embodiment, a tissue sample may be from lung, skeletal muscle, and brain. In another specific embodiment, a tissue sample may be from liver and heart. Alternatively, a sample may be a cell sample. As such, a cell sample may be oocytes and/or spermatozoa, mesenchymal stem cells, adipocytes, central nervous system neurons and glial cells, contractile cells, exocrine secretory epithelial cells, extracellular matrix cells, hormone secreting cells, keratinizing epithelial cells, islet cells, kidney cells, lens cells, pancreatic acinar cells, paneth cells of small intestine, primary cells of hemopoietic lineage, primary cells of the nervous system, sense organ and peripheral neuron supporting cells or wet stratified barrier epithelial cells. Detection of senescent cells may be used to assess the replicative history of tissues, thereby providing a method for evaluation of the physiological, in contrast to the chronological age of the tissue.

The number of senescent cells may increase with age. The number of senescent cells in a tissue or sample may be from less than 1% to greater than 15%. In an embodiment, the number of senescent cells in a tissue or sample may be less than 1%, less than 2%, less than 3%, less than 4%, or less than 5%. In another embodiment, the number of senescent cells in a tissue or sample may be about 5%, about 6%, about 7%, about 8%, about 9%, or about 10%. In still another embodiment, the number of senescent cells in a tissue or sample may be greater than 10%, greater than 11%, greater than 12%, greater than 13%, greater than 14%, or greater than 15%.

(c) Measuring Cell Death

In an aspect, a method of the invention may comprise measuring cell death of senescent cells. Methods of measuring cell death are known in the art. For example, cell death may be measured by Giemsa staining, trypan blue exclusion, acridine orange/ethidium bromide (AO/EB) double staining for fluorescence microscopy and flow cytometry, propidium iodide (PI) staining, annexin V assay, TUNEL assay, DNA ladder, LDH activity, and MTT assay. In a preferred embodiment, cell death is due to induction of apoptosis. Cell death due to induction of apoptosis may be measured by observation of morphological characteristics including cell shrinkage, cytoplasmic condensation, chromatin segregation and condensation, membrane blebbing, and the formation of membrane-bound apoptotic bodies. Cell death due to induction of apoptosis may be measured by observation of biochemical hallmarks including internucleosomal DNA cleavage into oligonucleosome-length fragments. Traditional cell-based methods of measuring cell death due to induction of apoptosis include light and electron microscopy, vital dyes, and nuclear stains. Biochemical methods include DNA laddering, lactate dehydrogenase enzyme release, and MTT/XTT enzyme activity. Additionally, terminal deoxynucleotidyl transferase-mediated dUTP-biotin nick end labeling of DNA fragments (TUNEL) and in situ end labeling (ISEL) techniques are used, which when used in conjunction with standard flow cytometric staining methods yield informative data relating cell death to various cellular parameters, including cell cycle and cell phenotype. See Loo and Rillema, Methods Cell Biol. 1998; 57:251-64, which is incorporated herein by reference, for a review of these methods. In an exemplary embodiment, cell death due to apoptosis may be measured by the reduction of procaspase-3. Caspase-3 has been implicated as an "effector" caspase associated with the initiation of the "death cascade" and is therefore an important marker of the cell's entry point into the apoptotic signaling pathway. Caspase-3 is activated by the upstream caspase-8 and caspase-9, and since it serves as a convergence point for different signaling pathways, it is well suited as a read-out in an apoptosis assay.

The results of these methods may be used to determine the percentage of viable cells. In a preferred embodiment, cell death may be measured as a reduction in viable cells. Since a composition of the invention selectively kills senescent cells, a reduction in viable cells is indicative of a reduction in senescent cells. As described in Section III(b), the number of senescent cells in a sample may be from less than 1% to greater than 15%. As such, a reduction in viable cells following administration of an inhibitor of the invention may be greater than 15% to less than 1%. For example, the reduction in viable cells may be less than 1%, less than 2%, less than 3%, less than 4%, or less than 5%. Alternatively, the reduction in viable cells may be about 5%, about 6%, about 7%, about 8%, about 9%, or about 10%. Additionally, the reduction in viable cells may be greater than 10%, greater than 11%, greater than 12%, greater than 13%, greater than 14%, or greater than 15%.

(d) Administration

In certain aspects, a therapeutically effective amount of a composition of the invention may be administered to a subject. Administration is performed using standard effective techniques, including peripherally (i.e. not by administration into the central nervous system) or locally to the central nervous system. Peripheral administration includes but is not limited to oral, inhalation, intravenous, intraperitoneal, intra-articular, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation. The route of administration may be dictated by the disease or condition to be treated. For example, if the disease or condition is COPD or IPF, the composition may be administered via inhalation. Alternatively, is the disease or condition is osteoarthritis, the composition may be administered via intra-articular invention. It is within the skill of one in the art, to determine the route of administration based on the disease or condition to be treated. In a specific embodiment, a composition of the invention is administered orally.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16 Ed ISBN: 0-912734-04-3, latest edition, incorporated herein by reference in its entirety, provides a compendium of formulation techniques as are generally known to practitioners.

For therapeutic applications, a therapeutically effective amount of a composition of the invention is administered to a subject. A "therapeutically effective amount" is an amount of the therapeutic composition sufficient to produce a measurable response (e.g., cell death of senescent cells, an anti-aging response, an improvement in symptoms associated with a degenerative disease, or an improvement in symptoms associated with a function-decreasing disorder). Actual dosage levels of active ingredients in a therapeutic composition of the invention can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, age, the age-related disease or condition, the degenerative disease, the function-decreasing disorder, the symptoms, and the physical condition and prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

The frequency of dosing may be daily or once, twice, three times or more per week or per month, as needed as to effectively treat the symptoms. The timing of administration of the treatment relative to the disease itself and duration of treatment will be determined by the circumstances surrounding the case. Treatment could begin immediately, such as at the site of the injury as administered by emergency medical personnel. Treatment could begin in a hospital or clinic itself, or at a later time after discharge from the hospital or after being seen in an outpatient clinic. Duration of treatment could range from a single dose administered on a one-time basis to a life-long course of therapeutic treatments.

Typical dosage levels can be determined and optimized using standard clinical techniques and will be dependent on the mode of administration.

(e) Subject

A subject may be a rodent, a human, a livestock animal, a companion animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the subject is a human.

The human subject may be of any age. However, since senescent cells are normally associated with aging, a human subject may be an older human subject. In some embodiments, the human subject may be about 30, 35, 40, 45, 50, 55, 60, 65, 70, 75, 80, 85, 90, 95 years of age or older. In some preferred embodiments, the human subject is 30 years of age or older. In other preferred embodiments, the human subject is 40 years of age or older. In other preferred embodiments, the human subject is 45 years of age or older. In yet other preferred embodiments, the human subject is 50 years of age or older. In still other preferred embodiments, the human subject is 55 years of age or older. In other preferred embodiments, the human subject is 60 years of age or older. In yet other preferred embodiments, the human subject is 65 years of age or older. In still other preferred embodiments, the human subject is 70 years of age or older. In other preferred embodiments, the human subject is 75 years of age or older. In still other preferred embodiments, the human subject is 80 years of age or older. In yet other preferred embodiments, the human subject is 85 years of age or older. In still other preferred embodiments, the human subject is 90 years of age or older.

Additionally, a subject in need thereof may be a subject suffering from an age-related disease or condition as described below.

(f) Aging and Age-Related Diseases

It has been demonstrated that senescent cells drive age-related pathologies and that selective elimination of these cells can prevent or delay age-related deterioration. Thus, senescent cells may be therapeutic targets in the treatment of aging and age-related disease. As such, removal of senescent cells may delay tissue dysfunction and extend health span. Clearance of senescent cells is expected to improve tissue milieu, thereby improving the function of the remaining non-senescent cells.

The present disclosure provides a method for delaying at least one feature of aging in a subject, the method comprising administering a composition comprising a therapeutically effective amount of PL, a PL derivative, a compound of Formula (I) or a compound of Formula (II) to a subject. As used herein, "a feature of aging" may include, but is not limited to, systemic decline of the immune system, muscle atrophy and decreased muscle strength, decreased skin elasticity, delayed wound healing, retinal atrophy, reduced lens transparency, reduced hearing, osteoporosis, sarcopenia, hair graying, skin wrinkling, poor vision, frailty, and cognitive impairment.

In an aspect, a composition of in the invention selectively kills senescent cells. In this way, targeting senescent cells during the course of aging may be a preventative strategy. Accordingly, administration of a composition comprising a therapeutically effective amount of PL, a PL derivative, a compound of Formula (I) or a compound of Formula (II) to a subject may prevent comorbidity and delay mortality in an older subject. Further, selective killing of senescent cells may boost the immune system, extend the health span, and improve the quality of life in a subject. Additionally, selective killing of senescent cells may delay sarcopenia. Sarcopenia is the degenerative loss of skeletal muscle mass, quality, and strength associated with aging. As such, a delay in sarcopenia may reduce frailty, reduce risk of falling, reduce fractures, and reduce functional disability in a subject. Furthermore, selective killing of senescent cells may delay aging of the skin. Aged skin has increased wrinkles, decreased immune barrier function and increased susceptibility to skin cancer and trauma. As such, selective killing of senescent cells may delay skin wrinkling, delay the onset of decreased immune barrier function and decrease susceptibility to skin cancer and trauma in a subject. Selective killing of senescent cells may also delay the onset of retinal atrophy and reduced lens transparency as measured by vision tests.

Methods of measuring aging are known in the art. For example, aging may be measured in the bone by incident non-vertebral fractures, incident hip fractures, incident total fractures, incident vertebral fractures, incident repeat fractures, functional recovery after fracture, bone mineral density decrease at the lumbar spine and hip, rate of knee buckling, NSAID use, number of joints with pain, and osteoarthritis. Aging may also be measured in the muscle by functional decline, rate of falls, reaction time and grip strength, muscle mass decrease at upper and lower extremities, and dual tasking 10-meter gait speed. Further, aging may be measured in the cardiovascular system by systolic and diastolic blood pressure change, incident hypertension, major cardiovascular events such as myocardial infarction, stroke, congestive heart disease, and cardiovascular mortality. Additionally, aging may be measured in the brain by cognitive decline, incident depression, and incident dementia. Also, aging may be measured in the immune system by rate of infection, rate of upper respiratory infections, rate of flu-like illness, incident severe infections that lead to hospital admission, incident cancer, rate of implant infections, and rate of gastrointestinal infections. Other indications of aging may include, but not limited to, decline in oral health, tooth loss, rate of GI symptoms, change in fasting glucose and/or insulin levels, body composition, decline in kidney function, quality of life, incident disability regarding activities of daily living, and incident nursing home admission. Methods of measuring skin aging are known in the art and may include trans-epidermal water loss (TEWL), skin hydration, skin elasticity, area ratio analysis of crow's feet, sensitivity, radiance, roughness, spots, laxity, skin tone homogeneity, softness, and relief (variations in depth).

The present disclosure also provides a method of treating an age-related disease or condition, the method comprising administering a composition comprising a therapeutically effective amount of PL, a PL derivative, a compound of Formula (I) or a compound of Formula (II) to a subject in need thereof, provided the age-related disease or condition is not cancer. As used herein, "age-related disease or condition" may include, but is not limited to, a degenerative disease or a function-decreasing disorder such as Alzheimer's disease, Parkinson's disease, cataracts, macular degeneration, glaucoma, atherosclerosis, acute coronary syndrome, myocardial infarction, stroke, hypertension, idiopathic pulmonary fibrosis (IPF), chronic obstructive pulmonary disease (COPD), osteoarthritis, type 2 diabetes, obesity, fat dysfunction, coronary artery disease, cerebrovascular disease, periodontal disease, cancer treatment-related disability such as atrophy and fibrosis in various tissues, brain and heart injury, and therapy-related myelodysplastic syndromes, and diseases associated with accelerated aging and/or defects in DNA damage repair and telomere maintenance such as progeroid syndromes (i.e. Hutchinson-Gilford progeria syndrome, Werner syndrome, Bloom syndrome, Rothmund-Thomson Syndrome, Cockayne syndrome, xeroderma pigmentosum, trichothiodystrophy, combined xeroderma pigmentosum-Cockayne syndrome, restrictive dermopathy), ataxia telangiectasia, Fanconi anemia, Friedreich's ataxia, dyskeratosis congenital, aplastic anemia, IPF, and others. Methods of diagnosing and identifying an age-related disease or condition are known in the art.

The present disclosure also provides a method of killing therapy-induced senescent cells. The method comprises administering a composition comprising a therapeutically effective amount of PL or a compound comprising Formula (I) to a subject that has received DNA-damaging therapy and killing therapy induced-senescent cells in normal and tumor tissues following DNA-damaging therapy.

Non-limiting examples of DNA-damaging therapy may include γ-irradiation, alkylating agents such as nitrogen mustards (chlorambucil, cyclophosphamide, ifosfamide, melphalan), nitrosoureas (streptozocin, carmustine, lomustine), alkyl sulfonates (busulfan), triazines (dacarbazine, temozolomide) and ethylenimines (thiotepa, altretamine), platinum drugs such as cisplatin, carboplatin, oxalaplatin, antimetabolites such as 5-fluorouracil, 6-mercaptopurine, capecitabine, cladribine. clofarabine, cytarabine, floxuridine, fludarabine, gemcitabine, hydroxyurea, methotrexate, pemetrexed, pentostatin, thioguanine, anthracyclines such as daunorubicin, doxorubicin, epirubicin, idarubicin, anti-tumor antibiotics such as actinomycin-D, bleomycin, mitomycin-C, mitoxantrone, topoisomerase inhibitors such as topoisomerase I inhibitors (topotecan, irinotecan) and topoisomerase II inhibitors (etoposide, teniposide, mitoxantrone), mitotic inhibitors such as taxanes (paclitaxel, docetaxel), epothilones (ixabepilone), vinca alkaloids (vinblastine, vincristine, vinorelbine) and estramustine.

Based on the observation that ionizing radiation and various chemotherapeutic agents elicit a marked senescence response in vivo, therapy-induced senescent cells may be a cause of long-term ramifications after DNA-damaging therapy, such as cancer therapy. As such, the systemic accumulation of therapy-induced senescent cells may drive accelerated physical decline in cancer survivors. Accelerated physical decline may also be referred to as accelerated aging. Accordingly, once a tumor is removed by systemic radiation or chemotherapy, senescence may be triggered in a variety of other organs, leading to long-term ramifications for the patient. Long-term ramifications may include reduced quality of life predisposing the subject to disabilities and comorbidities. For example, a subject that has received DNA-damaging therapy may experience a disproportionate decline in physical function, such as inability to walk up stairs or to reach up to put things onto shelves and/or increased functional disabilities such as difficulty, eating, dressing and maintaining adequate hygiene. Additionally, late effects of ionizing radiation may include long-term bone marrow injury and/or lung fibrosis. Long-term bone marrow injury can promote hypoplastic anemia and/or myelodysplastic syndrome or leukemia. Further, the inventors demonstrated that following ionizing radiation, senescent cells in lung, muscle and brain are greatly increased. These long-term ramifications provide a link between accelerated aging and cancer treatment. A method to measure accelerated aging may be as described in methods of measuring aging as above. Accordingly, administration of a composition comprising an inhibitor of the invention to a subject may prevent accelerated aging in a subject who has received DNA damaging therapy.

Definitions

"Alkyl" as used herein alone or as part of a group refers to saturated monovalent hydrocarbon radicals having straight or branched hydrocarbon chains or, in the event that at least 3 carbon atoms are present, cyclic hydrocarbons or combinations thereof and contains 1 to 20 carbon atoms (C.sub.1-20alkyl), suitably 1 to 10 carbon atoms (C.sub.1-10alkyl), preferably 1 to 8 carbon atoms (C.sub.1-8alkyl), more preferably 1 to 6 carbon atoms (C.sub.1-4alkyl), and even more preferably 1 to 4 carbon atoms (C.sub.1-4alkyl). Examples of alkyl radicals include methyl, ethyl, propyl, isopropyl, n-butyl, isobutyl, sec-butyl, tert-butyl, pentyl, isoamyl, hexyl, cyclopropyl, cyclobutyl, cyclopentyl, cyclohexyl and the like.

"Alkenyl" as used herein alone or as part of a group refers to monovalent hydrocarbon radicals having a straight or branched hydrocarbon chains having one or more double bonds and containing from 2 to about 18 carbon atoms, preferably from 2 to about 8 carbon atoms, more preferably from 2 to about 5 carbon atoms. Examples of suitable alkenyl radicals include ethenyl, propenyl, alkyl, 1,4-butadienyl and the like.

"Alkynyl" as used herein alone or as part of a group refers to monovalent hydrocarbon radicals having a straight or branched hydrocarbon chains having one or more triple bonds and containing from 2 to about 10 carbon atoms, more preferably from 2 to about 5 carbon atoms. Examples of alkynyl radicals include ethynyl, propynyl, (propargyl), butynyl and the like.

"Aryl" as used herein, alone or as part of a group, includes an organic radical derived from an aromatic hydrocarbon by removal of one hydrogen, and includes monocyclic and polycyclic radicals, such as phenyl, biphenyl, naphthyl.

"Alkoxy" as used herein, alone or as part of a group, refers to an alkyl ether radical wherein the term alkyl is as defined above. Examples of alkyl ether radical include methoxy, ethoxy, n-propoxy, isopropoxy, n-butoxy, isobutoxy, sec-butoxy, tert-butoxy and the like.

"Cycloalkyl" as used herein, alone or in combination, means a saturated or partially saturated monocyclic, bicyclic or tricyclic alkyl radical wherein each cyclic moiety contains from about 3 to about 8 carbon atoms, more preferably from about 3 to about 6 carbon atoms. Examples of such cycloalkyl radicals include cyclopropyl, cyclobutyl, cyclopentyl, cyclohexyl and the like.

"Cycloalkylalkyl" as used herein, alone or in combination, means an alkyl radical as defined above which is substituted by a cycloalkyl radical as defined above. Examples of such cycloalkylalkyl radicals include cyclopropylmethyl, cyclobutyl-methyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl and the like.

"Substituted" means that one or more of the hydrogen atoms bonded to carbon atoms in the chain or ring have been replaced with other substituents. Suitable substituents include monovalent hydrocarbon groups including alkyl groups such as methyl groups and monovalent heterogeneous groups including alkoxy groups such as methoxy groups. "Unsubstituted" means that the carbon chain or ring contains no other substituents other than carbon and hydrogen.

"Branched" means that the carbon chain is not simply a linear chain. "Unbranched" means that the carbon chain is a linear carbon chain.

"Saturated" means that the carbon chain or ring does not contain any double or triple bonds. "Unsaturated" means that the carbon chain or ring contains at least one double bond. An unsaturated carbon chain or ring may include more than one double bond.

"Hydrocarbon group" means a chain of 1 to 25 carbon atoms, suitably 1 to 12 carbon atoms, more suitably 1 to 10 carbon atoms, and most suitably 1 to 8 carbon atoms. Hydrocarbon groups may have a linear or branched chain structure. Suitably the hydrocarbon groups have one branch.

"Carbocyclic group" means a saturated or unsaturated hydrocarbon ring. Carbocyclic groups are not aromatic. Carbocyclic groups are monocyclic or polycyclic. Polycyclic carbocyclic groups can be fused, spiro, or bridged ring systems. Monocyclic carbocyclic groups contain 4 to 10 carbon atoms, suitably 4 to 7 carbon atoms, and more suitably 5 to 6 carbon atoms in the ring. Bicyclic carbocyclic groups contain 8 to 12 carbon atoms, preferably 9 to 10 carbon atoms in the rings.

"Heteroatom" means an atom other than carbon e.g., in the ring of a heterocyclic group or the chain of a heterogeneous group. Preferably, heteroatoms are selected from the group consisting of sulfur, phosphorous, nitrogen and oxygen atoms. Groups containing more than one heteroatom may contain different heteroatoms.

"Heterocyclic group" means a saturated or unsaturated ring structure containing carbon atoms and 1 or more heteroatoms in the ring. Heterocyclic groups are not aromatic. Heterocyclic groups are monocyclic or polycyclic. Polycyclic heteroaromatic groups can be fused, spiro, or bridged ring systems. Monocyclic heterocyclic groups contain 4 to 10 member atoms (i.e., including both carbon atoms and at least 1 heteroatom), suitably 4 to 7, and more suitably 5 to 6 in the ring. Bicyclic heterocyclic groups contain 8 to 18 member atoms, suitably 9 or 10 in the rings.

"Isomer", "isomeric form", "stereochemically isomeric forms" or "stereolsomeric forms", as used herein, defines all possible isomeric as well as conformational forms, made up of the same atoms bonded by the same sequence of bonds but having different three-dimensional structures which are not interchangeable, which compounds or intermediates obtained during said process may possess. Unless otherwise mentioned or indicated, the chemical designation of a compound encompasses the mixture of all possible stereochemically isomeric forms which said compound may possess. Said mixture may contain all diastereoisomers, epimers, enantiomers and/or conformers of the basic molecular structure of said compound. More in particular, stereogenic centers may have the R- or S-configuration, diastereoisomers may have a syn- or anti-configuration, substituents on bivalent cyclic saturated radicals may have either the cis- or trans-configuration and alkenyl radicals may have the E or Z-configuration. All stereochemically isomeric forms of said compound both in pure form or in admixture with each other are intended to be embraced within the scope of the present invention.

EXAMPLES

The following examples illustrate various iterations of the invention. However, those of skill in the art should, in light of the present disclosure, appreciate that many changes can be made in the specific embodiments which are disclosed and still obtain a like or similar result without departing from the spirit and scope of the invention.

Example 1

Figure 1B:
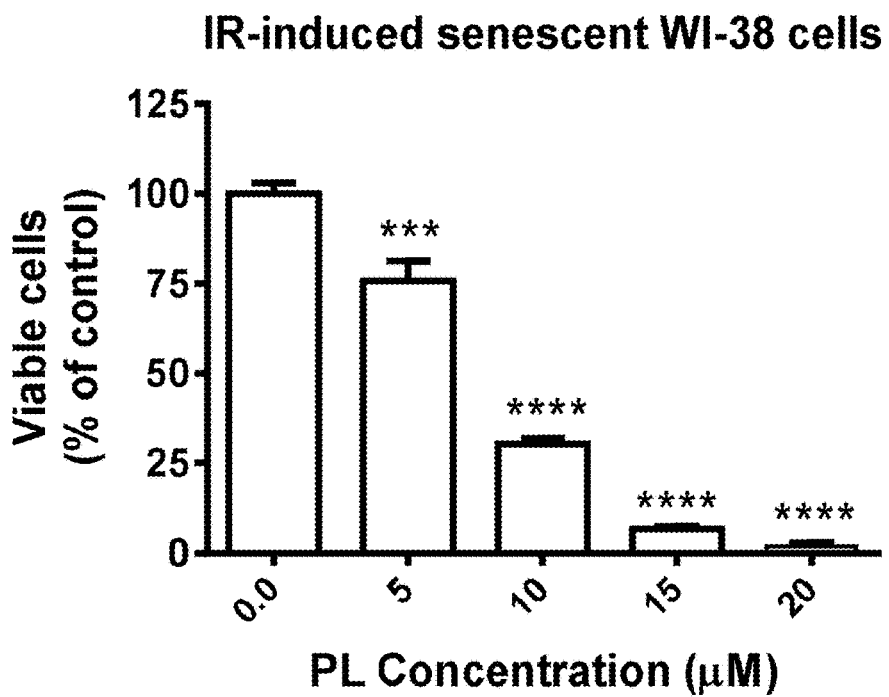
Figure 1C:
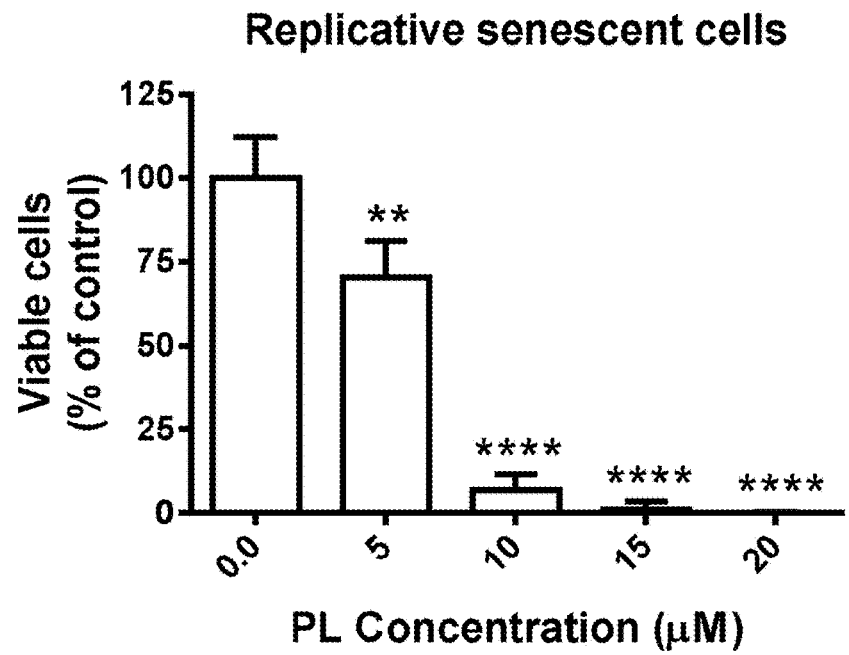
Figure 1D:
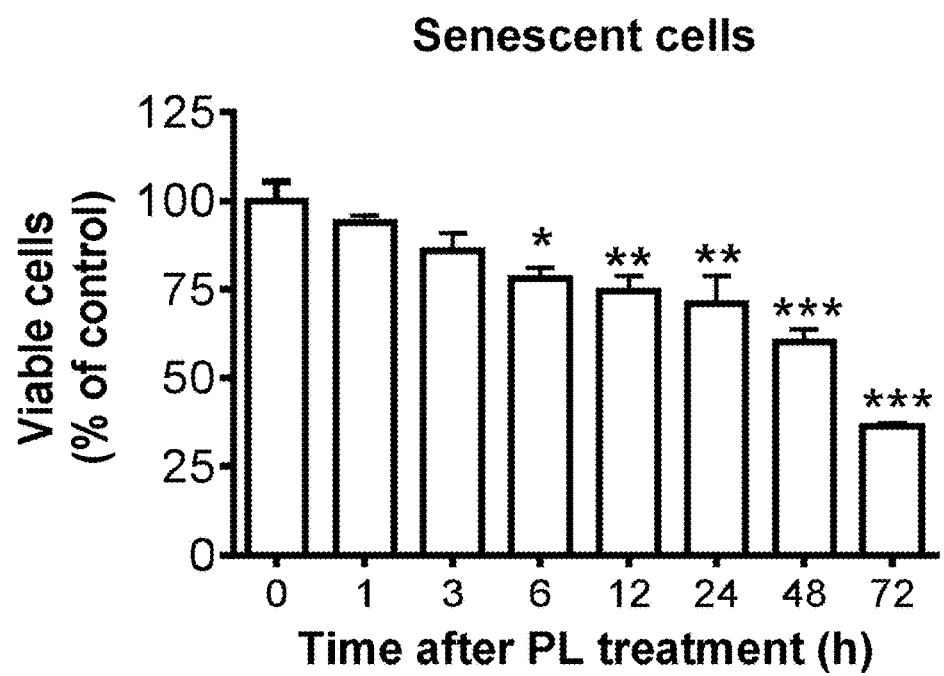
Figure 1E:
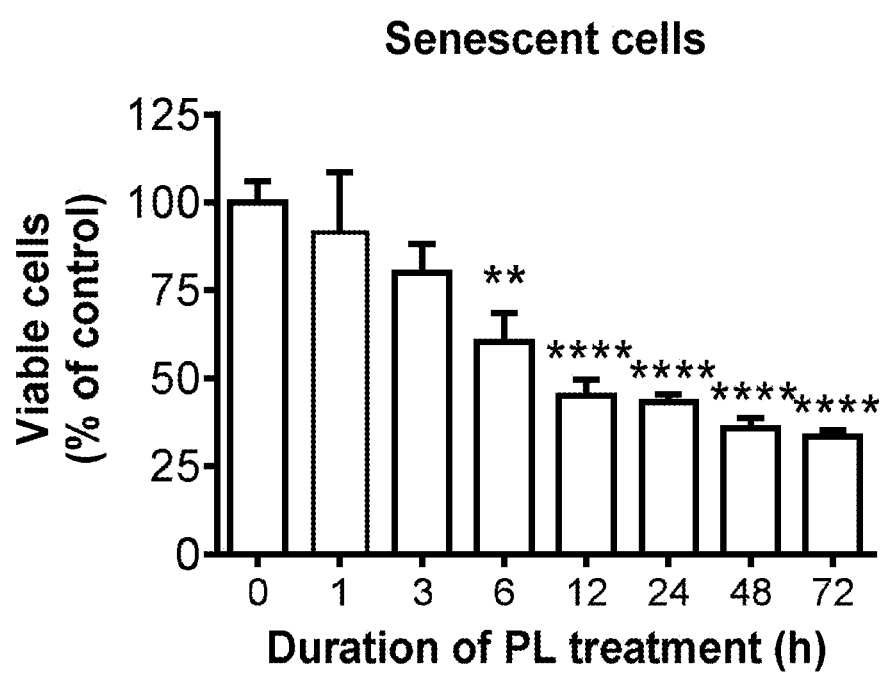

Piperlongumine (PL) Selectively Kills Senescent WI38 Cells in a Dose- and Time-Dependent Manner Normal WI38 cells (FIG. 1A), IR-induced senescent cells (FIG. 1B) and replicative senescent cells (FIG. 1C) were incubated with increasing concentrations of PL. At 72 hours post-treatment cell viability was measured. Concentrations of PL up to 10 µM had no significant effect on normal WI38 cells (FIG. 1A). However, concentrations as low as 5 µM PL significantly reduced the number of viable cells in both IR-induced senescent cells and replicative senescent cells (FIG. 1B, C). IR-induced senescent WI38 cells were treated with 10 µM PL and viable cells were measured at 0, 1, 2, 3, 6, 12, 16, 24, 48 and 72 hours after treatment (FIG. 1D) or the cells were incubated with 10 µM PL for 1, 3, 6, 12, 24, 48 or 72 hours and cell viability was measured at 72 h (FIG. 1E). There was a significant reduction in viable cells from 6 hours on in both treatment scenarios (FIG. 1D, E).

Example 2

PL Selectively Increases ROS Production in Senescent Cells

PL selectively targets senescent cells as measured by the LD50 value. Other ROS target drugs such as auranofin, buthionine sulfoximine, and decyl-triphenylphosphonium have approximately equivalent LD50 values between normal and senescent cells (Table 1).

Figure 2A:
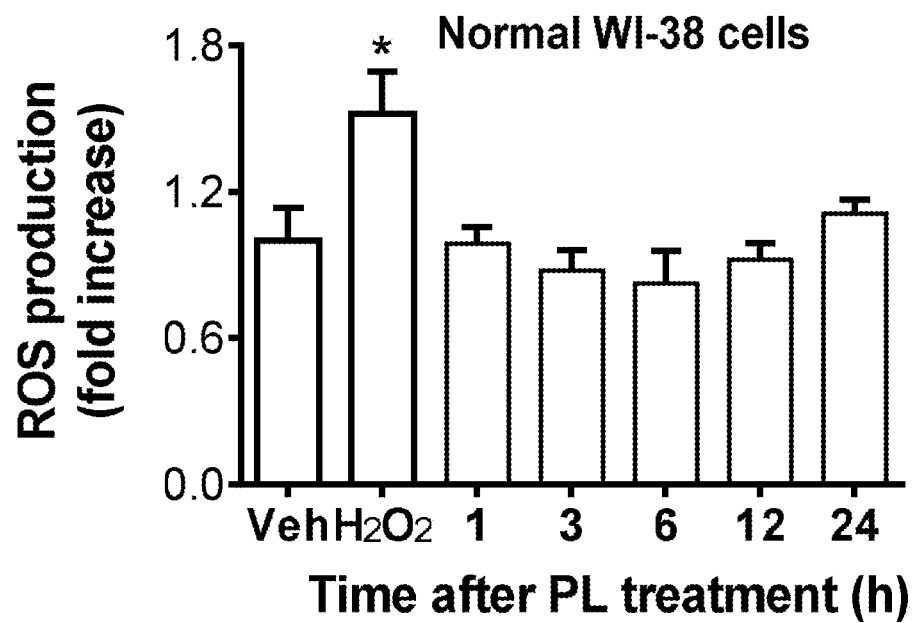
FIG. 2A-B depicts graphs showing PL selectively increases reactive oxygen species (ROS) in senescent WI38 in a time-dependent manner. Normal (FIG. 2A) and IR-induced senescent WI38 cells (FIG. 2B) were incubated with vehicle (Veh), 200 mM $H_2O_2$ for 30 min as a positive control, or 10 µM PL. ROS was measured at various times (1, 3, 6, 12, 24 hours) after PL treatment and expressed as percent of control. Data are presented as mean±SE of three independent assays.
Figure 2B:
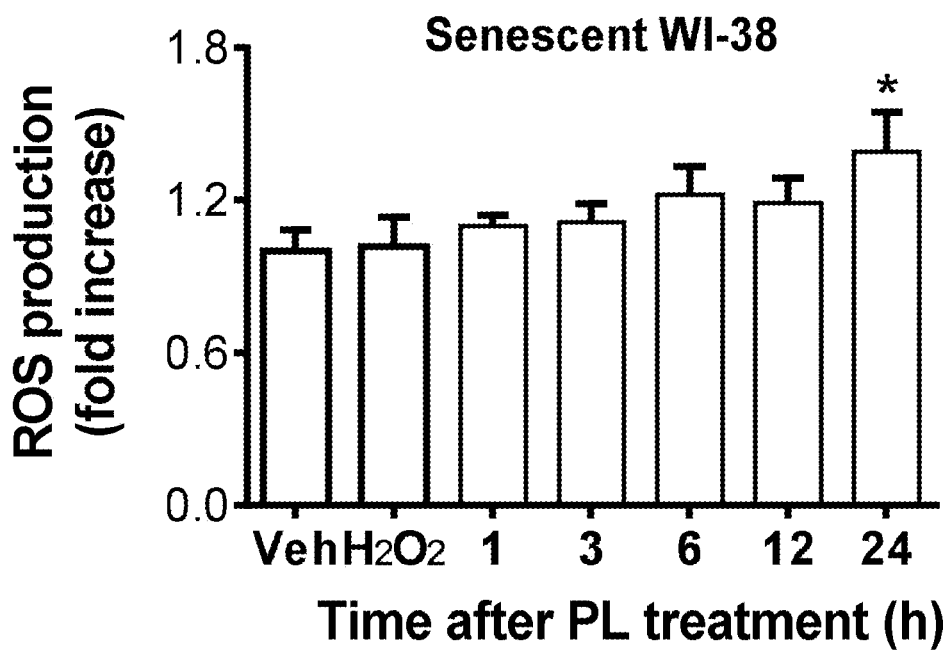

PL selectively increases ROS in senescent WI38 in a time-dependent manner. Normal (FIG. 2A) and IR-induced senescent WI38 cells (FIG. 2B) were incubated with vehicle (Veh), 200 mM $H_2O_2$ for 30 min as a positive control, or 10 µM PL. Reactive oxygen species (ROS) was measured at various times (1, 3, 6, 12, 24 hours) after PL treatment and expressed as percent of control. Data are presented as mean±SE of three independent assays. PL significantly increased ROS production at 24 hours.

TABLE 1

| | LD50 value of ROS target drugs and PL against normal and various senescent WI38 cells. | | | | |
|---|---|---|---|---|---|
| | LD50 (normal) (uM) | LD50 (IR-senescent) (uM) | LD50 (Replicative) (uM) | MOA or Target | Ratio (normal/senescent) |
| Auranofin | 5.13 | 5.34 | Nd | TrxR inhibitor/ROS γ-GSC | 1.0 |
| Buthionine sulfoximine | 2340.19 | 2391.51 | Nd | inhibitor/ROS | 1.0 |
| Decyl-triphenylphosphonium | 1.41 | 0.98 | Nd | Mitochondria/ROS | 1.4 |
| PL | 24.25 | 7.05 | 6.35 | ROS | 3.44-3.82 |

γ-GSC: γ-glutamylcysteine synthetase;
TrxR: Thioredoxin reductase

Example 3

Figure 3A:
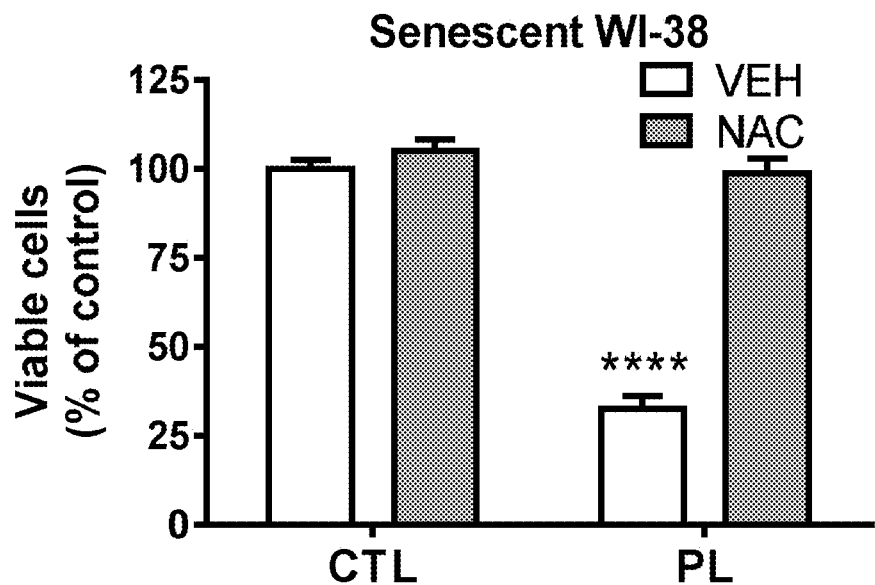
FIG. 3A-B depicts graphs showing IR-induced senescent WI38 cells were pre-treated with (FIG. 3A) the antioxidant NAC (1 mM) or (FIG. 3B) the pan-caspase inhibitor Q-VD-OPh (20 µM) for 2 hours and then incubated with vehicle (VEH) or 10 µM PL for 72 h. Cell viability was measured and expressed as percent of control. Data are presented as mean±SE of three independent assays.
Figure 3B:
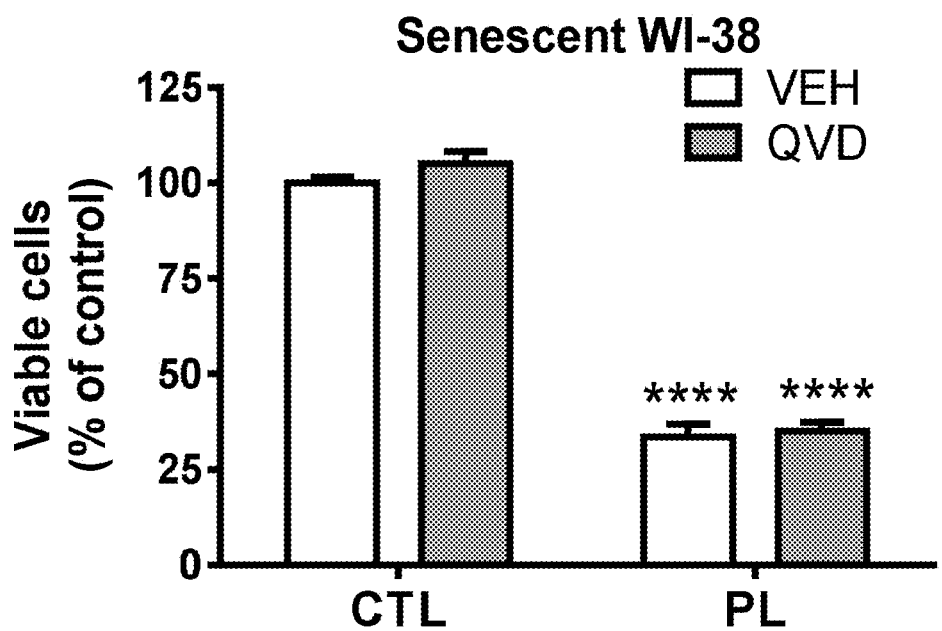

N-Acetyl-Cysteine (NAC) but not the Pan-Caspase Inhibitor QCD Attenuates PL Induced Cell Death in Senescent Cells IR-induced senescent WI38 cells were pre-treated with the pan-caspase inhibitor Q-VD-OPh (20 µM) (FIG. 3B) or the antioxidant NAC (1 mM) (FIG. 3A) for 2 hours and then incubated with vehicle (VEH) or 10 µM PL for 72 h. Cell viability was measured and expressed as percent of control. Data are presented as mean±SE of three independent assays. NAC selectively inhibited PL induced cell death in senescent cells

Example 4

PL and ABT263 Can Synergistically Kill Senescent Cells

Figure 4A:
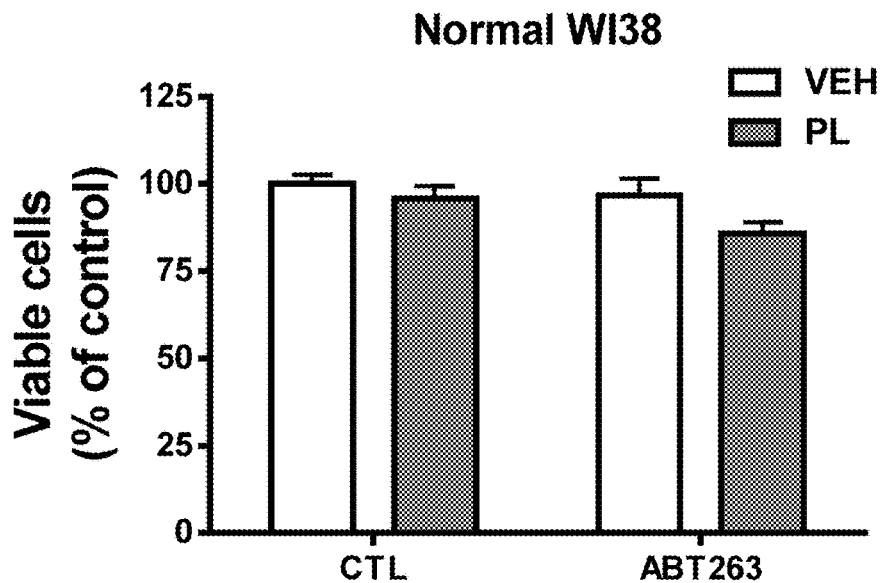
FIG. 4A-C depicts graphs showing PL and ABT263 can synergistically kill senescent cells but have minimal effect on normal cells.
Figure 4B:
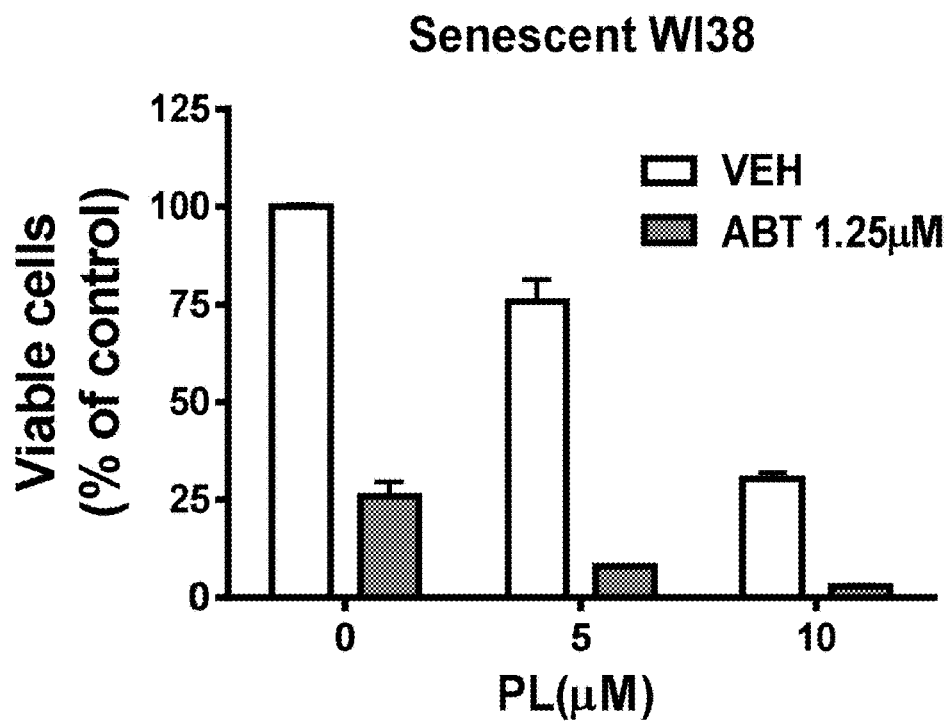
Figure 4C:
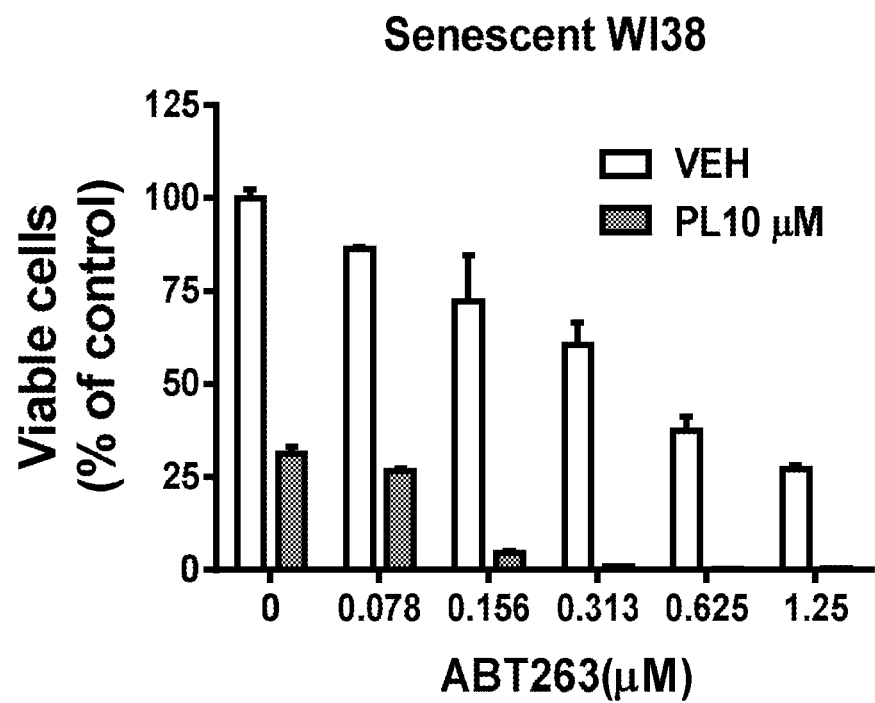

Normal WI38 cells were incubated with vehicle (VEH), 1.25 µM ABT263, PL (10 uM), or both (FIG. 4A). IR-induced senescent WI38 cells were incubated with vehicle (VEH), 1.25 µM ABT263, PL (5 or 10 uM), or both (FIG. 4B). IR-induced senescent WI38 cells were incubated with vehicle (VEH), PL (10 uM), increasing concentrations of ABT263, or both (FIG. 4C). Cell viability was measured at 72 h and expressed as percent of control. Data are presented as mean±SE of three independent assays. The combination of PL and ABT263 synergistically killed senescent cells.

Example 5

Figure 5A:
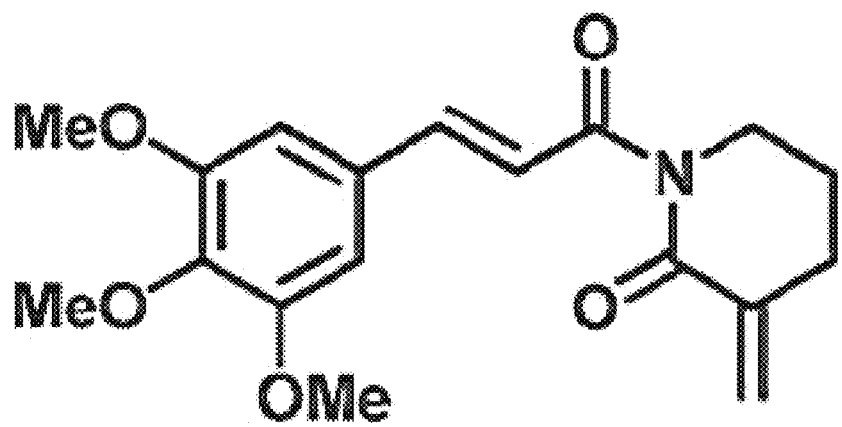
FIG. 5A-C depicts graphs showing PL derivative XL-11155B selectively kills IF-induced senescent WI38 cells but not normal WI38 cells in a dose-dependent manner.
Figure 5B:
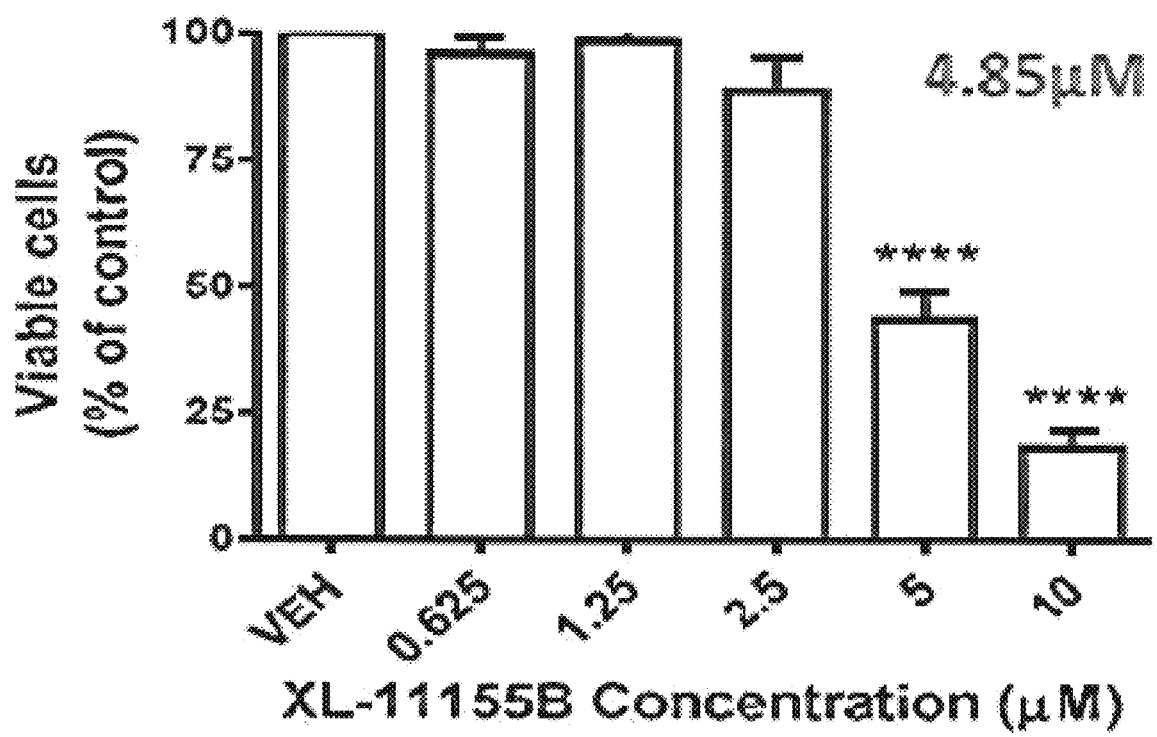
Figure 5C:
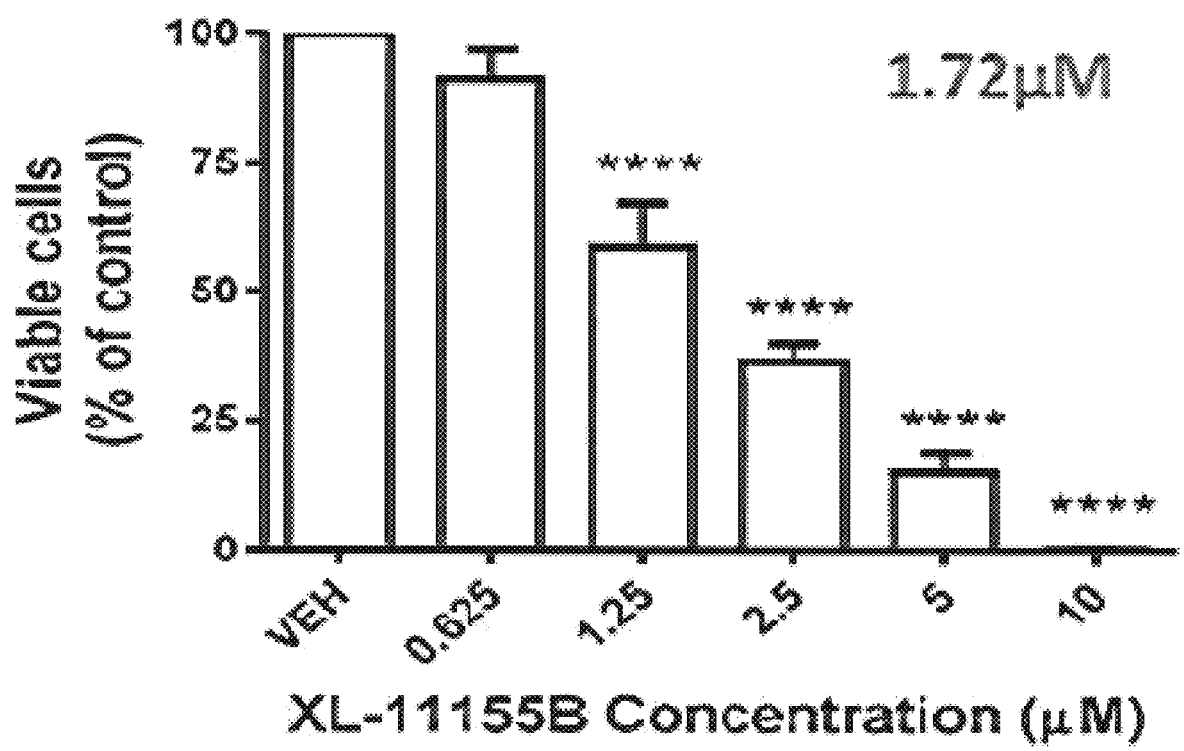

Piperlongumine (PL) Derivative XL-11155B (5) Selectively Kills Senescent WI38 Cells in a Dose- and Time-Dependent Manner Normal WI38 cells (FIG. 5A) and IR-induced senescent cells (FIG. 5B) were incubated with increasing concentrations of XL-11155B. At 72 hours post-treatment cell viability was measured. The $LD_{50}$ of XL-11155B on normal WI38 cells was 4.85 µM (FIG. 5A). However, The $LD_{50}$ of XL-11155B on IR-induced senescent WI38 cells was 1.72 µM (FIG. 5B).

Example 6

Evaluation of Compounds of Formula I and Formula II and Their Ability to Selectively Kill Senescent Cells Normal WI38 cells and IR-induced senescent cells were incubated with increasing concentrations of compounds of Formula I and Formula II. At 72 hours post-treatment cell viability was measured and LD50 was calculated. Table 2 depicts the LD50 values of the compounds of Formula I and compounds of Formula II against normal and IR-induced senescent cells.

TABLE 2

LD50 of compounds of Formula I and Formula II against normal and senescent cells.

| Name | Structure | LD50 (uM) non-senescent cells (NSC) | LD50 (uM) IR-senescent cells (SC) | Ratio (NSC/SC) |
|---|---|---|---|---|
| GZ-11702 | GZ-11702 $C_{17}H_{21}NO_5$ | 169.70 | 208.00 | 0.82 |
| GZ-11718 | GZ-11718 $C_{17}H_{21}NO_5$ | 125.50 | 45.51 | 2.76 |
| XL-11155A | XL-11155A | 34.18 | 9.10 | 3.76 |

TABLE 2-continued

LD50 of compounds of Formula I and Formula II against normal and senescent cells.

| | | LD50 (uM) | | |
| --- | --- | --- | --- | --- |
| Name | Structure | non-senescent cells (NSC) | IR-senescent cells (SC) | Ratio (NSC/SC) |
| GZ-11717B | GZ-11717B<br>$C_{16}H_{17}NO_5$ | 34.25 | 16.11 | 2.13 |
| GZ-11719-by | GZ-11719-by<br>$C_{19}H_{23}NO_5$ | 84.71 | 47.15 | 1.80 |
| GZ-11719 | GZ-11719 | 1.62 | 0.90 | 1.80 |
| XL-11155B | XL-11155B<br>$C_{18}H_{21}NO_5$ | 5.60 | 1.95 | 2.87 |
| XL-11178B | XL-11178B | 12.1 | 7.92 | 1.53 |

TABLE 2-continued

LD50 of compounds of Formula I and Formula II against normal and senescent cells.

| Name | Structure | LD50 (uM) non-senescent cells (NSC) | LD50 (uM) IR-senescent cells (SC) | Ratio (NSC/SC) |
| --- | --- | --- | --- | --- |
| XL-11178A | XL-11178A | >40 | >40 | — |
| XL-11194 | 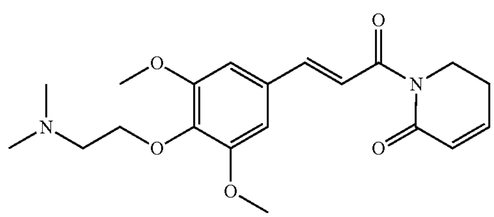 [SMILES: COc1cc(/C=C/C(=O)N2CCC=CC2=O)cc(OC)c1OCCN(C)C] | 10.28 | 4.02 | 2.56 |
| GZ-11725A | 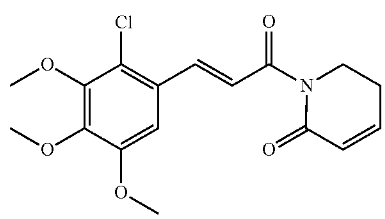 [SMILES: COc1cc(/C=C/C(=O)N2CCC=CC2=O)c(Cl)c(OC)c1OC] | 22.4 | 6.6 | 3.4 |
| GZ-11725B | 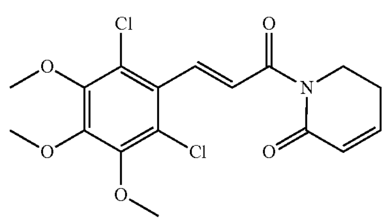 [SMILES: COc1c(Cl)c(/C=C/C(=O)N2CCC=CC2=O)c(Cl)c(OC)c1OC] | 15.73 | 5.35 | 2.94 |
| GZ-11728 | 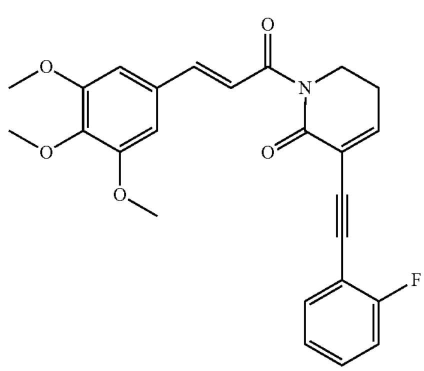 [SMILES: COc1cc(/C=C/C(=O)N2CCC=C(C#Cc3ccccc3F)C2=O)cc(OC)c1OC] | 7.7 | 1.0 | 7.6 |
| XL-12104 | 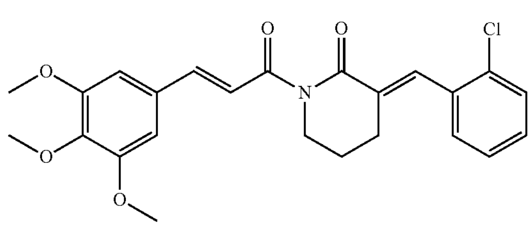 [SMILES: COc1cc(/C=C/C(=O)N2CCC/C(=C\c3ccccc3Cl)C2=O)cc(OC)c1OC] | 4.24 | 1.62 | 2.62 |

TABLE 2-continued
LD50 of compounds of Formula I and Formula II against normal and senescent cells.
| Name | Structure | LD50 (uM) non-senescent cells (NSC) | LD50 (uM) IR-senescent cells (SC) | Ratio (NSC/SC) |
|---|---|---|---|---|
| XZ-12107 | 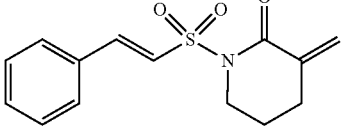 | 23.96 | 4.77 | 5.02 |
| GZ-11734 | 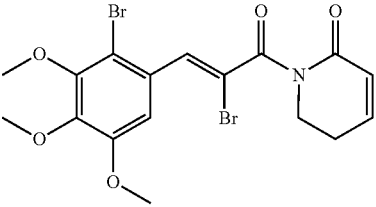 [SMILES: COc1cc(/C=C(\Br)C(=O)N2CCC=CC2=O)c(Br)c(OC)c1OC] | 7.16 | 1.39 | 5.14 |
| XZ-12111B | 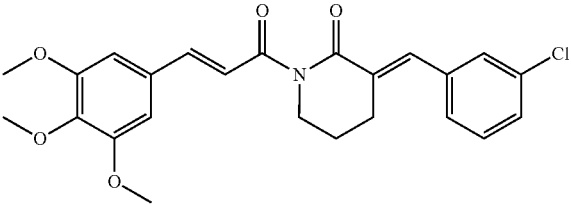 [SMILES: COc1cc(/C=C/C(=O)N2CCC/C(=C\c3cccc(Cl)c3)C2=O)cc(OC)c1OC] | >40 | >40 | — |
| XL-12115 | 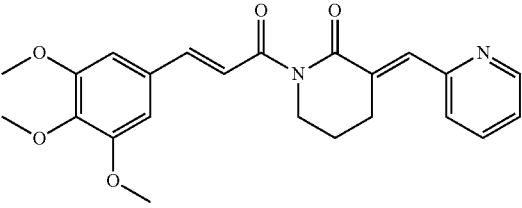 [SMILES: COc1cc(/C=C/C(=O)N2CCC/C(=C\c3ccccn3)C2=O)cc(OC)c1OC] | 52.62 | 30.00 | 1.75 |
| XZ 12040 | 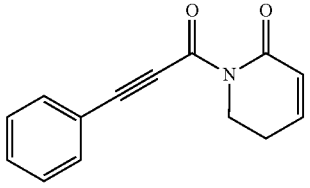 [SMILES: O=C(C#Cc1ccccc1)N1CCC=CC1=O] | 5.78 | 2.4 | 2.41 |
| XZ-12045 | 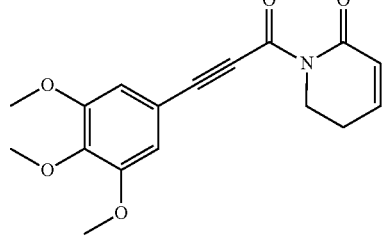 | 13.93 | 4.38 | 3.18 |
| XZ-12047 | 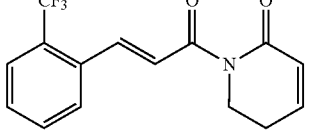 | 21.86 | 10.77 | 2.03 |

TABLE 2-continued

LD50 of compounds of Formula I and Formula II against normal and senescent cells.

| Name | Structure | LD50 (uM) non-senescent cells (NSC) | LD50 (uM) IR-senescent cells (SC) | Ratio (NSC/SC) |
| --- | --- | --- | --- | --- |
| XZ 12043 | XZ12043 | 23.53 | 15.71 | 1.50 |
| XZ-12041 | 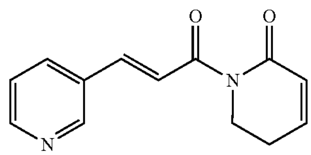 | 22.07 | 9.97 | 2.21 |
| XZ-12052 | XZ12052 | 80.00 | 41.04 | 1.95 |
| XL-12128 | 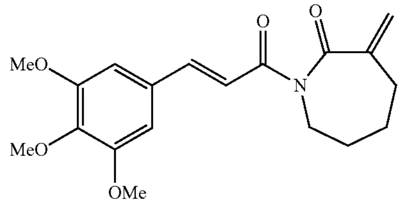 | 1.95 | 0.67 | 2.91 |
| XL-12124 | 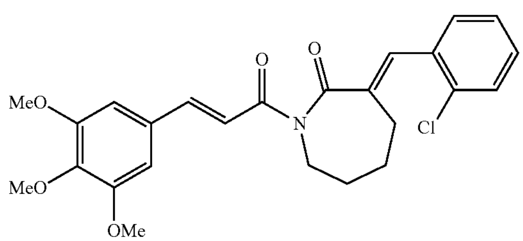 | ND | ND | — |
| XZ-12208 | XZ12208 | 10.16 | 2.66 | 3.82 |
| XZ-12209 | XZ12209 | 9.02 | 5.40 | 1.67 |

TABLE 2-continued
LD50 of compounds of Formula I and Formula II against normal and senescent cells.
| Name | Structure | LD50 (uM) non-senescent cells (NSC) | LD50 (uM) IR-senescent cells (SC) | Ratio (NSC/SC) |
|---|---|---|---|---|
| XZ-12210 | 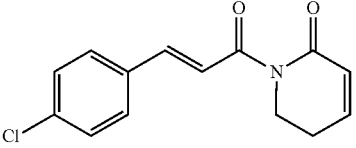 XZ12210 | 7.31 | 3.92 | 1.91 |
| XZ-12213 | 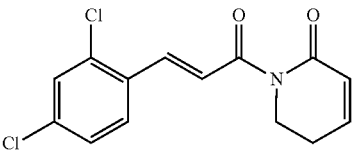 XZ12213 | 4.85 | 4.00 | 1.21 |
| XZ-12215 | 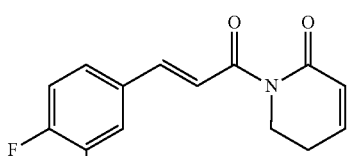 XZ12215 | 12.35 | 9.478 | 1.30 |
| XZ-12216 | 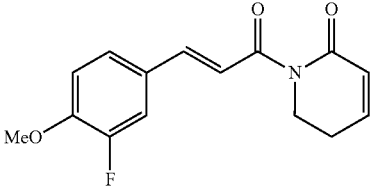 XZ12216 | 8.74 | 5.18 | 1.69 |
| PS-12611 | 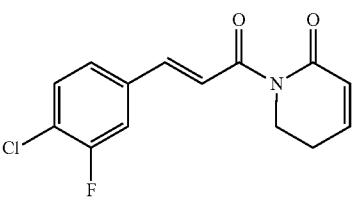 PS12611 | 8.48 | 6.13 | 1.38 |
| PS-12612 | 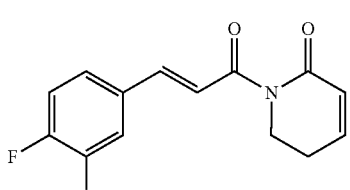 PS12612 | 8.58 | 5.86 | 1.46 |

TABLE 2-continued
LD50 of compounds of Formula I and Formula II against normal and senescent cells.
| Name | Structure | LD50 (uM) non-senescent cells (NSC) | LD50 (uM) IR-senescent cells (SC) | Ratio (NSC/SC) |
|---|---|---|---|---|
| PS-12626 | 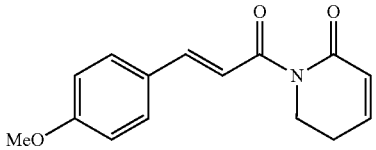 PS-12626 | 4.51 | 1.20 | 3.77 |
| PS-12624 | 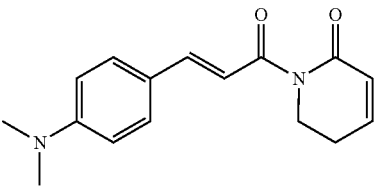 PS-12624 | 15.75 | 12.90 | 1.22 |
| PS-12636 | 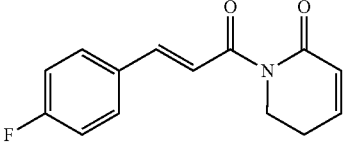 PS-12636 | 18.78 | 6.76 | 2.78 |
| PS-12633 | 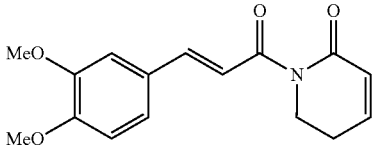 PS-12633 | 21.04 | 8.33 | 2.53 |
| PS-12634 | 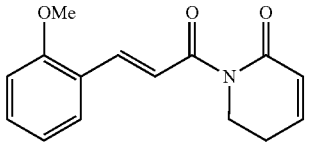 PS-12634 | 7.67 | 7.11 | 1.08 |
| PS-12637 | 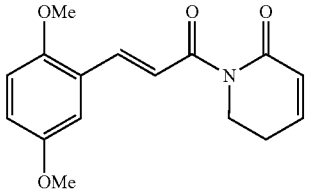 PS-12637 | 17.50 | 6.41 | 2.73 |
| PS-12638 | 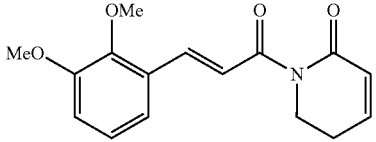 PS-12638 | 20.14 | 7.10 | 2.84 |

TABLE 2-continued

LD50 of compounds of Formula I and Formula II against normal and senescent cells.

| Name | Structure | LD50 (uM) non-senescent cells (NSC) | LD50 (uM) IR-senescent cells (SC) | Ratio (NSC/SC) |
|---|---|---|---|---|
| PS-12639 | (2,6-dimethoxycinnamoyl-dihydropyridinone) | 13.46 | 6.47 | 2.08 |
| PS-12640 | (3,5-dimethoxycinnamoyl-dihydropyridinone) | 14.37 | 7.72 | 1.86 |
| XZ-12237 | (4-acetamidocinnamoyl-dihydropyridinone) | 12.67 | 5.32 | 2.38 |
| XZ-12224 | (4-nitrocinnamoyl-dihydropyridinone) | 6.41 | 2.20 | 2.92 |
| XZ-12235 | (4-aminocinnamoyl-dihydropyridinone) | 12.85 | 7.77 | 1.65 |
| XL-12137A | (3,4,5-trimethoxycinnamoyl-isobutylidenepiperidinone) | >40 | >40 | — |

TABLE 2-continued
LD50 of compounds of Formula I and Formula II against normal and senescent cells.
| Name | Structure | LD50 (uM) non-senescent cells (NSC) | LD50 (uM) IR-senescent cells (SC) | Ratio (NSC/SC) |
|---|---|---|---|---|
| XL-12137B | 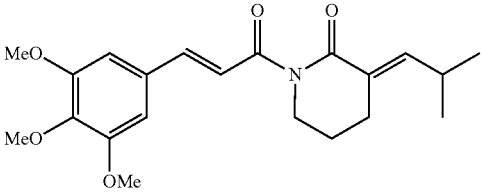 XZ-12137B | >40 | >40 | — |
| XL-12138 | 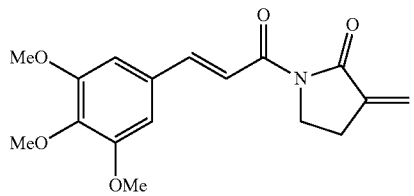 XZ-12138 | 12.41 | 2.09 | 5.93 |
| PS-12644 | 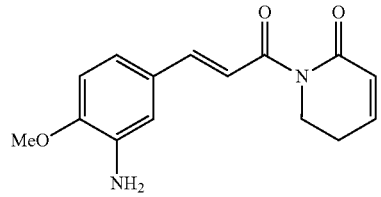 PS-12644 | 24.20 | 18.99 | 1.27 |
| PS-12643 | 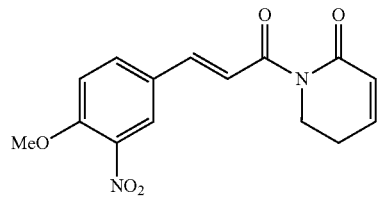 PS-12643 | 15.41 | 6.74 | 2.28 |
| PS-12641 | 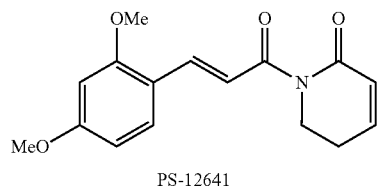 [SMILES: COc1ccc(/C=C/C(=O)N2CCC=CC2=O)c(OC)c1] PS-12641 | 3.73 | 5.12 | 0.73 |
| PS-12646 | 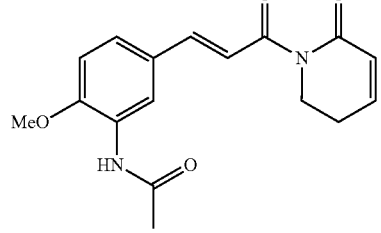 PS-12646 | 35.34 | 18.57 | 1.90 |

TABLE 2-continued

LD50 of compounds of Formula I and Formula II against normal and senescent cells.

| Name | Structure | LD50 (uM) non-senescent cells (NSC) | LD50 (uM) IR-senescent cells (SC) | Ratio (NSC/SC) |
|---|---|---|---|---|
| PS-12654 | PS-12654 | 22.10 | 17.02 | 1.30 |

Example 7

Synthesis of Exemplary Piperlongumine Derivatives of Formula (I)

General Method:

To a solution of acid (1 eq) in dry THF was added Et$_3$N (1.15 eq) and pivaloyl chloride (1.1 eq). The reaction mixture was stirred for 45-60 min for completion (monitored by TLC). The mixture was filtered and the filtrat was used directly for the next step.

To a stirred solution of 5,6-dihydropyridin-2(1H)-one (0.8 eq) in dry THF was added 0.88 eq of n-BuLi under inert atmosphere at −78° C. After stirred for 0.5 h, the mixed anhydride solution prepared from above was added and the resulting reaction mixture was stirred for 1 h before quenched with saturated NH$_4$Cl (0.5 mL). The mixture was extracted with ethylacetate (10 mL×3). The organic phases were combined, washed with sat. NaCl, dried over anhydrous Na$_2$SO$_4$, and evaporated to dryness under vacuum. The product was purified by silica gel column chromatography.

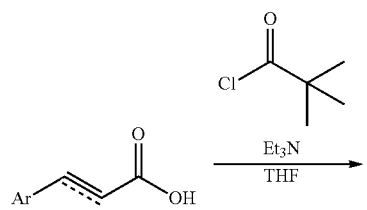

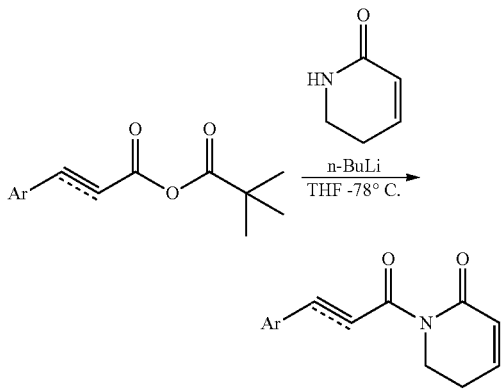

Preparation of (E)-1-(3-(3-fluoro-4-chlorophenyl)prop-2-enoyl)-5,6-dihydropyridin-2(1H)-one

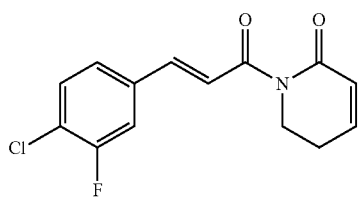

PS12611

Yield: 28%; yellow solid. $^1$H-NMR (400 MHz, CDCl$_3$) δ 7.61 (d, J=15.6 Hz, 1H), 7.46 (d, J=15.6 Hz, 1H), 7.41-7.27 (m, 3H), 6.96 (m, 1H), 6.05 (dd, J=9.6, 2 Hz, 1H), 4.04 (t, J=6 Hz, 2H), 2.49 (m, 2H) ppm; $^{13}$C-NMR (100 MHz, CDCl$_3$) δ 168.39, 165.75, 159.43, 156.95, 145.76, 140.68 (d, J=2.3 Hz), 135.74 (d, J=7.6 Hz), 130.88, 125.64, 124.72 (d, J=3 Hz), 123.66, 122.44 (d, J=18 Hz), 115.55 (d, J=21.3 Hz), 41.60, 24.72 ppm.

Preparation of (E)-1-(3-(3-chloro-4-fluorophenyl)prop-2-enoyl)-5,6-dihydropyridin-2(1H)-one

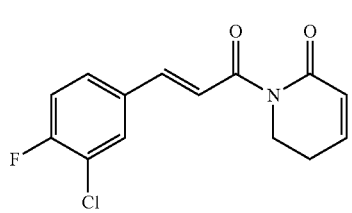

PS12612

Yield: 30%; yellow solid. ¹H-NMR (400 MHz, CDCl₃) δ 7.61 (m, 2H), 7.42 (m, 2H), 7.13 (t, J=8.8 Hz, 1H), 6.96 (m, 1H), 6.05 (m, 1H), 4.03 (t, J=6.8 Hz, 2H), 2.48 (m, 2H) ppm; ¹³C-NMR (100 MHz, CDCl₃) δ 168.42, 165.77, 160.10, 157.58, 145.74, 140.62 (d, J=1.6 Hz), 132.45 (d, J=4.6 Hz), 130.05, 128.22 (d, J=7.5 Hz), 125.64, 122.93 (d, J=2.3 Hz), 121.59 (d, J=18.2 Hz), 116.94 (d, J=11 Hz), 41.59, 24.73 ppm.

Preparation of (E)-1-(3-(3,4-dimethoxylphenyl)prop-2-enoyl)-5,6-dihydropyridin-2(1H)-one

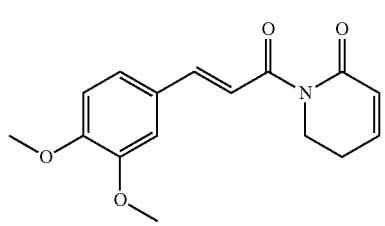

PS12633

Yield: 58%; yellow solid. ¹H-NMR (400 MHz, CDCl₃) δ 7.71 (d, J=15.6 Hz, 1H), 7.40 (d, J=15.2 Hz, 1H), 7.15 (dd, J=8.4, 2 Hz, 1H), 7.10 (d, J=0.8 Hz, 1H), 6.92 (m, 1H), 6.84 (d, J=8.4 Hz, 1H), 6.04 (m, 1H), 4.03 (t, J=6 Hz, 2H) 3.90 (s, 6H), 2.46 (m, 2H) ppm.

Preparation of (E)-1-(3-(2,5-dimethoxylphenyl)prop-2-enoyl)-5,6-dihydropyridin-2(1H)-one

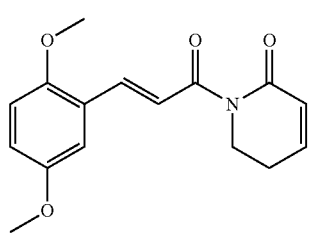

PS12637

Yield: 31%; yellow solid. ¹H-NMR (400 MHz, CDCl₃) δ 8.05 (d, J=15.6 Hz, 1H), 7.52 (d, J=15.6 Hz, 1H), 7.11 (d, J=2.8 Hz, 1H), 6.90 (m, 2H), 6.83 (d, J=8.8 Hz, 1H), 6.03 (d, J=10 Hz, 1H), 4.02 (m, 2H), 3.83 (s, 3H), 3.78 (s, 3H), 2.45 (m, 2H) ppm.

Preparation of (E)-1-(3-(2,3-dimethoxylphenyl)prop-2-enoyl)-5,6-dihydropyridin-2(1H)-one

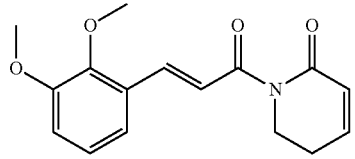

PS12638

Yield: 57%; yellow solid. ¹H-NMR (400 MHz, CDCl₃) δ 8.03 (d, J=15.6 Hz, 1H), 7.51 (d, J=16 Hz, 1H), 7.21 (d, J=8 Hz, 1H), 7.02 (m, 1H), 6.90 (d, J=7.6 Hz, 2H), 6.00 (dd, J=9.6, 1.6 Hz, 1H), 4.01 (m, 2H), 3.85 (s, 6H), 2.45 (m, 2H) ppm; ¹³C-NMR (100 MHz, CDCl₃) δ 169.10, 165.75, 153.04, 148.53, 145.46, 138.06, 129.25, 125.76, 124.05, 123.08, 119.60, 113.71, 61.38, 55.82, 41.59, 24.76 ppm.

Preparation of (E)-1-(3-(2,6-dimethoxylphenyl)prop-2-enoyl)-5,6-dihydropyridin-2(1H)-one

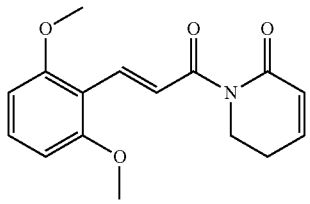

PS12639

Yield: 46%; yellow solid. ¹H-NMR (400 MHz, CDCl₃) δ 8.13 (d, J=16 Hz, 1H), 7.82 (d, J=16 Hz, 1H), 7.17 (m, 1H), 6.81 (m, 1H), 6.46 (dd, J=8.4, 4.4 Hz, 2H), 5.94 (d, J=10 Hz, 1H), 3.94 (m, 2H), 3.80 (s, 6H), 2.37 (m, 2H) ppm; ¹³C-NMR (100 MHz, CDCl₃) δ 170.50, 165.68, 160.09, 145.00, 134.72, 130.99, 125.99, 124.16, 112.99, 103.65, 103.61, 55.79, 55.74, 41.66, 24.80 ppm. GC-MS: 287.1 (M⁺).

Preparation of (E)-1-(3-(3,5-dimethoxylphenyl)prop-2-enoyl)-5,6-dihydropyridin-2(1H)-one

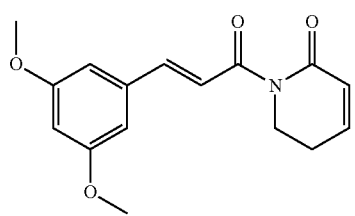

PS12640

Yield: 66%; yellow solid. ¹H-NMR (400 MHz, CDCl₃) δ 7.63 (d, J=15.6 Hz, 1H), 7.43 (d, J=15.6 Hz, 1H), 6.91 (m, 1H), 6.69 (d, J=2.4 Hz, 2H), 6.45 (m, 1H), 6.00 (m, 1H), 4.00 (t, J=6.4 Hz, 2H), 3.78 (s, 6H), 2.44 (m, 2H) ppm; ¹³C-NMR (100 MHz, CDCl₃) δ 168.84, 165.75, 160.87, 145.61, 143.49, 136.93, 125.67, 122.28, 106.09, 102.47, 55.38, 41.60, 24.73 ppm. GC-MS: 287.1 (M⁺).

Preparation of (E)-1-(3-(2,4-dimethoxylphenyl)prop-2-enoyl)-5,6-dihydropyridin-2(1H)-one

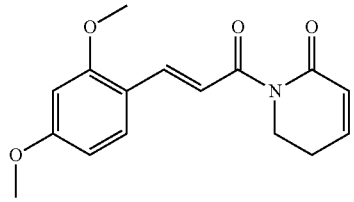

PS12641

Yield: 53%; yellow solid. $^1$H-NMR (400 MHz, CDCl$_3$) δ 8.03 (d, J=15.6 Hz, 1H), 7.51 (m, 2H), 6.89 (m, 1H), 6.48 (dd, J=8.4, 2.4 Hz, 1H), 6.42 (d, J=2.4 Hz, 1H), 6.02 (m, 1H), 4.01 (m, 2H), 3.85 (s, 3H), 3.82 (s, 3H), 2.44 (m, 2H) ppm; $^{13}$C-NMR (100 MHz, CDCl$_3$) δ 169.60, 165.78, 162.62, 159.90, 145.06, 139.20, 130.32, 126.00, 119.54, 117.30, 105.15, 98.29, 55.48, 55.41, 41.60 24.80 ppm.

Preparation of (E)-1-(3-(3-nitro-4-methoxylphenyl)prop-2-enoyl)-5,6-dihydropyridin-2(1H)-one

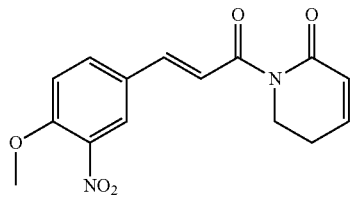

PS12643

Yield: 47%; yellow solid. $^1$H-NMR (400 MHz, CDCl$_3$) δ 8.03 (d, J=2.4 Hz, 1H), 7.74 (dd, J=8.4, 2.4 Hz, 1H), 7.64 (d, J=15.6 Hz, 1H), 7.44 (d, J=15.6 Hz, 1H), 7.08 (d, J=8.8 Hz, 1H), 6.96 (m, 1H), 6.04 (m, 1H), 4.03 (m, 2H), 3.99 (s, 3H), 2.48 (m, 2H) ppm; $^{13}$C-NMR (100 MHz, CDCl$_3$) δ 168.42, 165.78, 153.78, 145.74, 140.29, 139.80, 133.58, 127.88, 125.65, 122.47, 113.69, 56.71, 41.63, 24.74 ppm.

Preparation of (E)-1-(3-(3-amino-4-methoxylphenyl)prop-2-enoyl)-5,6-dihydropyridin-2(1H)-one

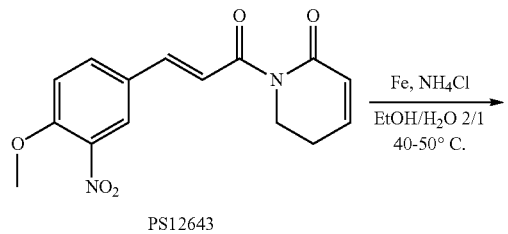

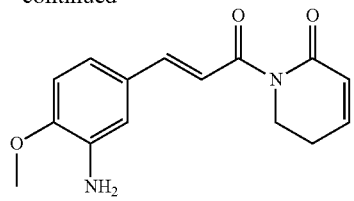

PS12644

A mixture of PS12643 (92 mg, 305 mmol), Fe (68.2 mg, 1.22 mol), and NH$_4$Cl (65.2 mg, 1.2 mol) in 6 mL of EtOH and 3 mL H$_2$O was reacted at 40-50° C. for 3 h. After the completion of the reaction (monitored by TLC), the reaction was cooled to rt, neutralized with sat. NaHCO$_3$, extracted with dichloromethane. The organic phase was washed with brine, dried over anhydrous Na$_2$SO$_4$, and evaporated to dryness under vacuum. The product was purified by silica gel column chromatography to afford the target compound (74 mg) as a yellow solid, yield: 90%. $^1$H-NMR (400 MHz, CDCl$_3$) δ 7.66 (d, J=15.6 Hz, 1H), 7.36 (d, J=15.6 Hz, 1H), 6.99-6.89 (m, 3H), 6.77 (d, J=10.8 Hz, 1H), 6.03 (m, 1H), 4.02 (m, 2H), 3.86 (s, 3H), 2.45 (m, 2H) ppm; $^{13}$C-NMR (100 MHz, CDCl$_3$) δ 169.16, 165.82, 149.31, 145.22, 144.35, 136.28, 128.16, 125.94, 120.78, 119.09, 113.33, 110.03, 55.52, 41.55, 24.79 ppm.

Preparation of (E)-1-(3-(3-acetylamino-4-methoxylphenyl)prop-2-enoyl)-5,6-dihydropyridin-2(1H)-one

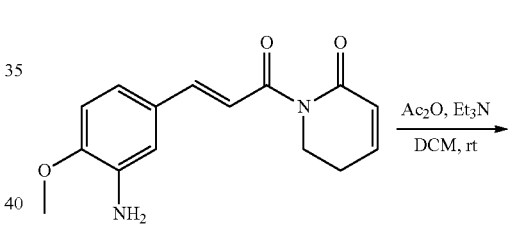

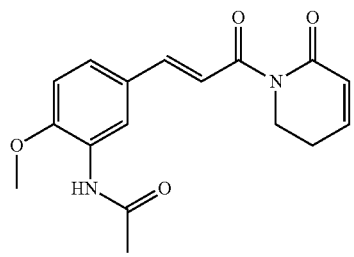

PS12646

A mixture of PS12644 (68 mg, 0.25 mmol), Ac$_2$O (35 μL, 0.37 mmol), and Et$_3$N (52 μL, 0.37 mmol) in dichloromethane was allowed stirred at rt overnight. After the completion of the reaction (monitored by TLC), the reaction was extracted with dichloromethane and water. The organic phase was washed with brine, dried over anhydrous Na$_2$SO$_4$, and evaporated to dryness under vacuum. The product was purified by silica gel column chromatography to afford the target compound (55 mg) as a yellow solid, yield: 70%. $^1$H-NMR (400 MHz, CDCl$_3$) δ 8.60 (s, 1H), 7.70 (m, 2H), 7.36 (d, J=15.6 Hz, 1H), 7.28 (d, J=2.4 Hz, 1H), 6.91 (m, 1H), 6.84 (d, J=8.8 Hz, 1H), 6.02 (d, J=10 Hz, 1H), 4.01 (s, 2H), 3.90 (s, 3H), 2.45 (m, 2H), 2.20 (s, 3H) ppm; $^{13}$C-NMR (100 MHz, CDCl$_3$) δ 169.14, 168.11, 165.69, 149.12, 145.17, 143.52, 128.35, 127.89, 125.88, 124.04, 120.39, 119.84, 109.88, 55.83, 41.63, 24.88, 24.80 ppm. GC-MS: 313.1 (M$^+$).

Preparation of (E)-1-(3-(4-dimethylaminophenyl) prop-2-enoyl)-5,6-dihydropyridin-2(1H)-one

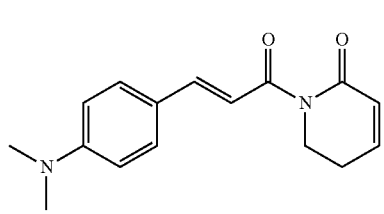
PS12627

Yield: 52%; yellow solid. $^1$H-NMR (400 MHz, CDCl$_3$) δ 7.75 (d, J=15.6 Hz, 1H), 7.48 (d, J=8.4 Hz, 1H), 7.36 (d, J=16 Hz, 1H), 6.89 (m, 1H), 6.65 (d, J=8.8 Hz, 2H), 6.03 (m, 1H), 4.02 (t, J=6.4 Hz, 2H), 3.01 (s, 6H), 2.44 (m, 2H) ppm; $^{13}$C-NMR (100 MHz, CDCl$_3$) δ 169.45, 165.84, 151.70, 144.96, 144.94, 130.14, 126.09, 122.96, 116.29, 111.71, 41.57, 40.12, 24.82 ppm.

Preparation of (E)-1-(3-(1-acetyl-1H-indol-3-yl) prop-2-enoyl)-5,6-dihydropyridin-2(1H)-one

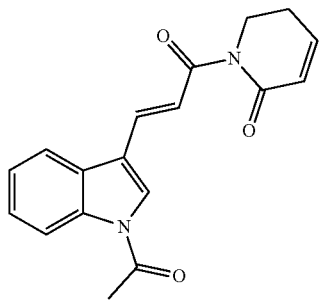
PS12654

Yield: 25%; yellow solid. $^1$H-NMR (400 MHz, CDCl$_3$) δ 8.45 (d, J=8 Hz, 1H), 7.93-7.86 (m, 2H), 7.75-7.69 (m, 2H), 7.38 (m, 2H), 6.95 (m, 1H), 6.06 (d, J=9.6 Hz, 1H), 4.07 (m, 2H), 2.65 (s, 3H), 2.48 (m, 2H) ppm; $^{13}$C-NMR (100 MHz, CDCl$_3$) δ 168.85, 168.40, 165.86, 145.50, 136.57, 134.96, 127.97, 127.60, 126.00, 125.87, 124.57, 121.96, 120.37, 119.13, 116.75, 41.56, 24.77, 23.98 ppm.

Preparation of (E)-1-(3-(pyridine-2-yl)prop-2-enoyl)-5,6-dihydropyridin-2(1H)-one

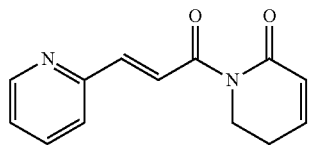
PS12665

Yield: 44%; yellow solid. $^1$H-NMR (400 MHz, CDCl$_3$) δ 8.61 (d, J=4 Hz, 1H), 7.80 (d, J=15.2 Hz, 1H), 7.68-7.64 (m, 2H), 7.45 (d, J=8 Hz, 1H), 7.20 (dd, J=7.6, 4.8 Hz, 1H), 6.92 (m, 1H), 6.01 (d, J=9.6 Hz, 1H), 4.00 (m, 2H), 2.45 (m, 2H) ppm. GC-MS: 228.1 (M$^+$).

Preparation of (E)-1-(3-(pyridine-3-yl)prop-2-enoyl)-5,6-dihydropyridin-2(1H)-one

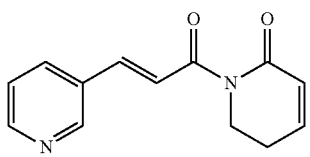
XZ12041

Yield 61%; yellow solid. $^1$H NMR (400 MHz, CDCl$_3$) δ 8.77 (d, J=2.0 Hz, 1H), 8.58 (dd, J=4.8, 1.6 Hz, 1H), 7.92-7.89 (m, 1H), 7.70 (d, J=15.6 Hz, 1H), 7.56 (d, J=15.6 Hz, 1H), 7.34-7.30 (m, 1H), 6.99-6.95 (m, 1H), 6.07-6.03 (m, 1H), 4.05 (t, J=6.4 Hz, 2H), 2.52-2.47 (m, 2H) ppm; $^{13}$C NMR (100 MHz, CDCl$_3$) δ 168.3, 165.7, 150.6, 149.9, 145.8, 139.3, 134.2, 130.8, 125.6, 124.0, 123.6, 41.6, 24.7 ppm Preparation of (E)-1-(3-(furan-3-yl)prop-2-enoyl)-5, 6-dihydropyridin-2(1H)-one

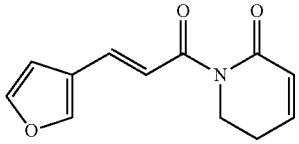
XZ12043

Yield 62%; $^1$H NMR (400 MHz, CDCl$_3$) δ 7.53-7.35 (m, 3H), 6.95-6.91 (m, 1H), 6.63 (d, J=3.2 Hz, 1H), 6.47-6.45 (m, 1H), 6.05-6.01 (m, 1H), 4.02 (t, J=6.4 Hz, 2H), 2.49-2.43 (m, 2H) ppm; $^{13}$C NMR (100 MHz, CDCl$_3$) δ 168.7, 165.6, 151.6, 145.4, 144.5, 130.1, 125.7, 119.4, 114.7, 112.2, 41.6, 24.7 ppm; GC-MS 217 (M$^+$)

Preparation of (E)-1-(3-(2-(trifluoromethyl)phenyl) prop-2-enoyl)-5,6-dihydropyridin-2(1H)-one

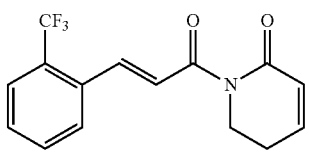
XZ12047

Yield 21%; yellow solid. $^1$H NMR (400 MHz, CDCl$_3$) δ 8.08-8.03 (m, 1H), 7.79 (d, J=7.6 Hz, 1H), 7.67 (d, J=7.6 Hz, 1H), 7.56-7.40 (m, 3H), 6.97-6.92 (m, 1H), 6.05-6.01 (m, 1H), 4.04 (t, J=6.4 Hz, 2H), 2.50-2.45 (m, 2H) ppm.

Preparation of (E)-2-(6-oxo-1,2,3,6-tetrahydropyridine-1-carbonyl)-3-(3,4,5-trimethoxyphenyl)acrylonitrile

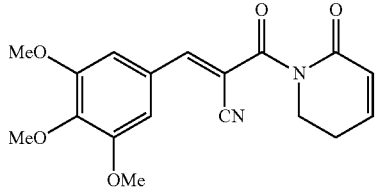

Yield 19%; ¹H NMR (400 MHz, CDCl₃) δ 7.75 (s, 1H), 7.19 (s, 2H), 6.97-6.91 (m, 1H), 6.04-6.00 (m, 1H), 3.89-3.84 (m, 11H), 2.55-2.50 (m, 2H) ppm; ¹³C NMR (100 MHz, CDCl₃) δ 167.5, 165.2, 153.2, 151.9, 146.4, 142.2, 127.2, 124.6, 116.2, 108.2, 107.6, 61.1, 56.3, 43.6, 24.7 ppm; GC-MS 342 (M⁺).

Preparation of (E)-1-(3-(4-bromophenyl) prop-2-enoyl)-5,6-dihydropyridin-2(1H)-one

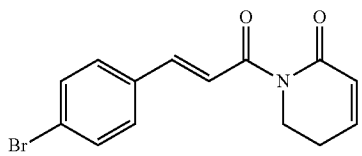

Yield 58%; yellow solid. ¹H NMR (400 MHz, CDCl₃) δ 7.65 (d, J=15.6 Hz, 1H), 7.52-7.40 (m, 5H), 6.96-6.90 (m, 1H), 6.05-6.01 (m, 1H), 4.03 (t, J=6.4 Hz, 2H), 2.50-2.43 (m, 2H) ppm; ¹³C NMR (100 MHz, CDCl₃) δ 168.9, 165.8, 145.6, 142.0, 134.0, 132.0, 130.0, 125.7, 124.2, 122.5, 41.6, 24.8 ppm

Preparation of (E)-1-(3-(4-chlorophenyl)prop-2-enoyl)-5,6-dihydropyridin-2(1H)-one

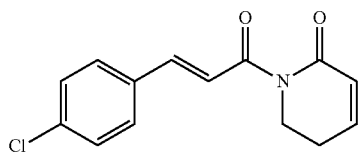

Yield 74%; ¹H NMR (400 MHz, CDCl₃) δ 7.67 (d, J=16.0 Hz, 1H), 7.51-7.45 (m, 3H), 7.35-7.30 (m, 2H), 6.97-6.91 (m, 1H), 6.06-6.01 (m, 1H), 4.03 (t, J=6.4 Hz, 2H), 2.50-2.43 (m, 2H) ppm; ¹³C NMR (100 MHz, CDCl₃) δ 168.7, 165.8, 145.6, 142.0, 135.8, 133.6, 129.4, 129.0, 125.7, 122.4, 41.6, 24.8 ppm

Preparation of (E)-1-(3-(2,4-dichlorophenyl)prop-2-enoyl)-5,6-dihydropyridin-2(1H)-one

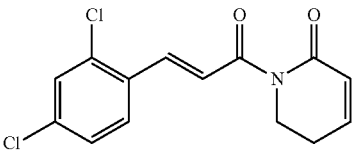

Yield 56%; yellow solid. ¹H NMR (400 MHz, CDCl₃) δ 8.03 (d, J=15.6 Hz, 1H), 7.64 (d, J=8.8 Hz, 1H), 7.49-7.42 (m, 2H), 7.27-7.25 (m, 1H), 6.99-6.94 (m, 1H), 6.04 (d, J=10.0 Hz, 1H), 4.05 (t, J=6.4 Hz, 2H), 2.52-2.47 (m, 2H) ppm; ¹³C NMR (100 MHz, CDCl₃) δ 168.3, 165.8, 145.8, 137.7, 135.9, 135.6, 132.0, 129.8, 128.7, 127.4, 125.6, 124.8, 41.6, 24.7 ppm

Preparation of (E)-1-(3-(4-fluoro-3-methylphenyl)prop-2-enoyl)-5,6-dihydropyridin-2(1H)-one

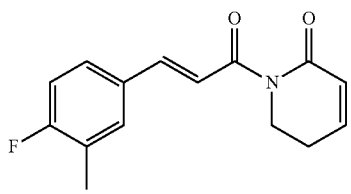

Yield 63%; ¹H NMR (400 MHz, CDCl₃) δ 7.67 (d, J=16.0 Hz, 1H), 7.44-7.35 (m, 3H), 7.01-6.90 (m, 2H), 6.05-6.02 (m, 1H), 4.03 (t, J=6.4 Hz, 2H), 2.50-2.45 (m, 2H), 2.27 (s, 3H) ppm; ¹³C NMR (100 MHz, CDCl₃) δ 168.8, 165.8, 162.4 (d, J=248 Hz), 145.5, 142.7, 131.3 (d, J=6 Hz), 131.0 (d, J=4 Hz), 127.8, 127.7, 125.8, 121.2 (d, J=2 Hz), 115.4 (d, J=23 Hz), 41.6, 24.8, 14.4 (d, J=4 Hz) ppm

Preparation of (E)-1-(3-(3-fluoro-4-methoxyphenyl)prop-2-enoyl)-5,6-dihydropyridin-2(1H)-one

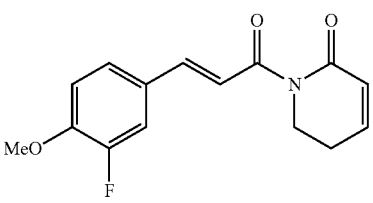

Yield 41%; ¹H NMR (400 MHz, CDCl₃) δ 7.65 (d, J=15.6 Hz, 1H), 7.40-7.30 (m, 3H), 7.00-6.92 (m, 2H), 6.05-6.02 (m, 1H), 4.04 (t, J=6.4 Hz, 2H), 3.92 (s, 3H), 2.50-2.46 (m, 2H) ppm.

Preparation of (E)-1-(3-(4-nitrophenyl)prop-2-enoyl)-5,6-dihydropyridin-2(1H)-one

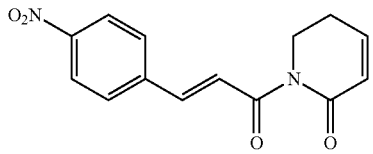

XZ12224

Yield 55%; yellow solid. $^1$H NMR (400 MHz, CDCl$_3$) δ 8.25-8.20 (m, 2H), 7.75-7.70 (m, 3H), 7.59 (d, J=16.0 Hz, 1H), 7.02-6.95 (m, 1H), 6.08-6.04 (m, 1H), 4.06 (t, J=6.4 Hz, 2H), 2.55-2.49 (m, 2H) ppm; $^{13}$C NMR (100 MHz, CDCl$_3$) δ 168.1, 165.8, 148.2, 146.0, 141.3, 139.9, 128.8, 126.1, 125.5, 124.0, 41.6, 24.7 ppm; GC-MS 272 (M$^+$).

Preparation of (E)-1-(3-(4-aminophenyl)prop-2-enoyl)-5,6-dihydropyridin-2(1H)-one

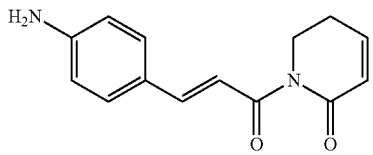

XZ12235

XZ12224 (200 mg, 0.74 mmol), iron powder (206 mg, 3.68 mmol), and NH$_4$Cl (197 mg, 3.68 mmol) in a mixture of EtOH (15 mL) and water (3 mL) were heated to 55° C. for 4 h. The mixture was then cooled to rt and extracted with EtOAc. The organic layer was separated washed with brine and dried over anhydrous Na$_2$SO$_4$. The combined organic layers were evaporated to dryness to give crude product, which was purified by flash column chromatography on silica gel using hexane/EtOAc (1:1) as eluent. Yield 57%; $^1$H NMR (400 MHz, CDCl$_3$) δ 7.69 (d, J=15.2 Hz, 1H), 7.40-7.30 (m, 3H), 6.92-6.85 (m, 1H), 6.61 (d, J=8.2 Hz, 2H), 6.01 (d, J=9.6 Hz, 1H), 4.02-3.97 (m, 4H), 2.45-2.40 (m, 2H) ppm; $^{13}$C NMR (100 MHz, CDCl$_3$) δ 169.4, 165.9, 148.8, 145.2, 144.5, 130.2, 126.0, 125.2, 117.3, 114.7, 41.6, 24.8 ppm; GC-MS 242 (M$^+$).

Preparation of (E)-1-(3-(4-acetylaminophenyl)prop-2-enoyl)-5,6-dihydropyridin-2(1H)-one

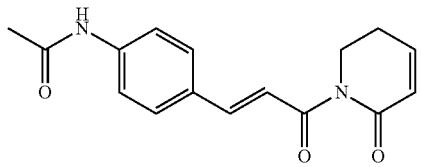

XZ12237

XZ12235 (36 mg, 0.15 mmol), Ac$_2$O (22 μL, 0.23 mmol) and trimethylamine (32 μL, 0.23 mmol) in 5 mL DCM were stirred at room temperature for 16 h. The mixture was concentrated and purified by flash column chromatography on silica gel using hexane/EtOAc (1:1) as eluent. Yield 80%;

$^1$H NMR (400 MHz, CDCl$_3$) δ 7.69-7.38 (m, 7H), 6.94-6.91 (m, 1H), 6.02 (d, J=9.6 Hz, 1H), 4.01 (t, J=6.0 Hz, 2H), 2.47-2.44 (m, 2H), 2.15 (s, 3H); $^{13}$C NMR (100 MHz, CDCl$_3$) δ 169.0, 168.4, 165.9, 144.6, 143.1, 139.7, 130.8, 129.2, 125.8, 120.6, 119.6, 41.6, 24.8, 24.7 ppm Preparation of (E)-1-(3-(2-fluorophenyl)prop-2-enoyl)-5,6-dihydropyridin-2(1H)-one

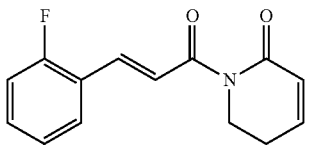

PS12676

Yield: 48%; yellow solid. $^1$H-NMR (400 MHz, CDCl$_3$) δ 7.87 (d, J=16 Hz, 1H), 7.60 (m, 1H), 7.54 (d, J=15.6 Hz, 1H), 7.34 (m, 1H), 7.15-7.05 (m, 2H), 6.94 (m, 1H), 6.03 (d, J=9.6 Hz, 1H), 4.03 (m, 2H), 2.48 (m, 2H) ppm; $^{13}$C-NMR (100 MHz, CDCl$_3$) δ 168.79, 165.73, 162.60, 160.08, 145.57, 135.63 (d, 3.1 Hz), 131.38 (d, 8.4 Hz), 128.92 (d, 3 Hz), 125.71, 124.10 (m), 123.19, 116.10 (d, 22 Hz), 41.61, 27.02 ppm. GC-MS: 245.1 (M$^+$).

Preparation of 1-(3-(3,4,5-trimethoxyphenyl)propioloyl)-5,6-dihydropyridin-2(1H)-one

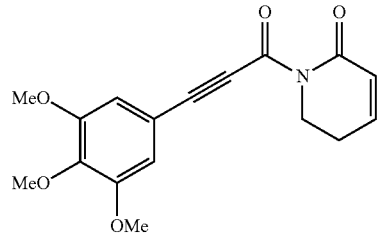

XZ12014

Yield 51%; $^1$H NMR (400 MHz, CDCl$_3$) δ 6.99-6.94 (m, 1H), 6.89 (s, 2H), 6.09-6.05 (m, 1H), 4.06 (t, J=6.4 Hz, 2H), 3.88 (s, 3H), 3.86 (s, 6H), 2.53-2.47 (m, 2H) ppm; $^{13}$C NMR (100 MHz, CDCl$_3$) δ 163.7, 153.1, 153.0, 145.6, 140.8, 125.1, 115.2, 110.4, 93.9, 83.1, 61.0, 56.2, 40.8, 24.4 ppm Example 8

Synthesis of Exemplary Piperlongumine Derivatives of Formula (II)

Preparation of (E)-3-methylene-1-(3-(3,4,5-trimethoxyphenyl)acryloyl)piperidine-2-one

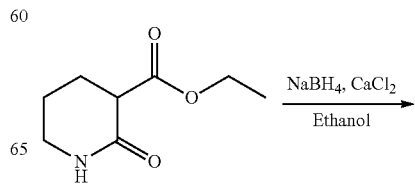

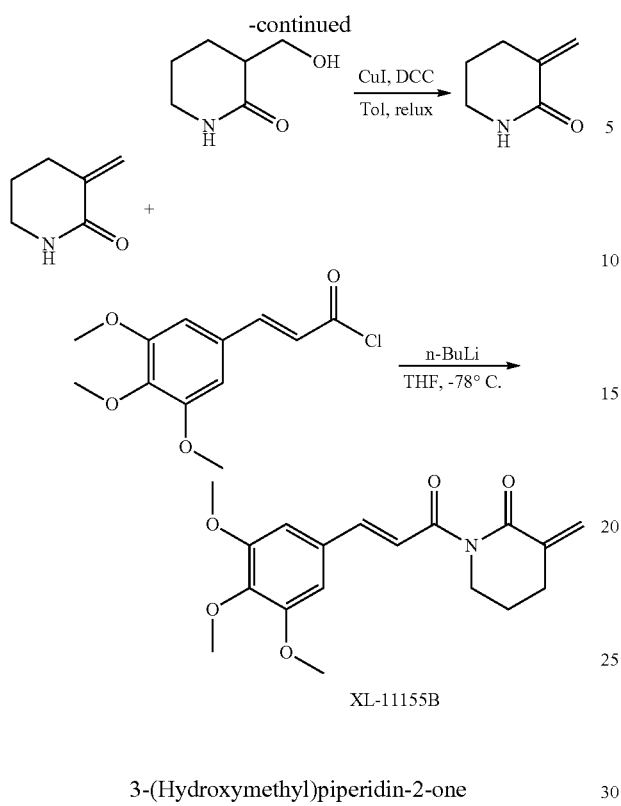

XL-11155B

3-(Hydroxymethyl)piperidin-2-one

A mixture of ethyl 2-oxopiperidine-3-carboxylate (1 g, 5.84 mmol) and calcium chloride (0.86 g, 5.85 mmol) in ethanol (10 mL) was cooled to 0° C. and treated with sodium borohydride (0.22 g, 5.84 mmol). The resulting mixture was allowed to warm to room temperature and stirred for 6 hrs. The reaction was then quenched with acetone and the pH of the mixture was adjusted to pH to 3-4 with 1.0 M HCl. The resulting mixture was extracted with methylene chloride, organic phases were combined, dried over $Na_2SO_4$, filtered, and evaporated to dryness under vacuum. The product was purified by silica gel column chromatography (377 mg, 50% yield). $^1$H-NMR (400 MHz, $CDCl_3$) δ 6.65 (br, 1H), 3.90 (br, 1H), 3.69 (m, 2H), 3.27 (m, 2H), 2.48 (m, 1H), 1.88 (m, 2H), 1.73 (m, 1H), 1.50 (m, 1H) ppm.

3-Methylene-2-piperidinone

Cuprous iodine (14 mg, 0.0074 mmol) was added to a stirred solution of 3-(Hydroxymethyl)piperidin-2-one (93 mg, 0.72 mmol) and dicyclohexylcarbodiimide (DCC) (186 mg, 0.9 mmol) in toluene (3 mL). The resulting mixture was stirred under reflux for 1.5 hrs and cooled to room temperature. Water was added and the mixture stirred overnight. Ethylacetate was added and the mixture was filtered. The aqueous phase was extracted with ethyl acetate and the combined organic phases were washed with brine, dried over $Na_2SO_4$, filtered, and evaporated to dryness under vacuum. The product was purified by silica gel column chromatography (50 mg, 63% yield). $^1$H-NMR (400 MHz, $CDCl_3$) δ 7.05 (br, 1H), 6.18 (s, 1H), 5.29 (s, 1H), 3.37 (t, J=6 Hz, 2H), 2.56 (t, J=6 Hz, 2H), 1.84 (m, 2H) ppm.

(E)-3-methylene-1-(3-(3,4,5-trimethoxyphenyl)acryloyl) 2-piperidinone

A solution of 3-Methylene-2-piperidinone (50 mg, 0.45 mmol) in THF (3 mL) was cooled to −78° C., n-BuLi (2.5M in hexane) (0.18 mL, 0.45 mmol) was added slowly. The resulting mixture was allowed to stir at −78° C. for 1 hr. A solution of (E)-3-(3,4,5-trimethoxyphenyl)acryloyl chloride (115 mg, 0.45 mmol) in THF was then added dropwise. After addition, the mixture was stirred under −78° C. for 1 hr. The reaction was then quenched with aqueous ammonium chloride solution and was extracted with ethylacetate. The combined organic phases was washed with brine, dried over $Na_2SO_4$, filtered, and evaporated to dryness under vacuum. The product was purified by silica gel column chromatography (53 mg, 36% yield). $^1$H-NMR (400 MHz, $CDCl_3$) δ 7.63 (d, J=15.2 Hz, 1H), 7.45 (d, J=15.2 Hz, 1H), 6.79 (s, 2H), 6.39 (d, J=1.6 Hz, 1H), 5.51 (dd, J=3.6, 1.6 Hz, 1H), 3.88 (s, 6H), 3.86 (s, 2H), 3.85 (m, 2H), 2.64 (m, 2H), 1.93 (m, 2H) ppm; $^{13}$C-NMR (100 MHz, $CDCl_3$) δ 170.06, 166.97, 153.45, 143.66, 140.06, 138.78, 130.84, 125.86, 121.59, 105.61, 61.06, 56.31, 45.15, 29.36, 22.54 ppm.

Preparation of (E)-3-methylene-1-(3-(3,4,5-trimethoxyphenyl)acryloyl)pyrrolidin-2-one

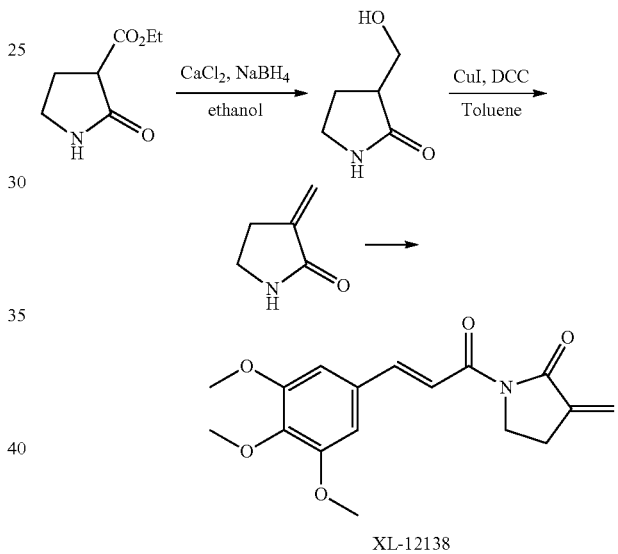

XL-12138

3-(Hydroxymethyl)pyrrolidin-2-one

Ethyl 2-oxopyrrolidine-3-carboxylate (250 mg, 1.59 mmol) was added to a suspension of $NaBH_4$ (151 mg, 3.98 mmol) and $CaCl_2$ (585 mg, 3.98 mmol) in ethanol (5 mL) under 0° C., the resulting mixture was stirred overnight at rt. The reaction was quenched with 1M HCl solution, then extracted with $CH_2Cl_2$/MeOH(10/1) for 10 to 20 times, the combined organic phases were dried over $Na_2SO_4$, filtered, and evaporated to dryness under vacuum. The product was purified by silica gel column chromatography (90 mg, 50% yield). $^1$H NMR (400 MHz, $CDCl_3$): 6.053 (br. 1H), 3.881 (m, 1H), 3.736 (m, 1H), 3.384 (m, 2H), 2.626 (m, 1H), 2.247 (m, 1H), 1.954 (m, 1H) ppm.

3-Methylenepyrrolidin-2-one 3-(Hydroxymethyl)pyrrolidin-2-one (16 mg, 0.139 mmol) was treated with CuI (2.6 mg, 0.0139 mmol) and DCC (36 mg, 0.174 mmol) in toluene under reflux for 3 h. The reaction mixture was cooled to rt and quenched with several drops of water, followed by filtration, the filtrate was concentrated and purified through column to obtain 11 mg of product (82% yield). $^1$H NMR (400 MHz, CDCl$_3$): 6.2 (br. 1H), 6.011 (s, 1H), 5.382 (s, 1H), 3.444 (t, J=6.4, 2H), 2.911 (m, 2H) ppm.

(E)-3-methylene-1-(3-(3,4,5-trimethoxyphenyl)acryloyl)pyrrolidin-2-one

3-Methylenepyrrolidin-2-one (14 mg, 0.144 mmol) was dissolved in THF and cooled to −78° C., 1.6 M n-BuLi (90 μL) was added dropwise under N$_2$ protection, the resulting mixture was stirred under −78° C. for 1 h. (E)-t-butyl 3-(3,4,5-trimethoxyphenyl)acrylate (1.5 eq) was added. After stirring at −78° C. for 1 h, the reaction was quenched with NH$_4$Cl solution, extracted with EtOAc for 3 times, the combined organic phases were washed with brine and dried over Na$_2$SO$_4$, filtered, and evaporated to dryness under vacuum. The residue was purified by flash column chromatography to afford 22 mg product (49% yield). $^1$H NMR (400 MHz, CDCl$_3$): δ 7.970 (d, J=15.6, 1H), 7.790 (d, J=15.6, 1H), 6.854 (s, 2H), 6.269 (t, J=2.8, 1H), 5.590 (t, J=2, 1H), 3.903 (s, 6H), 3.891 (s, 3H), 3.885-3.852 (m, 2H); $^{13}$CNMR (100 MHz, CDCl$_3$) δ 167.903, 167.015, 153.537, 145.932, 140.461, 140.225, 130.564, 120.979, 118.346, 105.832, 61.132, 56.336, 42.554, 23.073 ppm.

General Procedures for the Following Compounds

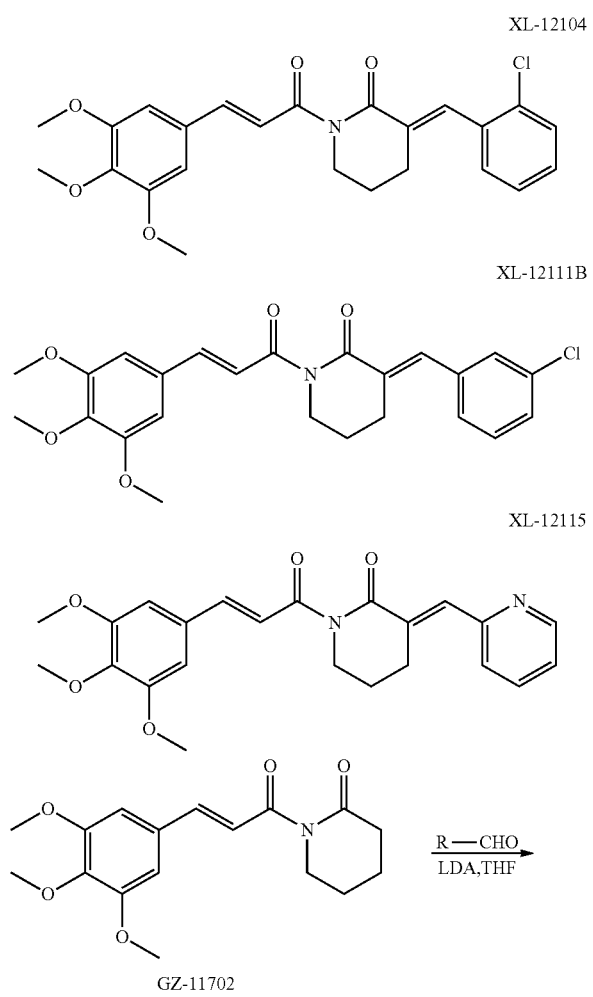

XL-12104

XL-12111B

XL-12115

GZ-11702

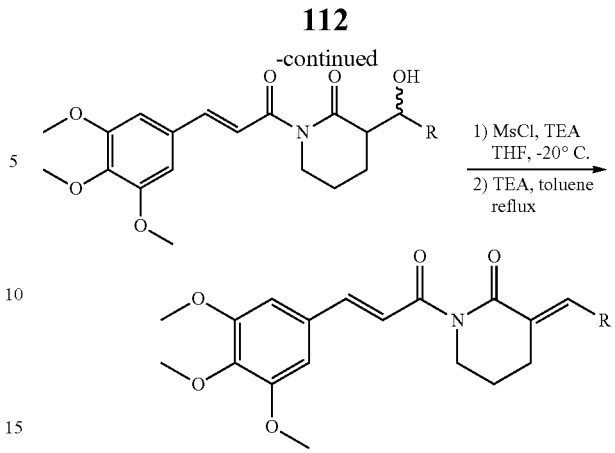

1) MsCl, TEA THF, -20° C.
2) TEA, toluene reflux

To a solution of (E)-1-(3-(3,4,5-trimethoxyphenyl)acryloyl)piperidin-2-one (150 mg, 0.47 mmol) in THF at −78° C. was added LHMDS (1.0 M, 0.56 mL, 0.564 mmol). The resulting solution was stirred at this temperature for 1 h. Aromatic aldehyde (1 eq; dissolved in small amount of THF) was added dropwise. After stirring at −78° C. for an additional hour, ammonium chloride solution was added to quench the reaction, the mixture was extracted with EtOAc for 3 times. The combined organic phases were washed with water and brine, dried over Na$_2$SO$_4$, filtered, and evaporated to dryness under vacuum. The residue was purified by flash column chromatography to afford the corresponding hydroxyl intermediate (30%-50% yield).

Methanesulfonyl chloride (1.2 eq) was added to a solution of the above intermediate and TEA (1.5 eq) in toluene under ice bath. After stirring at rt for 1 h, additional 2.5 eq TEA was added. The resulting mixture was heated to reflux for 5.5 h. Upon cooled to rt, the reaction was quenched with water and extracted with ethylacetate. The combined organic fractions were washed with brine, dried over Na$_2$SO$_4$, filtered, and evaporated to dryness under vacuum. The residue was purified by flash column chromatography to afford the desired product (75%-90% yield).

XL-12104: $^{1H}$ NMR (400 MHz, CDCl$_3$): δ 8.038 (s, 1H), 7.678 (d, 1H, J=15.6), 7.551 (d, 1H, J=15.6), 7.453 (m, 1H), 7.311-7.269 (m, 3H), 6.835 (s, 2H), 3.911 (s, 6H), 3.886 (s, 3H), 3.886-3.911 (m, 2H), 2.710 (m, 2H), 1.929 (m, 2H) ppm. $^{13}$CNMR (100 MHz, CDCl$_3$) δ 170.058, 167.463, 153.476, 143.716, 140.081, 136.256, 134.799, 134.078, 132.818, 130.891, 130.413, 129.972, 129.950, 126.565, 121.662, 105.649, 61.086, 56.343, 44.595, 26.078, 22.420 ppm.

XL-12111B: $^1$H NMR (400 MHz, CDCl$_3$): δ 7.859 (s, 1H), 7.677 (d, J=15.2, 1H), 7.509 (d, J=15.2, 1H), 7.418 (s, 1H), 7.331 (m, 3H), 6.826 (s, 2H), 3.809-3.920 (m, 11H), 2.850 (m, 2H), 1.958 (m, 2H) ppm; $^{13}$CNMR (100 MHz, CDCl$_3$) δ 169.944, 167.690, 153.514, 143.807, 140.142, 137.789, 137.319, 134.632, 132.143, 130.883, 129.935, 129.859, 129.024, 128.379, 121.571, 105.665, 61.124, 56.313, 44.292, 26.465, 22.519 ppm.

XL-12115: $^1$H NMR (400 MHz, CDCl$_3$): δ 8.712 (m, 1H), 7.829 (t, J=2, 1H), 7.726 (td, J=2 and 8, 1H), 7.673 (d, J=15.6, 1H), 7.515 (d, J=15.6, 1H), 7.423 (d, J=7.6, 1H), 7.209-7.240 (m, 1H), 6.831 (s, 2H), 3.888-3.924 (m, 11H), 3.275 (m, 2H), 1.960 (m, 2H) ppm; $^{13}$CNMR (100 MHz, CDCl$_3$) δ 169.952, 168.184, 155.047, 153.461, 149.651, 143.557, 140.036, 136.431, 136.249, 134.928, 130.914, 127.202, 122.899, 121.693, 105.589, 61.071, 56.313, 44.345, 26.647, 22.344 ppm.

Preparation of (E)-3-(2-methylpropylidene)-1-((E)-3-(3,4,5-trimethoxyphenyl)acryloyl)piperidine-2-one and (Z)-3-(2-methylpropylidene)-1-((E)-3-(3,4,5-trimethoxyphenyl)acryloyl)piperidine-2-one

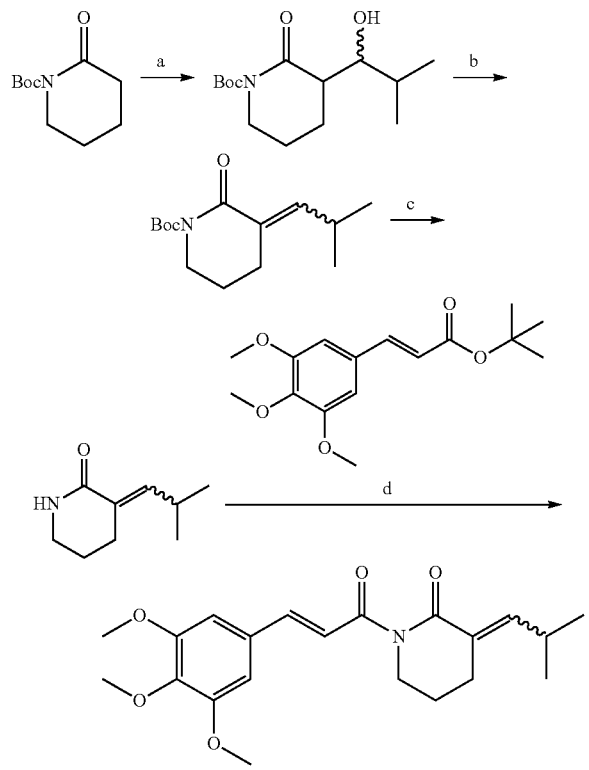

Reagents and conditions: a. LHDMS, isobutyraldehyde, THF,-78°C.; b. 1). MsCl, TEA, THF, -20° C.; 2). TEA, Tol., reflux. c. TFA, CH₂Cl₂, 0° C.; d. n-BuLi, THF, -78° C.

Reagents and conditions: a. LHDMS, isobutyraldehyde, THF, −78°C; b. 1). MsCl, TEA, THF, −20°C; 2). TEA, Tol., reflux. c. TFA, CH₂Cl₂, 0°C; d. n-BuLi, THF, −78°C.

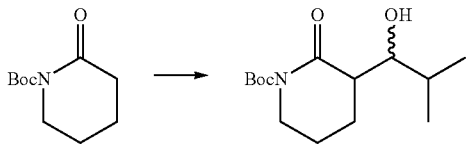 [SMILES: CC(C)(C)OC(=O)N1CCCCC1=O ; CC(C)C(O)C1CCCN(C(=O)OC(C)(C)C)C1=O]

tert-Butyl 3-(1-hydroxy-2-methylpropyl)-2-oxopiperidine-1-carboxylate

To a solution of tert-butyl 2-oxopiperidine-1-carboxylate (800 mg, 4 mmol) in THF at −78° C. was added LHDMS (1.6 M, 2.76 mL, 4.4 mmol) under N₂ protection. After stirring at this temperature for 1 h, isobutyraldehyde (0.44 mL, 4.8 mmol) was added dropwise, the resulting mixture was allowed to stir for an additional hour before quenched by slowly adding saturated NH₄Cl solution. Diluted with EtOAc and the organic fraction was washed with brine, dried over Na₂SO₄, filtered, and evaporated to dryness under vacuum. The residue was purified by flash column chromatography to afford the desired product.

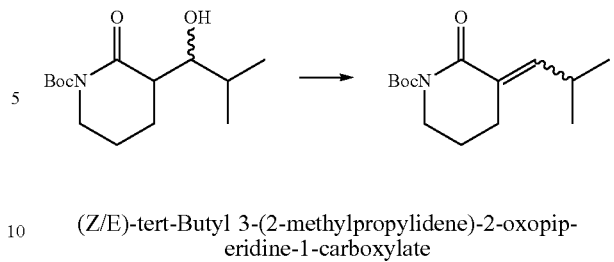

(Z/E)-tert-Butyl 3-(2-methylpropylidene)-2-oxopiperidine-1-carboxylate

To a solution of t-butyl 3-(1-hydroxy-2-methylpropyl)-2-oxopiperidine-1-carboxylate (470 mg, 1.73 mmol) and TEA (0.725 mL, 5.19 mmol) in toluene was added methanesulfonyl chloride (0.2 mL, 2.60 mmol) at 0° C., after stirring at rt for 1 h, additional 0.725 mL TEA was then added, the resulting mixture was heated to reflux and stirred under reflux for 6 h. Upon cooled down to rt, the reaction was quenched with water and extracted with EtOAc. The combined organic fractions were washed with brine, dried over Na₂SO₄, filtered, and evaporated to dryness under vacuum. The residue was purified by flash column chromatography to afford both the E isomer and Z isomer product with Z/E ratio at about 1 to 5.2 (25 mg Z isomer and 130 mg E isomer, 25% overall yield for 3 steps).

E Isomer:
¹H NMR (400 MHz, CDCl₃): δ 6.718 (dt, J=10.0, 2.0 Hz, 1H), 3.624 (m, 2H), 2.497 (m, 1H), 2.421 (td, J=1.6, 6.4 Hz, 2H), 1.799 (m, 2H), 1.590 (s, 9H), 0.960 (s, 3H), 0.943 (s, 3H); ¹³CNMR (100 MHz, CDCl₃) δ 165.679, 153.316, 149.059, 127.703, 82.677, 45.863, 28.043, 27.968, 27.839, 21.737, 21.684.

Z Isomer:
¹H NMR (400 MHz, CDCl₃): δ 5.631 (dt, J=1.6, 9.6 Hz, 1H), 3.625 (t, J=6), 3.398 (m, 1H), 2.413 (m, 2H), 1.842 (m, 2H), 1.513 (s, 9H), 0.994 (s, 3H), 0.977 (s, 3H); ¹³CNMR (100 MHz, CDCl₃) δ 166.423, 153.028, 151.078, 127.658, 82.715, 45.597, 30.624, 28.210, 28.066, 22.966, 22.830.

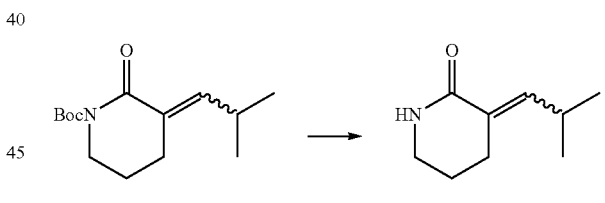

(Z or E)-3-(2-methylpropylidene)piperidin-2-one

To a solution of t-butyl 3-(2-methylpropylidene)-2-oxopiperidine-1-carboxylate (Z or E isomer, 130 mg, 0.514 mmol) in CH₂Cl₂ (8 mL) at 0° C. was added TFA (0.79 mL, 10.3 mmol), the resulting mixture was allowed to stir at 0° C. for 2 h. The reaction was then quenched with saturated sodium bicarbonate under ice bath and extracted with CH₂Cl₂, the combined organic fractions were washed with brine, dried over Na₂SO₄, filtered, and evaporated to dryness under vacuum. The residue was purified by flash column chromatography to afford the corresponding Z or E isomer in 90% yield.

E Isomer:
¹H NMR (400 MHz, CDCl₃): δ 7.15 (br, 1H), 6.639 (d, J=10 Hz, 1H), 3.319 (m, 2H), 2.576 (m, 1H), 2.464 (m, 2H), 1.806 (m, 2H), 0.999 (s, 3H), 0.982 (s, 3H); ¹³CNMR (100 MHz, CDCl₃) δ 167.334, 145.500, 126.481, 42.007, 27.064, 24.385, 22.921, 22.078.

Z Isomer:
¹H NMR (400 MHz, CDCl₃): δ 5.664 (br, 1H), 5.671 (d, 10.4 Hz, 1H), 3.725 (m, 1H), 3.304 (m, 2H), 2.411 (m, 2H), 1.833 (m, 2H), 0.986 (s, 3H), 0.970 (s, 3H); ¹³CNMR (100 MHz, CDCl₃) δ 167.030, 149.932, 125.654, 42.508, 32.400, 27.626, 23.611, 22.959.

(Z or E)-3-(2-methylpropylidene)-1-((E)-3-(3,4,5-trimethoxyphenyl)acryloyl)piperidin-2-one To a solution of 3-(2-methylpropylidene) piperidin-2-one (Z or E isomer, 10 mg, 0.065 mmol) in THF was added n-BuLi (1.6 M, 49 μL, 0.078 mmol) at −78° C. under N₂ protection, after stirring at −78° C. for 1 h, (E)-tert-butyl 3-(3,4,5-trimethoxyphenyl)acrylate (28 mg, 0.098 mmol) was added. The resulting mixture was stirred at −78° C. for 45 min and then quenched with saturated NH₄Cl water solution. The whole mixture was extracted with EA for several times, the combined organic phase was washed with brine, dried over Na₂SO₄, filtered, and evaporated to dryness under vacuum. The residue was purified by flash column chromatography to afford the corresponding Z or E isomer (48% yield for Z isomer and 58% yield for E isomer).

E Isomer:
¹H NMR (400 MHz, CDCl₃): δ 7.631 (d, J=16 Hz, 1H), 7.500 (d, J=16 Hz, 1H), 6.767 (d, J=11.2 Hz, 1H), 6.804 (s, 2H), 3.895 (s, 6H), 3.885 (s, 3H), 3.845 (m, 2H), 2.630 (m, 1H), 2.557 (m, 2H), 1.915 (m, 2H), 1.075 (s, 3H), 1.058 (s, 3H); ¹³CNMR (100 MHz, CDCl₃) δ 170.058, 168.024, 153.476, 150.425, 143.367, 139.990, 131.020, 127.977, 121.920, 105.604, 61.109, 56.351, 44.223, 27.960, 24.294, 22.382, 21.873.

Z Isomer:
¹H NMR (400 MHz, CDCl₃): δ 7.640 (d, J=16 Hz, 1H), 7.388 (d, 16 Hz, 1H), 6.802 (s, 2H), 5.778 (d, J=9.6 Hz, 1H), 3.899 (s, 6H), 3.879 (s, 3H), 3.800 (t, J=6.4 Hz, 2H), 3.418 (m, 1H), 2.504 (t, J=5.6 Hz, 2H), 1.912 (q, J=6.4, 5.6 Hz, 2H), 1.047 (s, 3H), 1.030 (s, 3H); ¹³CNMR (100 MHz, CDCl₃) δ 169.625, 168.768, 153.461, 152.300, 143.314, 140.028, 130.967, 127.627, 121.670, 105.680, 61.117, 56.351, 43.533, 30.373, 28.271, 22.830, 22.617.

Preparation of
(E)-3-methylene-1-(styrylsulfonyl)piperidine-2-one

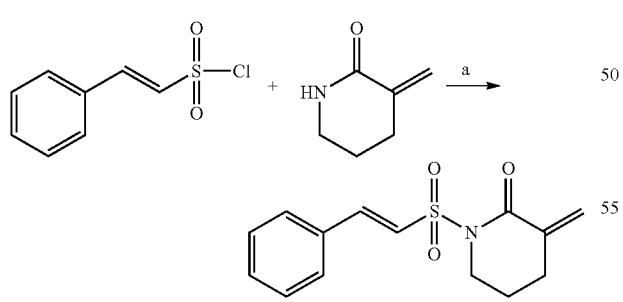

Condition: a. n-BuLi, THF, -78° C.

To a solution of 3-methylenepiperidin-2-one (80 mg, 9.0 mmol) in THF at −78° C. was added n-BuLi (1.6 M, 0.54 mL, 10.8 mmol), after stirring at this temperature for 1 h, (E)-2-phenylethenesulfonyl chloride (146 mg, 9.0 mmol, dissolved in small amount of THF) was added. The resulting mixture was stirred for another 1 h and then quenched with saturated NH₄Cl water solution. The whole mixture was extracted with EA for several times, the combined organic phase was washed with brine, dried over Na₂SO₄, filtered, and evaporated to dryness under vacuum. The residue was purified by flash column chromatography to afford the desired product (60 mg, 30% yield).

¹H NMR (400 MHz, CDCl₃): δ 7.663 (d, J=16 Hz, 1H), 7.529 (m, 2H), 7.415 (m, 3H), 7.320 (d, J=16 Hz, 1H), 6.365 (d, J=0.8 Hz, 1H), 5.483 (d, 0.8 Hz, 1H), 3.891 (t, J=6 Hz, 2H), 2.598 (t, J=6 Hz, 2H), 1.969 (q, J=6 Hz, 6 Hz, 2H) ppm; ¹³CNMR (100 MHz, CDCl₃) δ 164.693, 144.414, 137.182, 132.317, 131.521, 129.214, 128.887, 126.148, 124.918, 46.796, 29.258, 23.293 ppm.

Preparation of (E)-3-methylene-1-(3-(3, 4, 5-trimethoxyphenyl)acryloyl)azepan-2-one

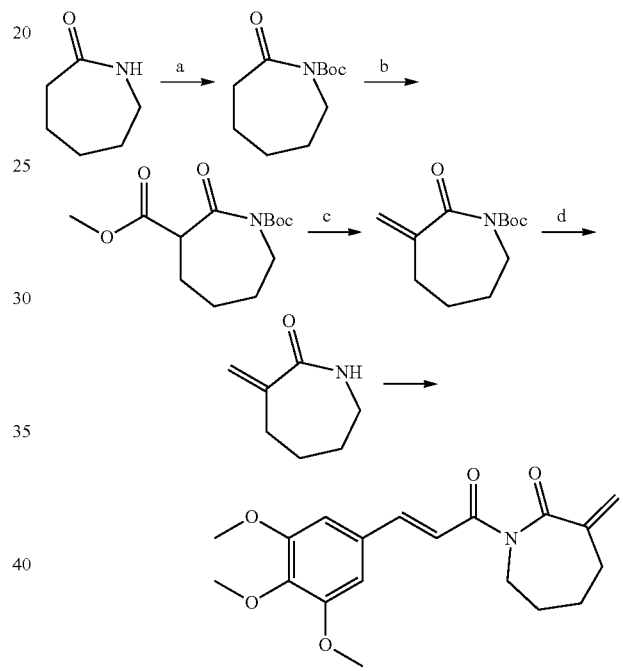

Conditions: a. DMAP, Et₃N, Boc₂O, CH₂Cl₂, r.t.; b. LHMDS, THF, -78° C.;
c. (HCHO)n, 18-crown-6, K₂CO₃, Tol, reflux; d. TFA, CH₂Cl₂, 0° C.

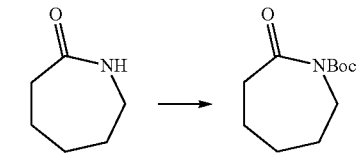 [SMILES: O=C1CCCCCN1 ; CC(C)(C)OC(=O)N1CCCCCC1=O]

tert-butyl 2-oxoazepane-1-carboxylate

To a solution of ε-Caprolactam (3 g, 26.5 mmol), DMAP (647 mg, 5.3 mmol) and Et3N (10 ml, 66.3 mmol) in CH2Cl2 at 00 C was added Boc2O (8.7 g, 39.75 mmol), the resulting mixture was stirred at r.t overnight. Evaporation of solvent gave a residue which was purified through column to get 5 g product (89% yield).

¹H NMR (400 MHz, CDCl₃): δ 3.760 (t, J=2 Hz, 2H), 2.648 (m, 2H), 1.745 (m, 6H), 1.522 (s, 9H). ¹³CNMR (100

MHz, CDCl₃) δ 175.826, 153.013, 82.821, 46.227, 39.594, 29.318, 28.757, 28.127, 23.604.

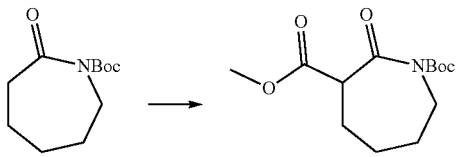 [SMILES: CC(C)(C)OC(=O)N1CCCCCC1=O ; COC(=O)C1CCCCN(C(=O)OC(C)(C)C)C1=O]

1-tert-butyl 3-methyl
2-oxoazepane-1,3-dicarboxylate

To a solution of tert-butyl 2-oxoazepane-1-carboxylate (2.45 g, 11.5 mmol) in THF at −780 C was added 1M LHMDS (13 ml, 13.2 mmol), the resulting mixture was stirred at this temperature for 45 min and methyl carbonochloridate (1 ml, 12.6 mmol) was then added, the whole mixture was stirred for additional 1 h and quenched with quenched with saturated NH4Cl water solution, followed by extraction with EA for several times, the combined organic phase was washed with brine and dried over anhydrous sodium sulfate. Evaporation of solvent gave a residue which was purified through column to get 2.7 g product. (87% yield).

¹H NMR (400 MHz, CDCl₃): δ 5.362 (br, 1H), 3.813 (s, 3H), 3.580 (m, 2H), 2.116 (m, 2H), 1.746 (m, 2H), 1.550 (m, 2H), 1.458 (s, 9H); ¹³CNMR (100 MHz, CDCl₃) δ 154.068, 153.150, 146.001, 111.341, 81.046, 55.099, 29.280, 28.226, 28.081, 24.515, 24.014.

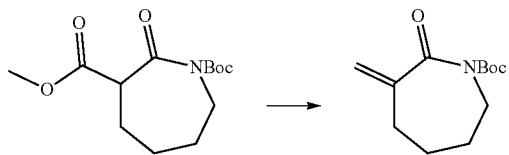 [SMILES: COC(=O)C1CCCCN(C(=O)OC(C)(C)C)C1=O ; C=C1CCCCN(C(=O)OC(C)(C)C)C1=O]

tert-butyl 3-methylene-2-oxoazepane-1-carboxylate

To a suspension of 1-tert-butyl 3-methyl 2-oxoazepane-1,3-dicarboxylate (90 mg, 0.33 mmol), 18-crown-6 (26 mg, 0.1 mmol), K₂CO₃ (137 mg, 1 mmol) in Toluene was added paraformaldehyde (348 mg, 11.55 mmol), the resulting mixture was stirred under reflux for 4-5 hours and then cooled to r.t. and water was added, the whole mixture was extracted with EA for 3 times. The combined organic phase was washed with brine and dried over anhydrous sodium sulfate. Evaporation of solvent gave a residue which was purified through column to give 30 mg product. (41% yield)

¹H NMR (400 MHz, CDCl₃): δ 5.764 (s, 1H), 5.388 (s, 1H), 3.670 (m, 2H), 2.424 (m, 2H), 1.740 (m, 4H), 1.527 (s, 9H); ¹³CNMR (100 MHz, CDCl₃) δ 172.653, 152.846, 147.298, 123.264, 82.738, 46.060, 32.589, 29.227, 28.210, 28.165.

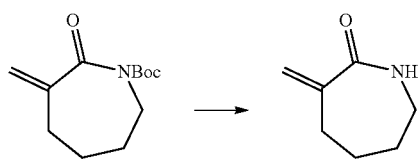

3-methyleneazepan-2-one

To a solution of tert-butyl 3-methylene-2-oxoazepane-1-carboxylate (30 mg, 0.133 mmol) in CH₂Cl₂ (2 ml) at 0° C. was added TFA (0.2 ml, 2.66 mmol), the resulting solution was stirred at this temperature for 2 h. Saturated sodium bicarbonate solution was added until PH larger than 7, the mixture was then extracted with CH₂Cl₂ for 5-10 times and the combined organic phase was washed with brine and dried over anhydrous sodium sulfate. Evaporation of solvent gave a residue which was purified through column to get product (11 mg, 66% yield).

¹H NMR (400 MHz, CDCl₃): δ 6.616 (br, 1H), 5.595 (s, 1H), 5.283 (s, 1H), 3.185 (m, 2H), 2.376 (m, 2H), 1.757 (m, 4H); ¹³CNMR (100 MHz, CDCl₃) δ 176.053, 146.441, 120.380, 42.827, 32.771, 29.698, 28.984.

(E)-3-methylene-1-(3-(3, 4, 5-trimethoxyphenyl)
acryloyl)azepan-2-one

To a solution of 3-methyleneazepan-2-one (16 mg, 0.128 mmol) in THF at −78° C. was added 1.6 M n-BuLi (88 ul) after stirring at this temperature for 1 h, (E)-tert-butyl 3-(3,4,5-trimethoxyphenyl)acrylate (45 mg, 0.154 mmol) was then added. The resulting mixture was stirred at −78° C. for additional 1 h and then quenched with saturated NH₄Cl solution. The whole mixture was then extracted with EA for several times and the combined organic phase was washed with brine and dried over anhydrous sodium sulfate. Evaporation of solvent gave a residue which was purified chromatographically to get pure product (20 mg, 45% yield).

¹H NMR (400 MHz, CDCl₃): δ 7.703 (d, J=15.2 Hz, 1H), 7.288 (d, 15.6 Hz, 1H), 6.692 (s, 2H), 5.848 (d, J=1.2 Hz, 1H), 5.498 (d, J=1.2 Hz, 1H), 3.893 (m, 11H), 2.495 (m, 2H), 1.807-1.852 (m, 2H), 1.200-1.781 (m, 2H); ¹³CNMR (100 MHz, CDCl₃) δ 174.953, 167.690, 153.506, 147.139, 144.346, 140.111, 130.716, 123.916, 119.849, 105.566, 61.109, 56.336, 44.178, 32.825, 29.432, 28.119.

Preparation of (E)-3-(2-chlorobenzylidene)-1-((E)-3-(3,4,5-trimethoxyphenyl)acryloyl)azepan-2-one

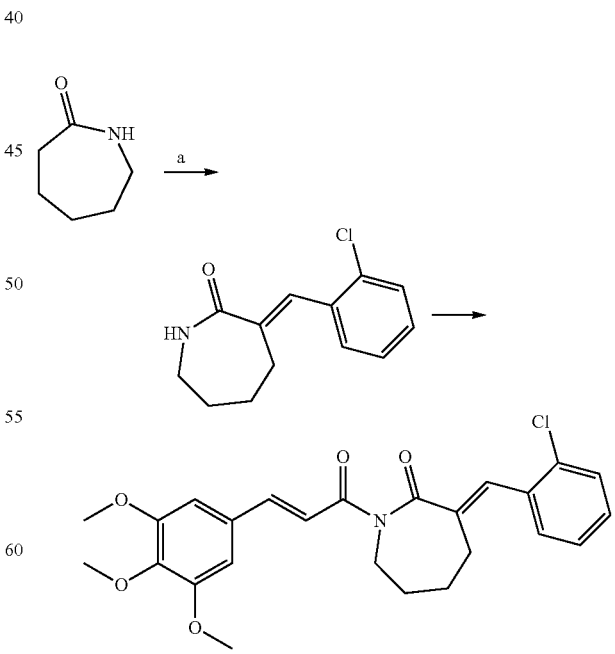

Conditions and reagents: a. (1) TFAA, Tol; (2) 2-chlorobenzaldehyde, t-BuOK, THF.

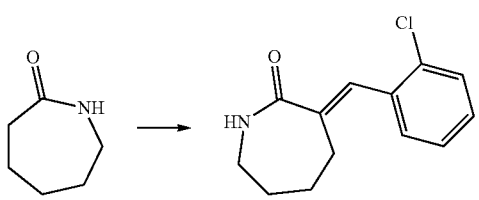 [SMILES: O=C1CCCCCN1 ; O=C1NCCCC/C1=C\c1ccccc1Cl]

(E)-3-(2-chlorobenzylidene)azepan-2-one

Made according to literature. TFAA was added to a solution of azepan-2-one (0.5 g, 4.4 mmol) in toluene at 0° C., after stirring under ice bath for 1 h, the solvent was removed to give a residue. The residue was mixed with 2-chlorobenzaldehyde (0.558 g, 3.98 mmol) and charged to a suspension of t-BuOK (0.596 mg, 5.3 mmol) in THF at 0° C., the resulting mixture was then heated to 50-60° C. and stirred at this temperature for 1.5 h. The reaction mixture was concentrated under vacuum and water was then added. The resulting mixture was extracted with EA for 3 times, the combined organic phase was washed with brine and dried over anhydrous sodium sulfate. Evaporation of solvent gave a residue which was purified through column to get product (0.6 g, 60% yield).

$^1$H NMR (400 MHz, CDCl$_3$): δ 7.407-7.431 (m, 1H), 7.314-7.338 (m, 1H), 7.173-7.280 (m, 2H), 7.173 (s, 1H), 6.392 (br, 1H), 3.299 (m, 2H), 2.423 (m, 2H), 1.761 (m, 4H); $^{13}$CNMR (100 MHz, CDCl$_3$) δ 175.773, 140.278, 134.708, 134.116, 131.748, 130.109, 129.714, 129.062, 126.595, 42.463, 28.764, 27.687, 27.118.

(E)-3-(2-chlorobenzylidene)-1-((E)-3-(3,4,5-trimethoxyphenyl)acryloyl)azepan-2-one To a solution of (E)-3-(2-chlorobenzylidene)azepan-2-one (24 mg, 0.102 mmol) in THF at −78° C. was added 1.6 M n-BuLi (70 ul, 0.112 mmol), after stirring at −78° C. for 1 h, (E)-tert-butyl 3-(3,4,5-trimethoxyphenyl)acrylate (30 mg, 0.103 mmol) was added and the resulting mixture was stirred at −78° C. for additional 1 h. The reaction was quenched with saturated NH$_4$Cl solution and then extracted with EA for 3 times, the combined organic phase was washed with brine and dried over anhydrous sodium sulfate. Evaporation of solvent gave a residue which was purified through column to get pure product as white solid (30 mg, 65% yield).

$^1$H NMR (400 MHz, CDCl$_3$): δ 7.735 (d, J=15.2 Hz, 1H), 7.449-7.473 (m, 1H), 7.375-7.411 (m, 3H), 7.293-7.316 (m, 2H), 6.819 (s, 2H), 4.020 (m, 2H), 3.918 (s, 6H), 3.888 (s, 3H), 2.535 (m, 2H), 1.809 (m, 4H); $^{13}$CNMR (100 MHz, CDCl$_3$) δ 175.097, 167.759, 153.521, 144.536, 140.954, 140.142, 134.587, 134.260, 133.949, 130.747, 129.965, 129.790, 129.722, 126.823, 119.909, 105.634, 61.117, 56.373, 44.018, 27.831, 27.649, 27.277.

REFERENCES

1. Anerjee T and Audhurci S. (1986). The crystal and molecular structure of N-(3,4,5-trimethoxycinnamoyl)-A3-piperidine-2-one, an amide alkaloid (piperlongumine), C171-119N05. Can J Chem 64:876-880.
2. Baker D J, Wijshake T, Tehkonia T, LeBrasseur N K, Childs B G, van de Sluis B, Kirkland J L and van Deursen J M. Clearance of p161"k4a-positive senescent cells delays ageing-associated disorders. Nature 479:232-236.
3. Bezerra D P, Pessoa C, de Moraes M O, Saker-Neto N, Silveira E R and Costa-Lotufo L V. Overview of the therapeutic potential of piplartine (piperlongumine). Eur J Pharma Sci 2013, 48(3):453-463.
4. Bokesch H R, Gardella R S, Rabe D C, Bottaro D P, Linehan W M, McMahon J B and McKee T C. (2011). A new hypoxia inducible factor-2 inhibitory pyrrolinone alkaloid from roots and stems of *Piper sarmentosum*. Chem Pharm Bull 59(9):1178-1179.
5. Campisi J. (2005). Senescent cells, tumor suppression, and organismal aging: good citizens, bad neighbors. Cell 120:513-522.
6. Campisi J. (2011). Cellular senescence: putting the paradoxes in perspective. Curr Opin Genet rev 21:107-112.
7. Dodson C D, Dyer L A, Searcy J, Wright Z and Letourneau D K. (2000). Cenocladamide, a dihydropyridone alkaloid from *Piper cenocladum*. Phytochemistry 53:51-54.
8. Duh C Y, Wu Y C and Wang S K. (1990). Cytotoxic pyridone alkaloids from the leaves of *Piper aborescens*. J Nat Prod 53:1575-1577.
9. Fontenele J13, Leal L K, Silveira E R, Felix F H, Bezerra Felipe C F and Viana G S. (2009). Antiplatelet effects of piplartine, an alkamide isolated from *Piper tuberculatum*: possible involvement of cyclooxygenase blockade and antioxidant activity. J Pharm Pharmacol 61(4):511-515.
10. Joshi S B, Kamat Y N and Saksena A K. (1968). On the structure of piplartine and a synthesis of dihydropiplartine. Tetrahedron Lett 9(20):2395-2400.
11. Kubo M, Ishii R, Ishino Y, Harada K, Matsui N, Akagi M, Kato E, Hosoda S and Fukuyama Y. (2013). Evaluation of constituents of *Piper retrofractum* fruits on neurotrophic activity. J Nat Prod 76:769-773.
12. Raj L, Ide T, Gurkar A U, Foley M, Schenone M, Li X, Tolliday N J, Golub T R, Carr S A, Shamji A F, Stern A M, Mandinova A, Schreiber S L and Lee S W. (2011). Selective killing of cancer cells by a small molecule targeting the stress response to ROS. Nature 475:231-234.
13. Rao V R, Muthenna P, Shankaraiah G, Akileshwari C, Babu K H, Suresh G, Babu K S, Chandra K, Rotte S, Prasad K R, Yadav P A. (2012). Synthesis and biological evaluation of new piplartine analogues as potent aldose reductase inhibitors (ARIs). Eur J Med Chem 57:344-361.
14. Rodier F and Campisi J. (2011). Four faces of cellular senescence. J Cell Biol 192:547-556.

What is claimed is:

1. A method of selectively killing one or more senescent cells from a cell population or tissue, the method comprising contacting the senescent cells with an effective amount of a composition comprising a pharmaceutically acceptable carrier and a compound comprising Formula (II):

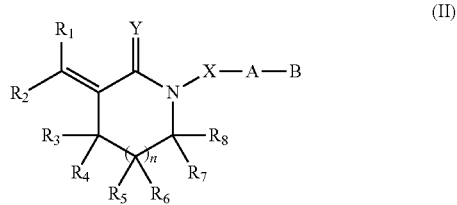

wherein:
X is selected from the group consisting of C(O), C(S), C(NH) and S(O)₂;
Y is selected from the group consisting of O, NH and S;
n is 1;
$R_1$, $R_2$, $R_3$, $R_4$, $R_5$, $R_6$, $R_7$, and $R_8$ are each independently selected from the group consisting of hydrogen, deuterium, halogen, $CF_3$, CN, OH, $OCH_3$, OR, SR, NRR, NRCOR, NRCONRR, $NRCO_2R$, COR, $CO_2R$, NOR, $NO_2$, CONRR, OC(O)NRR, $SO_2R$, $SO_2NRR$, $NRSO_2R$, $NRSO_2NRR$, C(O)C(O)R, and C(O)CH₂C(O)R, a substituted or unsubstituted C1 to C6 alkyl, a substituted or unsubstituted C1 to C6 alkenyl, a substituted or unsubstituted C1 to C6 alkynyl, and a substituted or unsubstituted aryl;
R is independently selected from the group consisting of hydrogen, substituted C1-C4 aliphatic moiety, aliphatic moiety containing nitrogen, oxygen, or sulfur, or alternately, two R moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur;
A is selected from the group consisting of

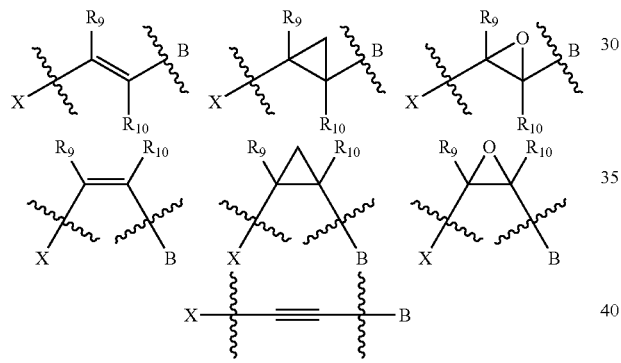

wherein:
$R_9$ and $R_{10}$ are independently selected from the group consisting of hydrogen, deuterium, halogen, $CF_3$, CN, OH, $OCH_3$, OR', SR', NR'R', NR'COR', NR'CONR'R', $NR'CO_2R'$, COR', $CO_2R'$, NOR', $NO_2$, CONR'R', OC(O)NR'R', $SO_2R$, $SO_2NR'R'$, $NR'SO_2R'$, $NR'SO_2NR'R'$, C(O)C(O)R', and C(O)CH₂C(O)R', a substituted or unsubstituted C1 to C6 alkyl, a substituted or unsubstituted C1 to C6 alkenyl, a substituted or unsubstituted C1 to C6 alkynyl, and a substituted or unsubstituted aryl;
R' is independently selected from the group consisting of hydrogen, substituted C1-C4 aliphatic moiety, aliphatic moiety containing nitrogen, oxygen, or sulfur, or alternately, two R' moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur;
Optionally, $R_9$ and $R_{10}$ are taken together to form a 5-8 membered saturated or unsaturated ring having 0-3 heteroatoms independently selected from the group consisting of nitrogen, oxygen, or sulfur;

B is

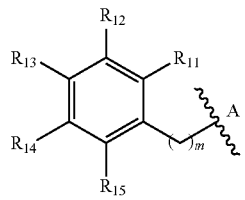

wherein:
$R_{11}$, $R_{12}$, $R_{13}$, $R_{14}$, and $R_{15}$ are each independently selected from the group consisting of hydrogen, deuterium, halogen, $CF_3$, CN, OH, $OCH_3$, OR", SR", NR"R", NR"COR", NR"CONR"R", $NRCO_2R$", COR", $CO_2R$", NOR", $NO_2$, CONR"R", OC(O)NR"R", $SO_2R$", $SO_2NR"R"$, $NR"SO_2R$", $NR"SO_2NR"R"$, C(O)C(O)R", and C(O)CH₂C(O)R", a substituted or unsubstituted C1 to C6 alkyl, a substituted or unsubstituted C1 to C6 alkenyl, a substituted or unsubstituted C1 to C6 alkynyl, and a substituted or unsubstituted aryl;
R" is independently selected from the group consisting of hydrogen, substituted C1-C4 aliphatic moiety, aliphatic moiety containing nitrogen, oxygen, or sulfur, or alternately, two R" moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur;
Optionally, $R_{11}$ and $R_{12}$, $R_{12}$ and $R_{13}$, $R_{13}$ and $R_{14}$, and $R_{14}$ and $R_{15}$ are taken together to form a 4-8 membered saturated or unsaturated ring having 0-3 heteroatoms independently selected from the group consisting of nitrogen, oxygen, or sulfur;
m is an integer from 0-6; and
or B is one or more monocyclic aryl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from the group consisting of nitrogen, oxygen or sulfur, or an 8-10 membered bicyclic heteroaryl ring having 1-5 heteroatoms independently selected from the group consisting of nitrogen, oxygen, or sulfur;
wherein any and all of the substituted described are substituted with one or more groups that are independently a methyl group or methoxy group.

2. The method of claim 1, wherein the senescent cells are senescent due to replicative cellular senescence, premature cellular senescence, or therapy-induced senescence.

3. The method of claim 1, wherein the senescent cells are from an age-related pathology.

4. The method of claim 1, wherein the composition further comprises at least one inhibitor of one or more anti-apoptotic proteins in the Bcl-2 family.

5. The method of claim 4, wherein the inhibitor is ABT263.

6. The method of claim 1, wherein the cell population or tissue is in a human subject.

7. The method of claim 6, wherein the subject has a received DNA-damaging therapy.

8. A method of killing therapy-induced senescent cells from a cell population or tissue, the method comprising contacting the therapy-induced senescent cells with an effective amount of a composition comprising a pharmaceutically acceptable carrier and a compound comprising formula (II):

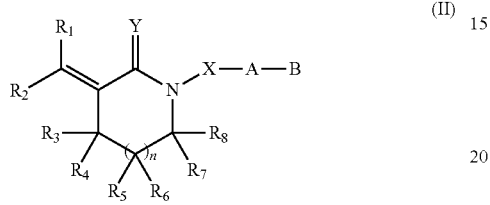

(II)

wherein:
- X is selected from the group consisting of C(O), C(S), C(NH) and S(O)$_2$;
- Y is selected from the group consisting of O, NH and S;
- n is 1;
- $R_1$, $R_2$, $R_3$, $R_4$, $R_5$, $R_6$, $R_7$, and $R_8$ are each independently selected from the group consisting of hydrogen, deuterium, halogen, CF$_3$, CN, OH, OCH$_3$, OR, SR, NRR, NRCOR, NRCONRR, NRCO$_2$R, COR, CO$_2$R, NOR, NO$_2$, CONRR, OC(O)NRR, SO$_2$R, SO$_2$NRR, NRSO$_2$R, NRSO$_2$NRR, C(O)C(O)R, and C(O)CH$_2$C(O)R, a substituted or unsubstituted C1 to C6 alkyl, a substituted or unsubstituted C1 to C6 alkenyl, a substituted or unsubstituted C1 to C6 alkynyl, and a substituted or unsubstituted aryl;
- R is independently selected from the group consisting of hydrogen, substituted C1-C4 aliphatic moiety, aliphatic moiety containing nitrogen, oxygen, or sulfur, or alternately, two R moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur;
- A is selected from the group consisting of

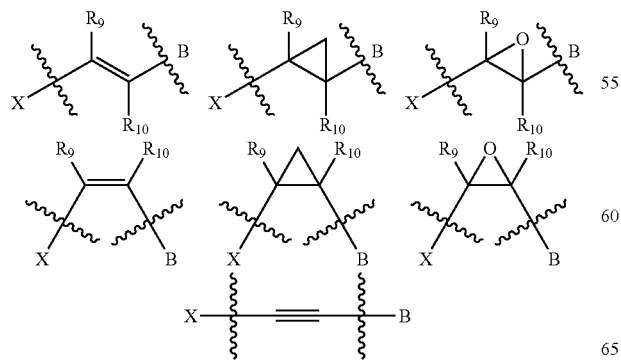

wherein:
- $R_9$ and $R_{10}$ are independently selected from the group consisting of hydrogen, deuterium, halogen, CF$_3$, CN, OH, OCH$_3$, OR', SR', NR'R', NR'COR', NR'CONR'R', NR'CO$_2$R', COR', CO$_2$R', NOR', NO$_2$, CONR'R', OC(O)NR'R', SO$_2$R, SO$_2$NR'R', NR'SO$_2$R', NR'SO$_2$NR'R', C(O)C(O)R', and C(O)CH$_2$C(O)R', a substituted or unsubstituted C1 to C6 alkyl, a substituted or unsubstituted C1 to C6 alkenyl, a substituted or unsubstituted C1 to C6 alkynyl, and a substituted or unsubstituted aryl;
- R' is independently selected from the group consisting of hydrogen, substituted C1-C4 aliphatic moiety, aliphatic moiety containing nitrogen, oxygen, or sulfur, or alternately, two R' moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur;
- Optionally, $R_9$ and $R_{10}$ are taken together to form a 5-8 membered saturated or unsaturated ring having 0-3 heteroatoms independently selected from the group consisting of nitrogen, oxygen, or sulfur;
- B is

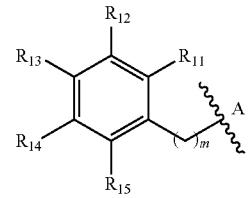

wherein:
- $R_{11}$, $R_{12}$, $R_{13}$, $R_{14}$, and $R_{15}$ are each independently selected from the group consisting of hydrogen, deuterium, halogen, CF$_3$, CN, OH, OCH$_3$, OR", SR", NR"R", NR"COR", NR"CONR"R", NRCO$_2$R", COR", CO$_2$R", NOR", NO$_2$, CONR"R", OC(O)NR"R", SO$_2$R", SO$_2$NR"R", NR"SO$_2$R", NR"SO$_2$NR"R", C(O)C(O)R", and C(O)CH$_2$C(O)R", a substituted or unsubstituted C1 to C6 alkyl, a substituted or unsubstituted C1 to C6 alkenyl, a substituted or unsubstituted C1 to C6 alkynyl, and a substituted or unsubstituted aryl;
- R" is independently selected from the group consisting of hydrogen, substituted C1-C4 aliphatic moiety, aliphatic moiety containing nitrogen, oxygen, or sulfur, or alternately, two R" moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur;
- Optionally, $R_{11}$ and $R_{12}$, $R_{12}$ and $R_{13}$, $R_{13}$ and $R_{14}$, and $R_{14}$ and $R_{15}$ are taken together to form a 4-8 membered saturated or unsaturated ring having 0-3 heteroatoms independently selected from the group consisting of nitrogen, oxygen, or sulfur;
- m is an integer from 0-6; and
- or B is one or more monocyclic aryl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from the group consisting of nitrogen, oxygen or sulfur, or an 8-10 membered bicyclic heteroaryl ring having 1-5 heteroatoms independently selected from the group consisting of nitrogen, oxygen, or sulfur;

wherein any and all of the substituted described are substituted with one or more groups that are independently a methyl group or methoxy group.

9. The method of claim 8, wherein the composition further comprises at least one inhibitor of one or more anti-apoptotic proteins in the Bcl-2 family.

10. The method of claim 9, wherein the inhibitor is ABT263.

11. The method of claim 8, wherein the therapy-induced senescent cells are in a human subject.

\* \* \* \* \*